US012605371B2

(12) United States Patent
Morser et al.

(10) Patent No.: US 12,605,371 B2
(45) Date of Patent: Apr. 21, 2026

(54) COMBINATION THERAPY FOR CANCER

(71) Applicants:The Board of Trustees of the Leland Stanford Junior University, Stanford, CA (US); The United States Government as represented by the Department of Veterans Affairs, Washington, DC (US)

(72) Inventors: Michael J. Morser, San Francisco, CA (US); Lawrence L.K Leung, Hillsborough, CA (US); Timothy Myles, Sunnyvale, CA (US)

(73) Assignees: The Board of Trustees of the Leland Stanford Junior University, Stanford, CA (US); The United States Governmment as represented by the Department of Veterans Affairs, Washington, DC (US)

( * ) Notice: Subject to any disclaimer, the term of this patent is extended or adjusted under 35 U.S.C. 154(b) by 570 days.

(21) Appl. No.: 18/014,971

(22) PCT Filed: Jul. 26, 2021

(86) PCT No.: PCT/US2021/043197
§ 371 (c)(1),
(2) Date: Jan. 6, 2023

(87) PCT Pub. No.: WO2022/026398
PCT Pub. Date: Feb. 3, 2022

(65) Prior Publication Data
US 2023/0255948 A1     Aug. 17, 2023

Related U.S. Application Data

(60) Provisional application No. 63/059,673, filed on Jul. 31, 2020.

(51) Int. Cl.
*A61K 31/4439* (2006.01)
*A61K 31/437* (2006.01)
(Continued)

(52) U.S. Cl.
CPC ........ *A61K 31/4439* (2013.01); *A61K 31/437* (2013.01); *A61K 31/506* (2013.01); *A61K 31/519* (2013.01); *A61P 35/00* (2018.01)

(58) Field of Classification Search
CPC .... A61K 31/4439; A61K 31/437; A61P 35/00
(Continued)

(56) References Cited

U.S. PATENT DOCUMENTS

2014/0162888 A1     6/2014  Kuslich et al.
2014/0220580 A1     8/2014  Brown et al.
(Continued)

FOREIGN PATENT DOCUMENTS

WO     WO-2017033113 A1 *  3/2017   ............. A61K 45/06
WO     WO2018159580 A1     9/2018
(Continued)

OTHER PUBLICATIONS

Al-Horani RA, Desai UR. Factor Xla inhibitors: a review of the patent literature. Expert opinion on therapeutic patents. Mar. 3, 2016; 26(3):323-45. (Year: 2016).*
(Continued)

*Primary Examiner* — Jeffrey S Lundgren
*Assistant Examiner* — Heather Dahlin
(74) *Attorney, Agent, or Firm* — Jenny L. Buchbinder; Bozicevic, Field & Francis LLP

(57) ABSTRACT

Methods for treating cancer using combination therapy with an anti-coagulant and a B-Raf inhibitor and/or a mitogen-activated protein kinase (MEK) inhibitor are disclosed. The anti-coagulant may be a direct inhibitor of thrombin or an
(Continued)

indirect inhibitor of thrombin, such as an inhibitor of factor Xa, factor XIa, or other coagulation factors.

19 Claims, 53 Drawing Sheets

Specification includes a Sequence Listing.

(51) Int. Cl.
  *A61K 31/506*        (2006.01)
  *A61K 31/519*        (2006.01)
  *A61P 35/00*          (2006.01)

(58) Field of Classification Search
  USPC ........................................................ 514/337
  See application file for complete search history.

(56)                          References Cited

U.S. PATENT DOCUMENTS

| | | |
|---|---|---|
| 2015/0118222 A1 | 4/2015 | Levy et al. |
| 2017/0020964 A1 | 1/2017 | Conejo-Garcia et al. |
| 2017/0304419 A1 | 10/2017 | Yu et al. |

FOREIGN PATENT DOCUMENTS

| | | |
|---|---|---|
| WO | 2019038367 A1 | 2/2019 |
| WO | WO2021030209 | 2/2021 |

OTHER PUBLICATIONS

Haugh AM, Johnson DB. Management of V600E and V600K BRAF-mutant melanoma. Current treatment options in oncology. Nov. 2019;20:1-6. (Year: 2019).*

Zhang P, Feng S, Liu G, Wang H, Zhu H, Ren Q, Bai H, Fu C, Dong C. Mutant B-Raf (V600E) promotes melanoma paracellular transmigration by inducing thrombin-mediated endothelial junction breakdown. Journal of Biological Chemistry. Jan. 29, 2016;291(5): 2087-106. (Year: 2016).*

Xue YH, Zhang XF, Dong QZ, Sun J, Dai C, Zhou HJ, Ren N, Jia HL, Ye QH, Qin LX. Thrombin is a therapeutic target for metastatic osteopontin positive hepatocellular carcinoma. Hepatology. Dec. 2010;52(6):2012-22. (Year: 2010).*

Sturm RA. Osteopontin in Melanocytic Lesions A First Step Towards Invasion ?. Journal of Investigative Dermatology. May 1, 2005; 124(5):xiv-v. (Year: 2005).*

Schulze EB, Hedley BD, Goodale D, Postenka CO, Al-Katib W, Tuck AB, Chambers AF, Allan AL. The thrombin inhibitor Argatroban reduces breast cancer malignancy and metastasis via osteopontin-dependent and osteopontin-independent mechanisms. Breast cancer research and treatment. Nov. 2008;112(2):243-54. (Year: 2008).*

Leung et al., (2020) "Re-purposed combination therapies to improve outcomes in melanoma", Stanford OTL, pp. 1-3.

Peraramelli et al., (2017) "Thrombin cleavage of osteopontin plays an important role in melanoma growth and progression", International Society on Thrombo, 1(1):132.

Schulze et al., (2008) "The thrombin inhibitor Argatroban reduces breast cancer malignancy and metastasis via osteopontin-dependent and osteopontin-independent mechanisms", Breast Cancer Research and Treatment, 112 (2):243-254.

Strickland et al., (2015) "Targeting drivers of melanoma with synthetic small molecules and phytochemicals", Cancer Letters, 359:20-35.

Xue et al., (2010) "Thrombin is a therapeutic target for metastatic osteopontin-positive hepatocellular carcinoma", Hepatology, 52(6):2012-2022.

Esumi et al., (1991) "Inhibition of Murine Melanoma Experimental Metastasis by Recombinant Desulfatohirudin, a Highly Specific Thrombin Inhibitor", Cancer Research, 51:4549-4556.

Hayashi et al., (2007) "Serum Osteopontin, an Enhancer of Tumor Metastasis to Bone, Promotes B16 Melanoma Cell Migration", Journal of Cellular Biochemistry, 101:979-986.

Ishii, (2013) "Finally, the big cancer molecular target: MEK/RAF", Japanese Journal of Pharmacology, 141, pp. 15-21.

Ornstein et al., (2000) "Treatment of Cancer With Anticoagulants: Rationale in the Treatment of Melanoma", International Journal of Hematology, 73:175-161.

* cited by examiner

OPN-FL

NH$_2$ — [ //// | RGD | SVVYGL | RSKSKKFRR | //// ] — COOH

↑ DC Chemotaxis

↓ Thrombin

OPN-R

NH$_2$ — [ //// | RGD | SVVYGL | R ]

↑ Cell Adhesion

↓ DC Chemotaxis

↓ CPN
CPB2

OPN-CTF

[ SKSKKFRR | //// ] — COOH

↑ DC Chemotaxis

OPN-L

NH$_2$ — [ //// | RGD | SVVYGL ]

↓ Cell Adhesion

OPN-KI

FIG. 4G

Bone Marrow

Blood

OPN forms present
- OPN-FL
- OPN-R
- OPN-L
- CTF

OPN fragments modulate
TAM infiltration & composition

TAMs in tumor

Size of tumor on flank of metastatic nodules in lung

M1 macrophage
(CD38$^+$EGR-2$^-$):

M2 macrophage
(CD38$^-$EGR-2$^+$ or CD11b$^+$CD206$^+$):

Macrophage new phenotype
(CD11b$^+$CD11c$^-$CD206$^+$Ly-6G$^-$)

OPN KO

OPN KI

OPN-FL$_{R153A}$

No OPN fragments

No OPN fragments

Alkaline phosphatase

ALT

WBC lymphocytes platelets

RBC reticulocytes

Hgb

SEQUENCE LISTING

```
<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: NeoPCRF1 oligonucleotide
<220> FEATURE:
<221> NAME/KEY: source
<222> LOCATION: (1)..(28)
<223> OTHER INFORMATION: sequence is synthesized

<400> SEQUENCE: 1
ggtttccaaa tgtgtcagtt tcatagcc                                          28

<210> SEQ ID NO 2
<211> LENGTH: 28
<212> TYPE: DNA
<213> ORGANISM: Artificial Sequence
```

-continued

```
<220> FEATURE:
<223> OTHER INFORMATION: StanfordU2 3R oligonucleotide
<220> FEATURE:
<221> NAME/KEY: source
<222> LOCATION: (1)..(28)
<223> OTHER INFORMATION: sequence is synthesized

<400> SEQUENCE: 2
tctgaaacat agttccctaa gacatcag                                          28

<210> SEQ ID NO 3
<211> LENGTH: 25
<212> TYPE: DNA
<213> ORGANISM: Artificial Sequence
<220> FEATURE:
<223> OTHER INFORMATION: StanfordU2 5cko oligonucleotide
<220> FEATURE:
<221> NAME/KEY: source
<222> LOCATION: (1)..(25)
<223> OTHER INFORMATION: sequence is synthesized

<400> SEQUENCE: 3
atcatcaatg cttagccaag ccaag                                             25

<210> SEQ ID NO 4
<211> LENGTH: 7
<212> TYPE: PRT
<213> ORGANISM: Artificial Sequence
<220> FEATURE:
<223> OTHER INFORMATION: cryptic integrin-binding site

<400> SEQUENCE: 4

Ser Val Val Tyr Gly Leu Arg
1               5

<210> SEQ ID NO 5
<211> LENGTH: 18
<212> TYPE: PRT
<213> ORGANISM: Artificial Sequence
<220> FEATURE:
<223> OTHER INFORMATION: OPN-FL

<400> SEQUENCE: 5

Arg Gly Asp Ser Val Val Tyr Gly Leu Arg Ser Lys Ser Lys Lys Phe
1               5                   10                  15

Arg Arg

<210> SEQ ID NO 6
<211> LENGTH: 10
<212> TYPE: PRT
<213> ORGANISM: Artificial Sequence
<220> FEATURE:
<223> OTHER INFORMATION: OPN-R

<400> SEQUENCE: 6

Arg Gly Asp Ser Val Val Tyr Gly Leu Arg
1               5                   10

<210> SEQ ID NO 7
<211> LENGTH: 8
<212> TYPE: PRT
<213> ORGANISM: Artificial Sequence
<220> FEATURE:
<223> OTHER INFORMATION: OPN-CTF

<400> SEQUENCE: 7

Ser Lys Ser Lys Lys Phe Arg Arg
```

-continued

```
1               5

<210> SEQ ID NO 8
<211> LENGTH: 9
<212> TYPE: PRT
<213> ORGANISM: Artificial Sequence
<220> FEATURE:
<223> OTHER INFORMATION: OPN-L

<400> SEQUENCE: 8

Arg Gly Asp Ser Val Val Tyr Gly Leu
1               5
```

COMBINATION THERAPY FOR CANCER

STATEMENT REGARDING FEDERALLY SPONSORED RESEARCH OR DEVELOPMENT

This invention was made with Government support under contract HL057530 awarded by the National Institutes of Health. The Government has certain rights in the invention.

BACKGROUND

Cancer is a leading cause of death worldwide. Melanoma is the most aggressive form of skin cancer. If it is recognized and treated early it is almost always curable, but if it is not, the cancer can advance and spread to other parts of the body, where it becomes hard to treat and can be fatal. While it is not the most common of the skin cancers, it causes the most deaths. The standard treatment is surgery to remove the tumor and a surrounding area of normal-appearing skin. Sometimes surgery is followed by additional therapy such as immunotherapy, chemotherapy, radiation, or a combination of these treatments. Chemotherapy and immunotherapy are also used to treat advanced or recurrent melanoma. Patients would benefit from new therapies for melanoma as mortality and morbidity still occur even if patients are treated with the best current therapy.

Osteopontin (OPN), a widely expressed non-collagenous matricellular protein, is one of the 5% most highly expressed genes in 20 out of 35 cancer microarray data sets (Atai et al. (2011) Immunology 132, 39-48). OPN has been implicated in promoting invasive and metastatic progression of breast, lung and ovarian cancers, glioblastoma (GBM) and malignant melanoma (Chiodoni et al. (2010) Cancer Metastasis Rev 29, 295-307; Kothari et al. (2016) J. Clin. Med. 5(4):39; Lamort et al. (2019) Cells 8(8):815; McAllister et al. (2008) Cell 133, 994-1005; Shevde and Samant (2014) Journal of the International Society for Matrix Biology 37, 131-141; Zhao et al. (2018) Cell Death & Disease 9, 356). OPN expression levels correlate with tumor stage (Coppola et al. (2004) Clinical Cancer Research 10, 184-190), and increased OPN expression in primary melanoma is predictive of reduced relapse-free survival (Conway et al. (2009) Clinical cancer research 15, 6939-6946). Taken together, high levels of OPN is associated with more advanced cancer and a worse prognosis ((Lamort et al., supra).

In addition to being a bone matrix component, OPN is expressed by fibroblasts, hematopoietic and immune cells (Clemente et al. (2016) Journal of Immunology Research 2016, U.S. Pat. No. 7,675,437; Sodek et al. (2000) Crit. Rev. Oral Biol. Med. 11, 279-303) and its expression is markedly upregulated in inflammatory conditions such as cancer and infection (Lund et al. (2009) J. Cell Commun. Signal 3, 311-322; Uede (2011) Pathol. Int. 61, 265-280). When released, OPN has pleiotropic cytokine- and chemokine-like functions (Uede, supra; Wang and Denhardt (2008) Cytokine Growth Factor Rev 19, 333-345). It promotes leukocyte survival and differentiation, and regulates leukocyte adhesion, migration, and trafficking (Grassinger et al. (2009) Blood 114, 49-59; Lund et al. (2009) J. Cell Commun. Signal 3, 311-322; Sharif et al. (2009) Arthritis and Rheumatism 60, 2902-2912; Weiss et al. (2001) J. Exp. Med. 194, 1219-1229). It modulates IL-17 production and has been identified as a key player in some immune-mediated diseases (Rittling and Singh (2015) Journal of Dental Research 94, 1638-1645). OPN, either derived from the host and/or the cancer, may impact cell proliferation, survival, drug resistance, and stem-like behavior, and acts as a crucial mediator of cellular crosstalk in an autocrine and paracrine fashion in the tumor microenvironment (Lamort et al., supra; McAllister et al. (2008) Cell 133, 994-1005; Shevde and Samant (2014), supra). B16 murine melanoma cells are suppressed in mice deficient in OPN (OPN-KO, Spp$^{-/-}$) mice showing that tumor growth is dependent on the presence of OPN (Kale et al. (2014) Oncogene 33, 2295-2306; Kale et al. (2015) Oncogene 34, 5408-5410; Kumar et al. (2013) PLoS One 8, e69116; Nemoto et al., (2001) J. Bone Miner Res. 16, 652-659).

There remains a need for better methods of treating OPN-associated cancers such as melanoma.

SUMMARY

Methods for treating cancer using combination therapy with an anti-coagulant and a B-Raf inhibitor and/or a mitogen-activated protein kinase (MEK) inhibitor are disclosed. The anti-coagulant may be a direct inhibitor of thrombin or an indirect inhibitor of thrombin, such as an inhibitor of factor Xa, factor XIa, or other coagulation factors.

In one aspect, a method of treating an osteopontin (OPN)-associated cancer is provided, the method comprising administering to a subject in need thereof a therapeutically effective amount of an anti-coagulant in combination with a therapeutically effective amount of a B-Raf inhibitor and/or a therapeutically effective amount of a MEK inhibitor.

In certain embodiments, the methods described herein are used to treat melanoma. The melanoma can be, for example, B-RAF-mutated melanoma, including without limitation melanoma comprising a V600E mutation or a V600K mutation. In some embodiments, the melanoma is metastatic melanoma.

In certain embodiments, the anticoagulant is a direct thrombin inhibitor. Exemplary thrombin inhibitors include, without limitation, dabigatran, argatroban, inogatran, melagatran, ximelagatran, hirudin, bivalirudin, lepirudin, and desirudin.

In other embodiments, the anti-coagulant is an inhibitor of factor Xa. Exemplary inhibitors of factor Xa include, without limitation, rivaroxaban (Xarelto), apixaban (Eliquis), betrixaban, darexaban (YM150), edoxaban (Lixiana), otamixaban, letaxaban (TAK-442), eribaxaban, antistasin, warfarin, heparin, and fondaparinux.

In yet other embodiments, the anticoagulant is an inhibitor of factor XIa. Exemplary inhibitors of factor XIa include, without limitation, BMS-262084 ((2S,3R)-1-[4-(tert-butyl-carbamoyl)piperazine-1-carbonyl]-3-[3-(diaminomethylideneamino)propyl]-4-oxoazetidine-2-carboxylic acid), BMS-724296, BMS-654457 (2-[3-[(2S,4R)-6-carbamimidoyl-4-methyl-4-phenyl-2,3-dihydro-1H-quinolin-2-yl]-5-(3-methylbutanoylamino)phenyl]-5-carbamoylbenzoic acid), BMS-986177 ((9R,13S)-13-[4-[5-chloro-2-(4-chlorotriazol-1-yl)phenyl]-6-oxopyrimidin-1-yl]-3-(difluoromethyl)-9-methyl-3,4,7,15-tetrazatricyclo[12.3.1.02,6]octadeca-1(18), 2(6),4,14,16-pentaen-8-one), EP-7041 ((2S,3R)-3-([2-Aminopyridin-4-yl]methyl)-1-([{1  R}-1-cyclohexylethyl]carbamoyl)-4-oxoazetidine-2-carboxylic acid), ketoarginine-based peptidomimetic inhibitors, clavatadine inhibitors, aryl boronic acid inhibitors, and cyclic arginine-containing ketothiazole peptidomimetic inhibitors.

Exemplary B-Raf inhibitors include, without limitation, dabrafenib, vemurafenib, sorafenib, LGX818, GDC-0879, and PLX-4720.

Exemplary MEK inhibitors include, without limitation, trametinib, cobimetinib, binimetinib, selumetinib, and PD-325901.

In certain embodiments, the anti-coagulant, the B-Raf inhibitor, or the MEK inhibitor is administered according to a daily dosing regimen or intermittently.

Multiple cycles of treatment may be administered to the subject for a time period sufficient to effect at least a partial tumor response or more preferably a complete tumor response. In some embodiments, the time period is at least 6 months, 7 months, 8 months, 9 months, 10 months, 11 months, 12 months, 1.5 years, 2 years, or longer.

The anti-coagulant or the B-Raf inhibitor and/or MEK inhibitor and, optionally, other agents may be administered by any suitable mode of administration. In some embodiments, the anti-coagulant or the B-Raf inhibitor and/or MEK inhibitor are administered orally, intravenously, or topically.

In certain embodiments, the method further comprises administering an additional anti-cancer therapeutic agent. Exemplary anti-cancer therapeutic agents include, without limitation, chemotherapeutic agents, immunotherapeutic agents, biologic therapeutic agents, hormonal therapeutic agents, pro-apoptotic agents, angiogenesis inhibitors, photoactive agents, radiosensitizing agents, and radioisotopes.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A. Model of OPN cleavages and its functional modulation by thrombin and carboxypeptidase N or B2. OPN-FL=OPN-full length (SEQ ID NO:5); OPN-R=OPN-Arg (SEQ ID NO:6); OPN-L=OPN-Leu (SEQ ID NO:8). DC=dendritic cells. FIG. 1B. Time course of thrombin treatment (10 nM) of _E. coli_ produced GST-OPN and GST-OPN$_{R153A}$ analyzed by SDS-PAGE. FL=full length, NTF=N-terminal fragment, CTF=C-terminal fragment (SEQ ID NO:7). FIG. 1C. Daily determination of B16 tumor volume grown on WT, OPN-KI and OPN-KO mice. FIG. 1D. B16 tumor weight after sacrifice. All data are shown as mean±SEM. Statistical significance was calculated by one-way ANOVA followed by Tukey's multiple comparison test.

FIGS. 2A-2C: B16 tumors have lower tumor burden in OPN-KO and OPN-KI than WT mice in the metastasis model. FIG. 2A. Lungs from mice sacrificed 13 days after tumor injection i.v. FIG. 2B. Number of visible metastatic lung nodules. FIG. 2C. Melanin content of lungs. All data are shown as mean±SEM. Statistical significance was calculated by one-way ANOVA followed by Tukey's multiple comparison test.

FIG. 3A. Daily determination of B16 tumor growth implanted on the flank of WT mice either fed on DE-containing chow (open symbols) or control chow (closed symbols). FIG. 3B. B16 tumor weights after sacrifice in OPN-KI mice either on DE-containing chow (open symbols) or control chow (closed symbols). FIG. 3C. B16 tumor volumes after sacrifice. FIG. 3D. B16 tumor weights after sacrifice. FIG. 3E. aPTT determined from blood collected at the time of sacrifice. In FIGS. 3A-3E, data are shown as mean±SEM. Statistical significance was calculated by Student's t-test comparing each genotype with and without DE in the chow. FIG. 3F. Correlation of aPTT prolongation and tumor weights in WT mice treated with DE. FIG. 3G. Number of visible nodules counted in the lungs of mice sacrificed 13 days after inoculation in WT and OPN-KI mice fed either DE or control chow in the metastasis model. FIG. 3H. Melanin content of lungs at 13 days after inoculation. In FIGS. 3G and 3H, data are shown as mean±SEM. Statistical significance was calculated by one-way ANOVA followed by Tukey's multiple comparison test.

FIGS. 4A-4G: OPN cleavage products can be detected in tumors and plasma in WT mice and their effects on B16 cells. OPN-FL, OPN-R and OPN-L were assayed by ELISA in plasma from mice before tumor implantation (FIG. 4A), after sacrifice (FIG. 4B) and in tumor lysates (FIG. 4C). The effects of OPN fragments on B16 cell adhesion (FIG. 4D), growth (FIG. 4E), migration (FIG. 4F) and apoptosis (FIG. 4G) were determined. Data are shown as mean±SEM. Statistical significance was calculated by one-way ANOVA followed by Tukey's multiple comparison test. OPN-FL=OPN full length, OPN-R=OPN-Arg, OPN-L=OPN-Leu, OPN-CTF=OPN-C-terminal fragment. Subscript RAA denotes substitution of the RGD sequence by RAA in that OPN fragment.

FIG. 5A. H&E staining of tumor sections from WT, OPN-KI and OPN-KO mice. FIG. 5B. Tumor sections from WT, OPN-KI and OPN-KO mice stained with anti-F4/80 antibody. FIG. 5C. Tumor sections from WT, OPN-KI and OPN-KO mice stained with anti-CD3 antibody FIG. 5D. The percentage of F4/80+ cells present in tumors from OPN-KI, OPN-KO and WT mice determined by flow cytometry. All data are shown as mean±SEM. Statistical significance was calculated by one-way ANOVA followed by Tukey's multiple comparison test.

FIG. 6A. WT mice were treated with either clodronate (open symbols) or control (closed symbols) liposomes and the tumor volumes measured after sacrifice. FIG. 6B. OPN-KI mice were treated with either clodronate or control liposomes and the tumor volumes measured after sacrifice FIG. 6C. WT or OPN-KI mice were treated with either clodronate or control liposomes and the tumor weights measured after sacrifice. FIG. 6D. WT or OPN-KI mice were treated with either clodronate or control liposomes and the tumor weights measured after sacrifice. FIG. 6E. The percentage of F4/80+ cells was determined in the bone marrow from WT or OPN-KI mice treated with either clodronate or control liposomes 14 days after inoculation with B16 cells. FIG. 6F. The percentage of F4/80+ cells was determined in the tumors from WT or OPN-KI mice treated with either clodronate or control liposomes. FIG. 6G. The percentage of F4/80+ cells was determined in blood from WT or OPN-KI mice treated with either clodronate or control liposomes 14 days after inoculation with B16 cells. All data are shown as mean±SEM. Statistical significance was calculated by one-way ANOVA followed by Tukey's multiple comparison test.

FIG. 7A. Daily determination of B16 tumor volume grown on NOG-WT (blue circles), NOG-OPN-KI (green triangles) and NOG-OPN-KO (red squares) mice in the flank model. FIG. 7B. B16 tumor weights after sacrifice in NOG-WT, NOG-OPN-KI and NOG-OPN-KO mice in the flank model. FIG. 7C. Number of visible metastatic lung nodules counted in the lungs of mice sacrificed 13 days after tumor injection i.v. FIG. 7D. Melanin content of lungs. All data are shown as mean±SEM. Statistical significance was calculated by one-way ANOVA followed by Tukey's multiple comparison test.

FIGS. 8A-8J: Changes in macrophages in tumors from OPN-KI and OPN-KO mice compared to WT mice. Infiltrating macrophages (FIG. 8A), M1 macrophages (FIG. 8B), M2 macrophages (FIGS. 8C and 8D), Macrophages with new phenotype (FIG. 8E), neutrophils (FIG. 8F), B-cells (FIG. 8G) and T-cells (FIG. 8H) were determined by flow cytometry in tumor samples from the flank model in WT, OPN-KI and OPN-KO mice. All data are shown as mean±SEM. Statistical significance was calculated by one-way ANOVA followed by Tukey's multiple comparison test. Production of $PGE_2$ by RAW cells in response to OPN fragments (FIG. 8I). Data are shown as mean±SEM. Statistical significance was calculated by one-way ANOVA followed by Tukey's post-hoc test. : $p<0.01$ vs. OPN-R, *: $p<0.001$ vs. OPN-R, **: $p<0.001$ vs. OPN-R, +: $p<0.05$ vs. OPN-$R_{RAA}$. Subscript RAA denotes substitution of the RGD sequence by RAA in that OPN fragment. Model of thrombin+/−CPN/CPB2 cleavage(s) of OPN and their effect on macrophages, tumor growth and metastasis. (FIG. 8J**). Cleaved OPN fragments affect the infiltration and composition of macrophages in the tumor maintaining tumor-promoting M2 macrophages (green cells) in WT mice. These OPN fragments are absent in either OPN KO or thrombin-resistant OPN-KI mice, leading to decrease in M2 macrophages and replacement by macrophages with a different activation phenotype (red cells) leading to tumor suppression.

FIG. 9H) and total bilirubin (FIG. 9I) in plasma from WT, OPN-KI and OPN-KO mice. Data analyzed by ANOVA followed by Bonferroni post hoc test and showed no differences between groups.

FIG. 10H). Data analyzed by ANOVA followed by Bonferroni post hoc test and showed no differences between groups.

(FIG. 11A) $2×10^6$ cells, (FIG. 11B) $1×10^6$ cells, (FIG. 11C) $0.5×10^6$ cells, (FIG. 11D) Weight of B16 tumors after sacrifice in male (solid symbols) and female (open symbols) WT (blue circles) and OPN-KI (green triangles) mice. Data analyzed by ANOVA followed by Tukey post hoc test and showed no differences between groups.

FIG. 17A. Map of recombinant allele showing locations of primers FIG. 17B. Mice homozygous for the mutated R153A gene (light gray lettering) were identified by PCR screening.

DETAILED DESCRIPTION OF EMBODIMENTS

Figure 1A:
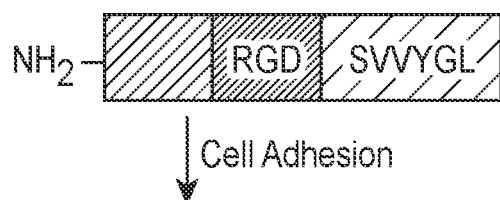
FIGS. 1A-1D: B16 tumors grow slower in OPN-KO and OPN-KI than WT mice in the flank model.

Methods for treating cancer using combination therapy with an anti-coagulant and a B-Raf inhibitor and/or a MEK inhibitor are disclosed. The anti-coagulant may be a direct inhibitor of thrombin or an indirect inhibitor of thrombin, such as an inhibitor of factor Xa, factor XIa, or other coagulation factors.

Before the methods for treating cancer using combination therapy with an anti-coagulant and a B-Raf inhibitor and/or MEK inhibitor are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "an inhibitor" includes a plurality of such inhibitors and reference to "the cancerous cell" includes reference to one or more cancerous cells and equivalents thereof, such as cancer cells, tumor cells, neoplastic cells, and malignant cells, known to those skilled in the art, and so forth.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "B-Raf inhibitor" as used herein refers to any molecule (e.g., small molecule inhibitor, protein, peptide, peptidomimetic, nucleic acid, oligonucleotide, antibody, or fragment thereof) that inhibits B-Raf activity and/or B-Raf expression. Inhibition may be complete or partial (i.e., all activity, some activity, or most activity is blocked by an inhibitor). B-Raf inhibitors include, but are not limited to, an anti-B-Raf antibody, a B-Raf serine/threonine protein kinase inhibitor, an antisense inhibitor of B-Raf expression, an anti-B-Raf ribozyme, an anti-B-Raf siRNA, and an endogenous B-Raf inhibitor. Exemplary B-Raf inhibitors include, without limitation, dabrafenib, vemurafenib, sorafenib, LGX818, GDC-0879, and PLX-4720.

The term "MEK inhibitor" as used herein refers to any molecule (e.g., small molecule inhibitor, protein, peptide, peptidomimetic, nucleic acid, oligonucleotide, antibody, or fragment thereof) that inhibits MEK activity and/or MEK expression. Inhibition may be complete or partial (i.e., all activity, some activity, or most activity is blocked by an inhibitor). MEK inhibitors include, but are not limited to, an anti-MEK antibody, a MEK serine/threonine protein kinase inhibitor, an antisense inhibitor of MEK expression, an anti-MEK ribozyme, an anti-MEK siRNA, and an endogenous MEK inhibitor. Exemplary MEK inhibitors include, without limitation, trametinib, cobimetinib, binimetinib, selumetinib, and PD-325901.

The term "thrombin inhibitor" as used herein refers to any molecule (e.g., small molecule inhibitor, protein, peptide, peptidomimetic, nucleic acid, oligonucleotide, antibody, or fragment thereof) that inhibits thrombin activity and/or thrombin expression. Inhibition may be complete or partial (i.e., all activity, some activity, or most activity is blocked by an inhibitor). Thrombin inhibitors include, but are not limited to, an anti-thrombin antibody, an antisense inhibitor of thrombin expression, an anti-thrombin ribozyme, an anti-thrombin siRNA, and an endogenous thrombin inhibitor. Exemplary thrombin inhibitors include, without limitation, dabigatran, argatroban, inogatran, melagatran, ximelagatran, hirudin, bivalirudin, lepirudin, and desirudin.

The term "factor Xa inhibitor" as used herein refers to any molecule (e.g., small molecule inhibitor, protein, peptide, peptidomimetic, nucleic acid, oligonucleotide, antibody, or fragment thereof) that inhibits factor Xa activity and/or factor Xa expression. Inhibition may be complete or partial (i.e., all activity, some activity, or most activity is blocked by an inhibitor). Factor Xa inhibitors include, but are not limited to, an anti-factor Xa antibody, an antisense inhibitor of factor Xa expression, an anti-factor Xa ribozyme, an anti-factor Xa siRNA, and an endogenous factor Xa inhibitor. Exemplary factor Xa inhibitors include, without limitation, rivaroxaban (Xarelto), apixaban (Eliquis), betrixaban, darexaban (YM150), edoxaban (Lixiana), otamixaban, letaxaban (TAK-442), eribaxaban, antistasin, warfarin, heparin, and fondaparinux.

The term "factor XIa inhibitor" as used herein refers to any molecule (e.g., small molecule inhibitor, protein, peptide, peptidomimetic, nucleic acid, oligonucleotide, antibody, or fragment thereof) that inhibits factor XIa activity and/or factor XIa expression. Inhibition may be complete or partial (i.e., all activity, some activity, or most activity is blocked by an inhibitor). Factor XIa inhibitors include, but are not limited to, an anti-factor XIa antibody, an antisense inhibitor of factor XIa expression, an anti-factor XIa ribozyme, an anti-factor XIa siRNA, and an endogenous factor XIa inhibitor. Exemplary factor XIa inhibitors include, without limitation, BMS-262084 ((2S,3R)-1-[4-(tert-butylcarbamoyl)piperazine-1-carbonyl]-3-[3-(di-aminomethylideneamino)propyl]-4-oxoazetidine-2-carboxylic acid), BMS-724296, BMS-654457 (2-[3-[(2S,4R)-6-carbamimidoyl-4-methyl-4-phenyl-2,3-dihydro-1H-quinolin-2-yl]-5-(3-methylbutanoylamino)phenyl]-5-carbamoylbenzoic acid), BMS-986177 ((9R,13S)-13-[4-[5-chloro-2-(4-chlorotriazol-1-yl)phenyl]-6-oxopyrimidin-1-yl]-3-(difluoromethyl)-9-methyl-3,4,7,15-tetrazatricyclo [12.3.1.02,6]octadeca-1(18),2(6),4,14,16-pentaen-8-one), EP-7041 ((2S,3R)-3-([2-Aminopyridin-4-yl]methyl)-1-([{1R}-1-cyclohexylethyl]carbamoyl)-4-oxoazetidine-2-carboxylic acid), ketoarginine-based peptidomimetic inhibitors, clavatadine, aryl boronic acid inhibitors, and cyclic arginine-containing ketothiazole peptidomimetic inhibitors. For a further description of factor XIa inhibitors, see, e.g., Rami et al. (2016) Expert Opin. Ther. Pat. 26(3): 323-345, Quan et al. (2018) J. Med. Chem. 61, 17:7425-7447, Wong et al. (2021) Res. Pract. Thromb. Haemost. 5(4):e12524, Wong et al. (2015) J Thromb Thrombolysis 40(4):416-23, and Gómez-Outes et al. (2011) Ther. Adv. Cardiovasc. Dis. 5(1):33-59; herein incorporated by reference.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer) as well as those in which prevention is desired (e.g., those with increased susceptibility to cancer due to a genetic predisposition to developing cancer, those suspected of having an environmental exposure to a carcinogen, those with a risk of recurrence, etc.).

The terms "tumor," "cancer" and "neoplasia" are used interchangeably and refer to a cell or population of cells whose growth, proliferation or survival is greater than growth, proliferation or survival of a normal counterpart cell, e.g., a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma, and include cancers such as, but are not limited to, head and neck cancer, skin cancer, breast cancer, ovarian cancer, melanoma, pancreatic cancer, peripheral neuroma, glioblastoma, adrenocortical carcinoma, AIDS-related lymphoma, anal cancer, bladder cancer, meningioma, glioma, astrocytoma, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilm's tumor and other childhood kidney tumors.

In particular, the term "melanoma" includes, any type of melanoma at any stage, including metastatic melanoma. For example, the term "melanoma" includes, without limitation, lentigo maligna, lentigo maligna melanoma, superficial spreading melanoma, acral lentiginous melanoma, mucosal melanoma, nodular melanoma, polypoid melanoma, and desmoplastic melanoma. Melanomas may contain changes (mutations) in their genomic DNA sequence that mean that the proteins encoded by a melanoma cell differ from those elsewhere in the patient's body. As an example, the protein, B-RAF, which is involved in signaling growth to the cell, can have mutations. Thus, the term also includes B-RAF-mutated melanoma, including without limitation, melanoma comprising a V600E mutation or a V600K mutation.

The term "OPN-associated cancer" as used herein refers to any cancer associated with overexpression of osteopontin or hyperactivity of osteopontin or dependent on cleavage fragments of osteopontin. OPN-associated cancers include, but are not limited to, melanoma, breast cancer, lung cancer (e.g., lung adenocarcinoma, lung squamous-cell carcinoma, non-small cell lung cancer), ovarian cancer, glioblastoma, pheochromocytoma, paraganglioma, bladder cancer, cervical cancer, esophageal cancer, gastric cancer, head and neck cancer, kidney cancer (e.g., renal cancer, renal papillary cell cancer), hepatic cancer, pancreatic cancer (e.g., pancreatic ductal cancer), prostate cancer, rectal cancer (e.g., colorectal adenocarcinoma), sarcoma, testicular germ cell cancer, thymoma, thyroid cancer, and uterine cancer.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

By "therapeutically effective dose or amount" of an anti-coagulant (e.g., inhibitor of thrombin, factor Xa, factor XIa, or other coagulation factor), B-Raf inhibitor, or MEK inhibitor is intended an amount that, when the anti-coagulant and the B-Raf inhibitor and/or MEK inhibitor are administered in combination, as described herein, brings about a positive therapeutic response, such as anti-tumor activity.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions.

"Substantially purified" generally refers to isolation of a substance (antibody, compound, drug, polynucleotide, protein, polypeptide) such that the substance comprises the majority percent of the sample in which it resides. Typically in a sample, a substantially purified component comprises 50%, preferably 80%-85%, more preferably 90-95% of the sample. Techniques for purifying substances of interest are well-known in the art and include, for example, ion-exchange chromatography, affinity chromatography and sedimentation according to density.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Combination Therapy for Treatment of Cancer

The present invention is based on the discovery of a novel therapeutic methodology for treating OPN-associated cancers. The methods utilize delivery of an anti-coagulant (i.e., a direct or indirect thrombin inhibitor) in combination with a B-Raf inhibitor and/or a MEK inhibitor. Without being bound by a particular theory, OPN has been implicated in promoting invasive and metastatic progression of many types of cancer. Overexpression of OPN is associated with cancer progression and poor prognosis. Thrombin cleaves OPN in vivo to regulate OPN function. Thrombin cleavage fragments of OPN have a significant pathophysiological impact on cancer biology with effects on tumor cell adhesion, chemotaxis, and apoptosis as well as the host-anti-tumor immune response (see Example 1). Elevated levels of OPN cleavage fragments promote tumor growth and metastases. Therefore, an anti-coagulant (i.e., a direct or indirect thrombin inhibitor) can be used for treating an OPN-associated cancer.

Currently, some OPN-associated cancers are treated with a B-Raf inhibitor and/or a MEK inhibitor. Adding a direct or indirect thrombin inhibitor to the treatment of an OPN-associated cancer may improve outcomes. Accordingly, combination therapy with an anti-coagulant and a B-Raf inhibitor and/or a MEK inhibitor can be used to treat various types of cancer in which OPN is dysregulated.

Examples of anticoagulants that can be used in treatment of an OPN-associated cancer include, but are not limited to, thrombin inhibitors including, without limitation, dabigatran, argatroban, inogatran, melagatran, ximelagatran, hirudin, bivalirudin, lepirudin, and desirudin; inhibitors of factor Xa, including, without limitation, rivaroxaban (Xarelto), apixaban (Eliquis), betrixaban, darexaban (YM150), edoxaban (Lixiana), otamixaban, letaxaban (TAK-442), eribaxaban, antistasin, warfarin, heparin, and fondaparinux; and inhibitors of factor XIa, including, without limitation, BMS-262084 ((2S,3R)-1-[4-(tert-butylcarbamoyl)piperazine-1-carbonyl]-3-[3-(diaminomethylideneamino)propyl]-4-oxoazetidine-2-carboxylic acid), BMS-724296, BMS-654457 (2-[3-[(2S,4R)-6-carbamimidoyl-4-methyl-4-phenyl-2,3-dihydro-1H-quinolin-2-yl]-5-(3-methylbutanoylamino)phenyl]-5-carbamoylbenzoic acid), BMS-986177 ((9R,13S)-13-[4-[5-chloro-2-(4-chlorotriazol-1-yl)phenyl]-6-oxopyrimidin-1-yl]-3-(difluoromethyl)-9-methyl-3,4,7,15-tetrazatricyclo[12.3.1.02,6]octadeca-1(18), 2(6),4,14,16-pentaen-8-one), EP-7041 ((2S,3R)-3-([2-Aminopyridin-4-yl]methyl)-1-([{1 R}-1-cyclohexylethyl]carbamoyl)-4-oxoazetidine-2-carboxylic acid), ketoarginine-based peptidomimetic inhibitors, clavatadine inhibitors, aryl boronic acid inhibitors, and cyclic arginine-containing ketothiazole peptidomimetic inhibitors.

Examples of B-Raf inhibitors that can be used in treatment of an OPN-associated cancer include, but are not limited to, dabrafenib, vemurafenib, sorafenib, LGX818, GDC-0879, and PLX-4720.

Examples of MEK inhibitors that can be used in treatment of an OPN-associated cancer include, but are not limited to, trametinib, cobimetinib, binimetinib, selumetinib, and PD-325901.

While the methods of the invention are directed to treatment of an existing tumor, it is recognized that the methods may be useful in preventing further tumor outgrowths arising during therapy and metastasis.

Pharmaceutical Compositions

An anticoagulant, B-Raf inhibitor, and MEK inhibitor can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the anticoagulant, B-Raf inhibitor, and MEK inhibitor or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the anticoagulant, B-Raf inhibitor, or MEK inhibitor (e.g., when contained in a drug delivery system) in a composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising an anticoagulant, B-Raf inhibitor, and/or MEK inhibitor described herein are in unit dosage form, meaning an amount of a conjugate or composition appropriate for a single dose, in a premeasured or pre-packaged form.

The compositions herein may optionally include one or more additional agents, such as other drugs for treating cancer or other medications used to treat a subject for a condition or disease. Compounded preparations may include an anticoagulant, B-Raf inhibitor, and/or MEK inhibitor, and one or more other drugs for treating cancer, such as, but not limited to, chemotherapeutic agents, immunotherapeutic agents, biologic therapeutic agents, pro-apoptotic agents, angiogenesis inhibitors, photoactive agents, radiosensitizing drugs, and radioisotopes. Alternatively, such agents can be contained in a separate composition from the composition(s) comprising the anticoagulant, B-Raf inhibitor, and/or MEK inhibitor and co-administered concurrently, before, or after the composition(s) comprising the anticoagulant, B-Raf inhibitor, and/or MEK inhibitor.

Administration

At least one therapeutically effective dose of an anticoagulant and a B-Raf inhibitor and/or a mitogen-activated protein kinase (MEK) inhibitor will be administered. By "therapeutically effective dose or amount" of each of these agents is intended an amount that when administered in combination with the other agents, brings about a positive therapeutic response with respect to treatment of an individual for cancer, particularly an OPN-associated cancer.

OPN-associated cancers include, but are not limited to, melanoma, breast cancer, lung cancer (e.g., lung adenocarcinoma, lung squamous-cell carcinoma, non-small cell lung cancer), ovarian cancer, glioblastoma, pheochromocytoma, paraganglioma, bladder cancer, cervical cancer, esophageal cancer, gastric cancer, head and neck cancer, kidney cancer (e.g., renal cancer, renal papillary cell cancer), hepatic cancer, pancreatic cancer (e.g., pancreatic ductal cancer), prostate cancer, rectal cancer (e.g., colorectal adenocarcinoma), sarcoma, testicular germ cell cancer, thymoma, thyroid cancer, and uterine cancer.

Of particular interest is an amount of these agents that provides an anti-tumor effect, as defined herein. By "positive therapeutic response" is intended the individual undergoing the combination treatment according to the invention exhibits an improvement in one or more symptoms of the cancer for which the individual is undergoing therapy. Thus, for example, a "positive therapeutic response" would be an improvement in the disease in association with the combination therapy, and/or an improvement in one or more symptoms of the disease in association with the combination therapy. Therefore, for example, a positive therapeutic response would refer to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements (for patients with evaluable response only, partial response does not apply).

In certain embodiments, multiple therapeutically effective doses of each of the anti-coagulant and the B-Raf inhibitor and/or MEK inhibitor will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, the anti-coagulant and the B-Raf inhibitor and/or MEK inhibitor will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

The anti-coagulant can be administered prior to, concurrent with, or subsequent to the B-Raf inhibitor and/or MEK inhibitor. If provided at the same time as the B-Raf inhibitor and/or MEK inhibitor, the anti-coagulant can be provided in the same or in a different composition. Thus, the three agents or two of the three agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising the anti-coagulant and at least one therapeutically effective dose of a pharmaceutical composition comprising at least one B-Raf inhibitor and/or MEK inhibitor according to a particular dosing regimen. Similarly, the B-Raf inhibitor or MEK inhibitor can be administered in at least one therapeutic dose in the same pharmaceutical composition containing the anticoagulant or in separate pharmaceutical compositions. Administration of the separate pharmaceutical compositions can be at the same time (i.e., simultaneously) or at different times (i.e., sequentially, in either order, on the same day, or on different days), so long as the therapeutic effect of the combination of these substances is caused in the subject undergoing therapy.

In certain embodiments, the anti-coagulant is administered for a brief period prior to administration of the B-Raf inhibitor and/or MEK inhibitor and continued for a brief period after treatment with the B-Raf inhibitor and/or MEK inhibitor is discontinued in order to ensure that anticoagulant levels are adequate in the subject during therapy with the B-Raf inhibitor and/or MEK inhibitor. For example, the anticoagulant can be administered starting one week before administration of the first dose of the B-Raf inhibitor and/or MEK inhibitor and continued for one week after administration of the last dose of the B-Raf inhibitor and/or MEK inhibitor to the subject.

In other embodiments, the pharmaceutical compositions comprising the agents, such as the anti-coagulant, B-Raf inhibitor, and/or MEK inhibitor are sustained-release formulations, or formulations that are administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising the anti-coagulant, B-Raf inhibitor, and/or MEK inhibitor may be administered using the same or different routes of administration in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent, such as the anti-coagulant and the B-Raf inhibitor and/or MEK inhibitor in the bloodstream, is equivalent to that obtained with a therapeutically effective dose that is administered parenterally, for example SC, IP, IM, or IV. In some embodiments, the pharmaceutical composition comprising the anti-coagulant and the B-Raf inhibitor and/or MEK inhibitor is administered by IM or SC injection, particularly by IM or SC injection locally to the region where the therapeutic agent or agents used in the cancer therapy protocol are administered. In some cases, compositions may be administered directly into a tumor or cancerous cells. Administration may be by perfusion through a regional catheter or direct intralesional injection. In the case of melanoma, the anti-coagulant and the B-Raf inhibitor and/or MEK inhibitor may be administered topically, for example, on a patch or in a gel or ointment.

In another embodiment, the pharmaceutical compositions comprising the anti-coagulant, B-Raf inhibitor, and/or MEK inhibitor are administered prophylactically, e.g., to prevent cancer progression or metastasis in tissue. Such prophylactic uses will be of particular value for subjects at high risk of developing cancer due to an environmental exposure to a carcinogen or a genetic predisposition to developing cancer.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this agent is preferred with increasing weight of the subject undergoing therapy.

In certain embodiments, the method of treatment of a patient having cancer comprises a treatment cycle with the anti-coagulant in combination with the B-Raf inhibitor and/or MEK inhibitor followed by a rest period in which no anti-coagulant, B-Raf inhibitor, or MEK inhibitor is administered to allow the patient to "recover" from the undesirable effects of the agents. Multiple doses of the anti-coagulant in combination with the B-Raf inhibitor and/or MEK inhibitor can be administered according to a daily dosing regimen or intermittently, followed by a rest period. For example, the rest period between dosing regimens may be 1 day, 2 days, 3 days, 4 days, 5 days, 6 days, 1 week, 2 weeks, 3 weeks, or 4 weeks or longer or any period in between. Thereafter, a new schedule of dosing may be administered to achieve the desired combination effect.

Where a subject undergoing therapy in accordance with the previously mentioned dosing regimens exhibits a partial response, or a relapse following a prolonged period of remission, subsequent courses of concurrent therapy may be needed to achieve complete remission of the disease. Thus, subsequent to a period of time off from a first treatment period, a subject may receive one or more additional treatment periods comprising anticoagulant therapy in combination with a B-Raf inhibitor and/or MEK inhibitor. Such a period of time off between treatment periods is referred to herein as a time period of discontinuance. It is recognized that the length of the time period of discontinuance is dependent upon the degree of tumor response (i.e., complete versus partial) achieved with any prior treatment periods of concurrent therapy with these therapeutic agents.

Additionally, treatment with an anticoagulant and a B-Raf inhibitor and/or MEK inhibitor may be combined with any other medical treatment for cancer, such as, but not limited to, surgery, radiation therapy, chemotherapy, hormonal therapy, immunotherapy, or molecularly targeted or biologic therapy. Any combination of these other medical treatment methods with an anticoagulant in combination with a B-Raf inhibitor and/or MEK inhibitor may be used to effectively treat cancer in a subject.

For example, treatment with an anticoagulant in combination with a B-Raf inhibitor and/or MEK inhibitor may be combined with chemotherapy with one or more chemotherapeutic agents such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dacarbazine, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

In another example, treatment with an anticoagulant in combination with a B-Raf inhibitor and/or MEK inhibitor may be combined with targeted therapy with one or more small molecule inhibitors or monoclonal antibodies such as, but not limited to, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax and gossypol; PARP inhibitors, such as Iniparib and Olaparib; PI3K inhibitors, such as perifosine; VEGF receptor 2 inhibitors, such as Apatinib; AN-152 (AEZS-108) doxorubicin linked to [D-Lys(6)]-LHRH; CDK inhibitors, such as PD-0332991 and LEE011; Hsp90 inhibitors, such as salinomycin; small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar); C-Kit inhibitors, such as imatinib, dasatinib and nilotinib; NRAS inhibitors, such as binimetinib; and monoclonal antibodies, such as Rituximab (marketed as MabThera or Rituxan), Trastuzumab (Herceptin), Alemtuzumab, Cetuximab (marketed as Erbitux), Panitumumab, Bevacizumab (marketed as Avastin), and Ipilimumab (Yervoy).

In a further example, treatment with an anticoagulant in combination with a B-Raf inhibitor and/or MEK inhibitor may be combined with immunotherapy, including, but not limited to, using any of the following: a cancer vaccine (e.g., E75 HER2-derived peptide vaccine, nelipepimut-S(Neu-Vax), Sipuleucel-T), antibody therapy (e.g., Trastuzumab, Ado-trastuzumab emtansine, Alemtuzumab, Ipilimumab, Ofatumumab, Nivolumab, Pembrolizumab, or Rituximab), cytokine therapy (e.g., interferons, including type I (IFNα and IFNβ), type II (IFNγ) and type III (IFNλ) and interleukins, including interleukin-2 (IL-2)), adjuvant immunochemotherapy (e.g., polysaccharide-K), adoptive T-cell therapy, oncolytic virus therapy, and immune checkpoint blockade therapy (e.g., ipilimumab, pembrolizumab, nivolumab).

In a further example, treatment with an anticoagulant in combination with a B-Raf inhibitor and/or MEK inhibitor may be combined with radiation therapy with a radioisotope, including, but not limited to, iodine-131, strontium-89, samarium-153, and radium-223. In addition, radiation therapy may be combined with administration of a radiosensitizing drug such as, but not limited to, Cisplatin, Nimorazole, and Cetuximab.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-21 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of treating an osteopontin (OPN)-associated cancer, the method comprising administering to a subject in need thereof a therapeutically effective amount of an anti-coagulant in combination with a therapeutically effective amount of a B-Raf inhibitor or a mitogen-activated protein kinase (MEK) inhibitor.

2. The method of aspect 1, wherein the anticoagulant is a direct thrombin inhibitor.

3. The method of aspect 2, wherein the thrombin inhibitor is selected from the group consisting of dabigatran, argatroban, inogatran, melagatran, ximelagatran, hirudin, bivalirudin, lepirudin, and desirudin.

4. The method of any of one of aspects 1 to 3, wherein the B-Raf inhibitor is selected from the group consisting of dabrafenib, vemurafenib, sorafenib, LGX818, GDC-0879, and PLX-4720.

5. The method of any one of aspects 1 to 4, wherein the anti-coagulant is administered in combination with a therapeutically effective amount of the B-Raf inhibitor and a therapeutically effective amount of the MEK inhibitor.

6. The method of any one of aspects 1 to 5, wherein the MEK inhibitor is selected from the group consisting of trametinib, cobimetinib, binimetinib, selumetinib, and PD-325901.

7. The method of any one of aspects 1 to 6, wherein the anti-coagulant, the B-Raf inhibitor, or the MEK inhibitor is administered according to a daily dosing regimen or intermittently.

8. The method of any one of aspects 1 to 7, wherein multiple cycles of treatment are administered to the subject for a time period sufficient to effect at least a partial tumor response.

9. The method of aspect 8, wherein the time period is at least 6 months.

10. The method of aspect 9, wherein the time period is at least 12 months.

11. The method of any one of aspects 8 to 10, wherein a complete tumor response is effected.

12. The method of any one of aspects 1 to 11, wherein the anti-coagulant or the B-Raf inhibitor is administered orally, intravenously, or topically.

13. The method of any one of aspects 1 to 12, wherein the OPN-associated cancer is melanoma.

14. The method of aspect 13, wherein the melanoma is a B-RAF-mutated melanoma.

15. The method of aspect 14, wherein the B-RAF-mutated melanoma comprises a V600E mutation or a V600K mutation.

16. The method of any one of aspects 13 to 15, wherein the melanoma is metastatic.

17. The method of any one of aspects 1 to 16, wherein the subject is human.

18. The method of any one of aspects 1 to 17, wherein the anti-coagulant is an inhibitor of factor Xa.

19. The method of aspect 18, wherein the inhibitor of factor Xa is selected from the group consisting of rivaroxaban (Xarelto), apixaban (Eliquis), betrixaban, darexaban (YM150), edoxaban (Lixiana), otamixaban, letaxaban (TAK-442), eribaxaban, antistasin, warfarin, heparin, and fondaparinux.

20. The method of any one of aspects 1 to 17, wherein the anti-coagulant is an inhibitor of factor XIa.

21. The method of aspect 20, wherein the inhibitor of factor XIa is selected from the group consisting of BMS-262084 ((2S,3R)-1-[4-(tert-butylcarbamoyl)piperazine-1-carbonyl]-3-[3-(diaminomethylideneamino) propyl]-4-oxoazetidine-2-carboxylic acid), BMS-724296, BMS-654457 (2-[3-[(2S,4R)-6-carbamimidoyl-4-methyl-4-phenyl-2,3-dihydro-1H-quinolin-2-yl]-5-(3-methylbutanoylamino)phenyl]-5-carbamoylbenzoic acid), BMS-986177 ((9R,13S)-13-[4-[5-chloro-2-(4-chlorotriazol-1-yl)phenyl]-6-oxopyrimidin-1-yl]-3-(difluoromethyl)-9-methyl-3,4, 7,15-tetrazatricyclo[12.3.1.02,6]octadeca-1(18),2(6),4, 14,16-pentaen-8-one), EP-7041 ((2S,3R)-3-([2-Aminopyridin-4-yl]methyl)-1-([{1 R}-1-cyclohexylethyl]carbamoyl)-4-oxoazetidine-2-carboxylic acid), a ketoarginine-based peptidomimetic, a clavatadine, an aryl boronic acid, and a cyclic arginine-containing ketothiazole peptidomimetic.

22. The method of any one of aspects 1 to 21, further comprising administering an additional anti-cancer therapeutic agent.

23. The method of aspect 22, wherein the additional anti-cancer therapeutic agent is a chemotherapeutic agent, an immunotherapeutic agent, a biologic therapeutic agent, a hormonal therapeutic agent, a pro-apoptotic agent, an angiogenesis inhibitor, a photoactive agent, a radiosensitizing agent, or a radioisotope.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Blocking Thrombin Cleavage of Osteopontin Suppresses B16 Tumor Growth and Metastasis Thrombin cleaves OPN in vivo to regulate OPN function. OPN contains multiple conserved functional domains, including an RGD sequence that binds to multiple integrins, a variant CD44 (vCD44)-binding domain and a heparan sulfate-binding domain. Just C-terminal to the RGD sequence is a conserved thrombin cleavage site (at Arg[168] in human and Arg[153] in mouse) that when cleaved exposes a previously cryptic integrin-binding site for $\alpha4\beta1$ and $\alpha9\beta1$ integrins at the new C-terminus, SVVYGLR (SEQ ID NO:4, Yokosaki et al., 1999). Thrombin-cleaved OPN-Arg (OPN-R) has enhanced $\alpha4\beta1$-dependent cell-binding activity compared to OPN-full length (OPN-FL) that is abolished when the C-terminal arginine in OPN-R is cleaved by either carboxypeptidase N (CPN), or carboxypeptidase B2 (CPB2, also known as thrombin-activatable fibrinolysis inhibitor, TAFI) (Leung and Morser, 2018). This second cleavage converts OPN-R to OPN-Leu (OPN-L), suggesting that the sequential cleavages of OPN-FL by thrombin and CPN or CPB2 represent a sequential up- and down-regulation of OPN's cell adhesion activity (Myles et al., 2003) (FIG. 1A). Finally, we showed that the C-terminal OPN fragment (OPN-CTF) acquires a new conformation-dependent chemotactic activity towards dendritic cells (DC) (Shao et al., 2014).

We created ELISAs specific for OPN-R and OPN-L, and showed that levels of OPN-R and OPN-L are substantially elevated in the joint fluid of patients with inflammatory arthritis, demonstrating that these cleavages occur in vivo (Sharif et al., 2009). Because of the inability to specifically measure the thrombin-cleaved OPN fragments in the past, the role of thrombin cleavage of OPN in cancer biology has been largely overlooked. We showed that OPN-R and OPN-L are significantly increased in the cerebral spinal fluid (CSF) of patients with GBM and non-GBM malignant gliomas (Yamaguchi et al., 2013). OPN and the cleaved fragments promote motility and adhesion of U87 MG cells, a human GBM cell line, and confer resistance to apoptosis, thus cleaved OPN fragments may promote GBM development.

To define the role of thrombin cleavage of OPN in vivo, we created a thrombin cleavage-resistant OPN$_{R153A}$ knock-in (OPN-KI) mouse and discovered that B16 murine melanoma growth and metastasis are grossly suppressed in these mice.

Results
Suppression of B16 Tumor Growth in OPN-KO and OPN-KI Mice

Figure 1B:
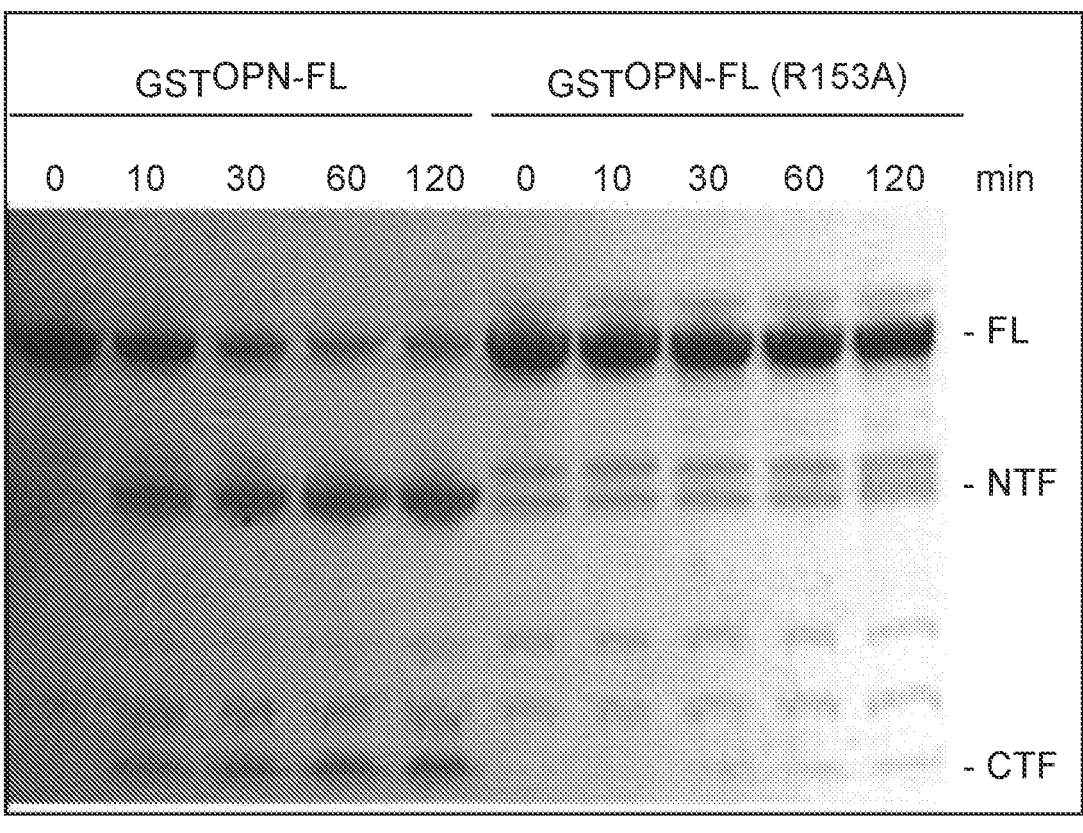

To confirm that a mutation in the thrombin cleavage site would render the resulting OPN thrombin resistant, we expressed a mutant OPN (OPN$_{R153A}$) with the arginine (R) in the thrombin cleavage site mutated to alanine (A) (R153A) in *E. coli* and demonstrated that it is resistant to thrombin cleavage (FIG. 1B). The OPN-KI (OPN$_{R153A}$) mice, similar to OPN-KO mice, were fertile and healthy before challenge, without any phenotypic changes observable in CBC, liver function and kidney function (FIGS. 9 and 10)

Figure 1C:
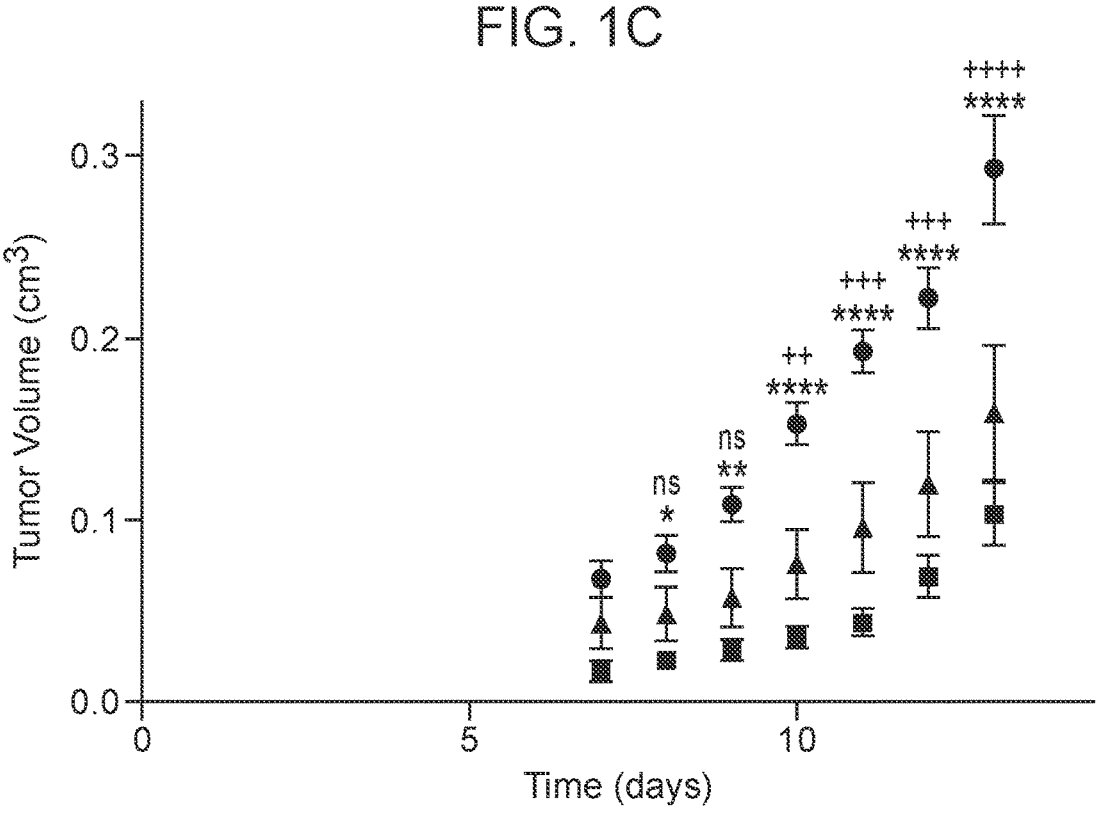
Figure 1D:
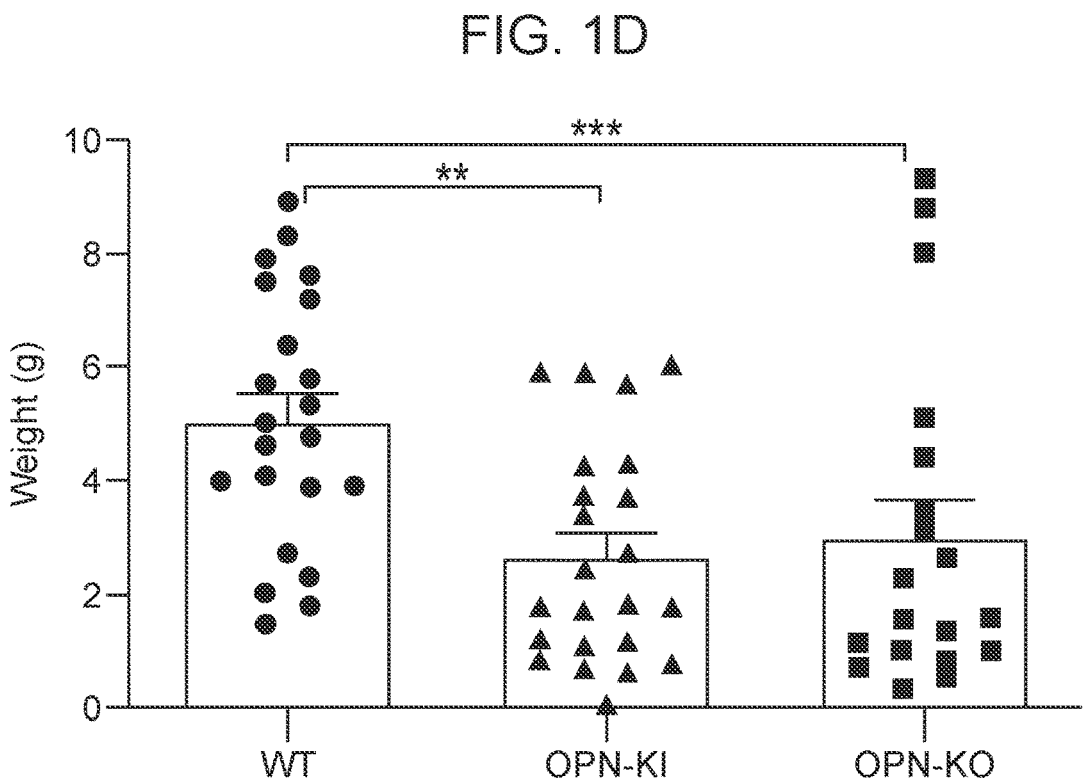
Figure 2A:
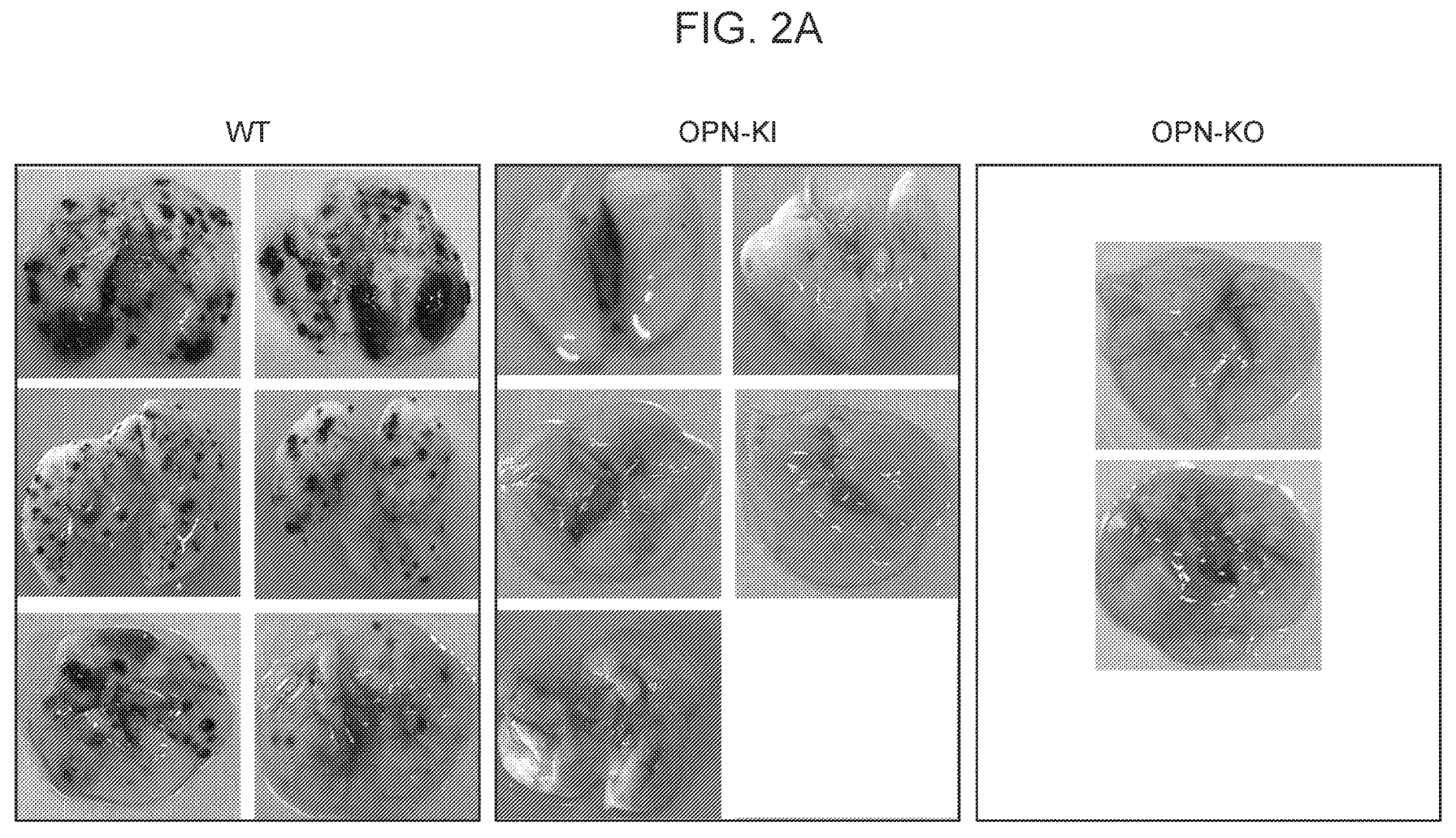
Figure 2B:
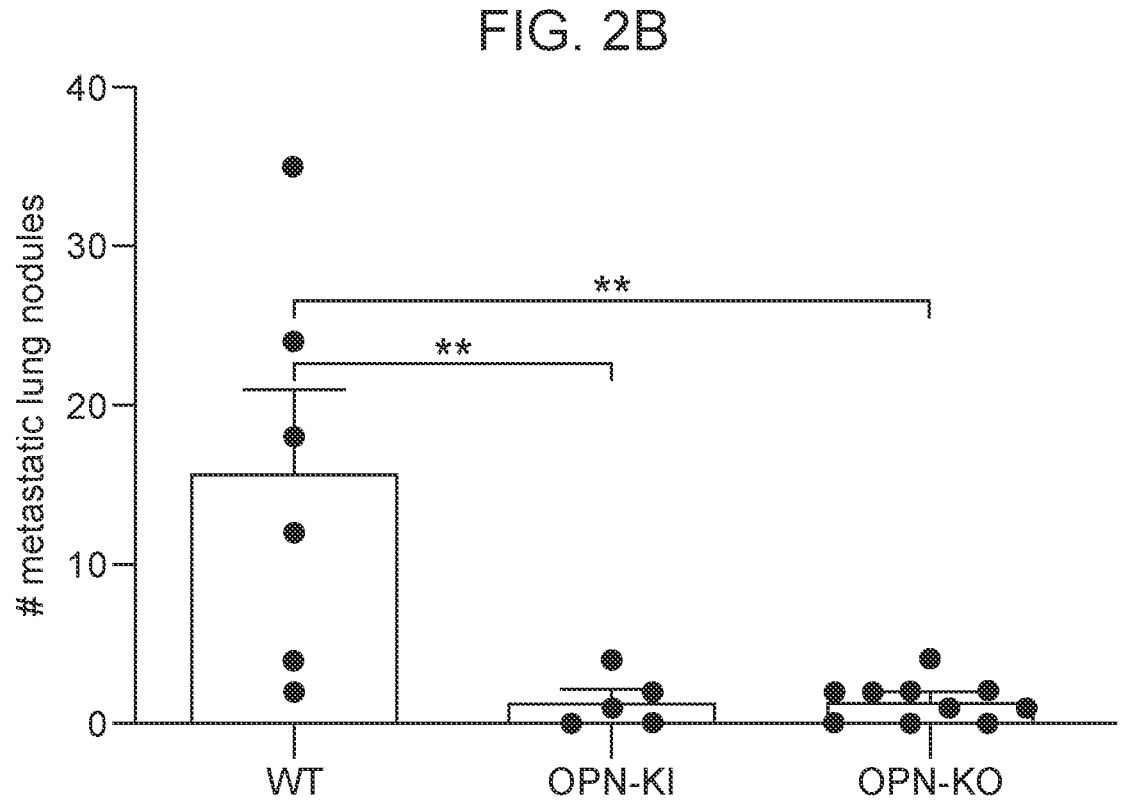
Figure 2C:
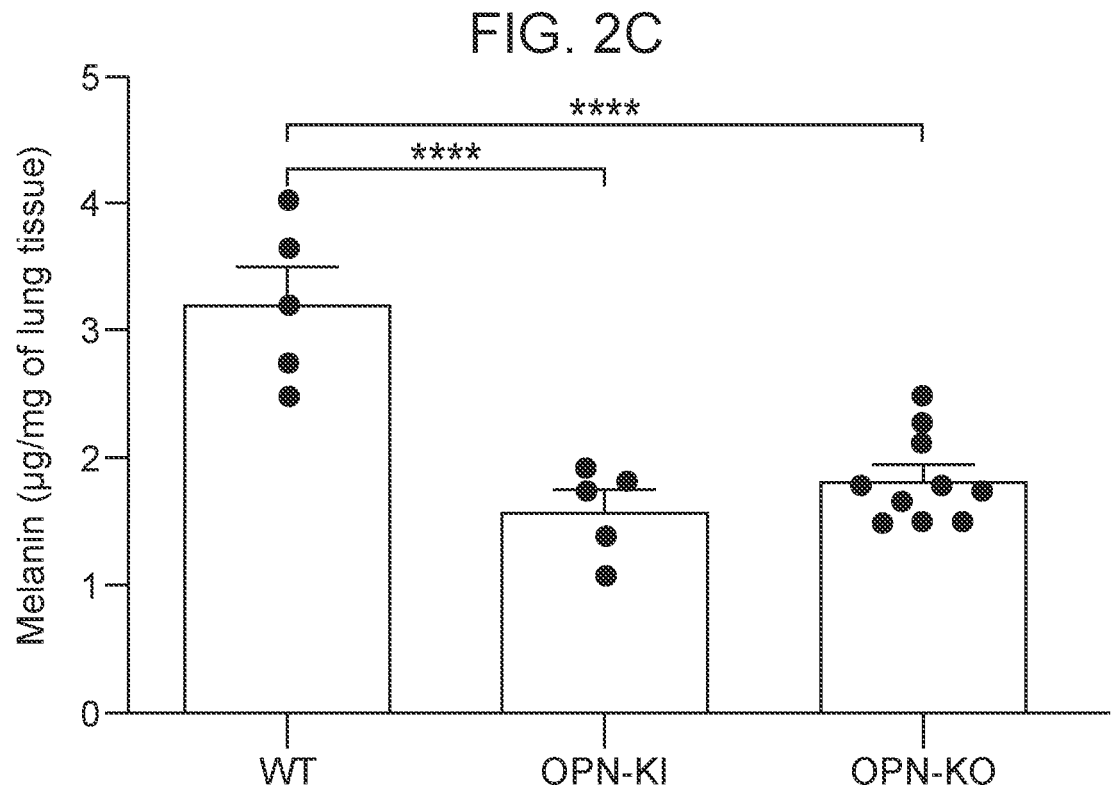
Figure 3A:
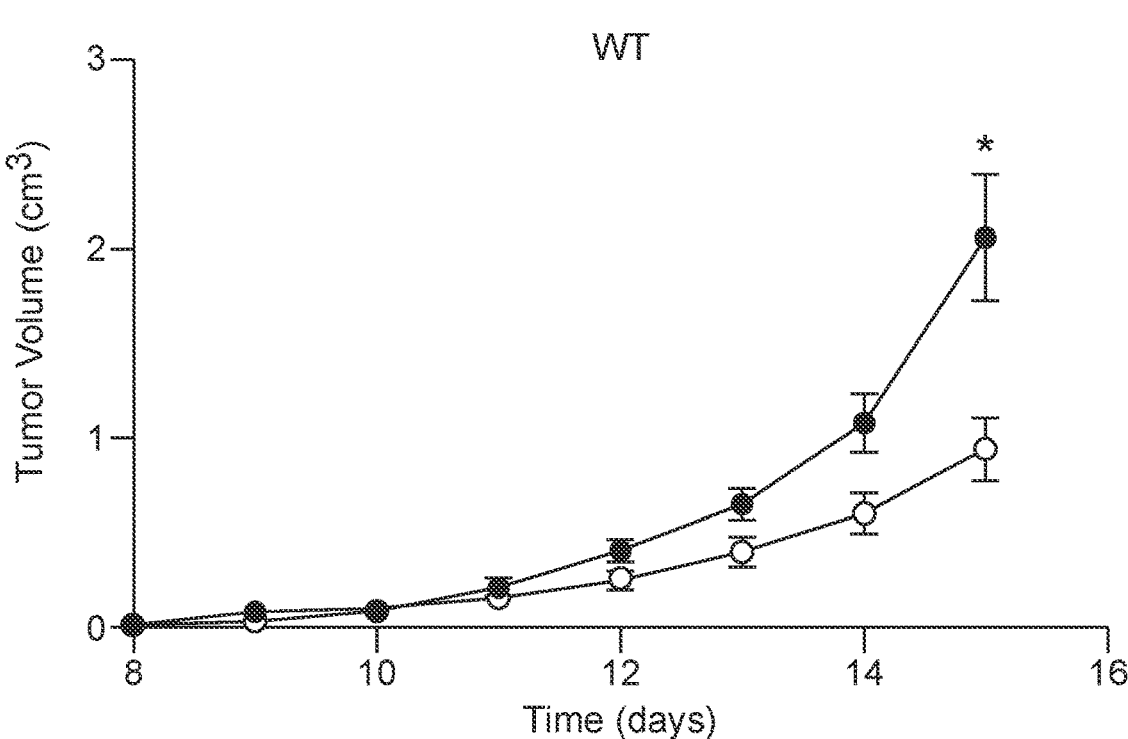
FIGS. 3A-3H: Inhibition of thrombin in WT phenocopies the OPN-KI phenotype.
Figure 3B:
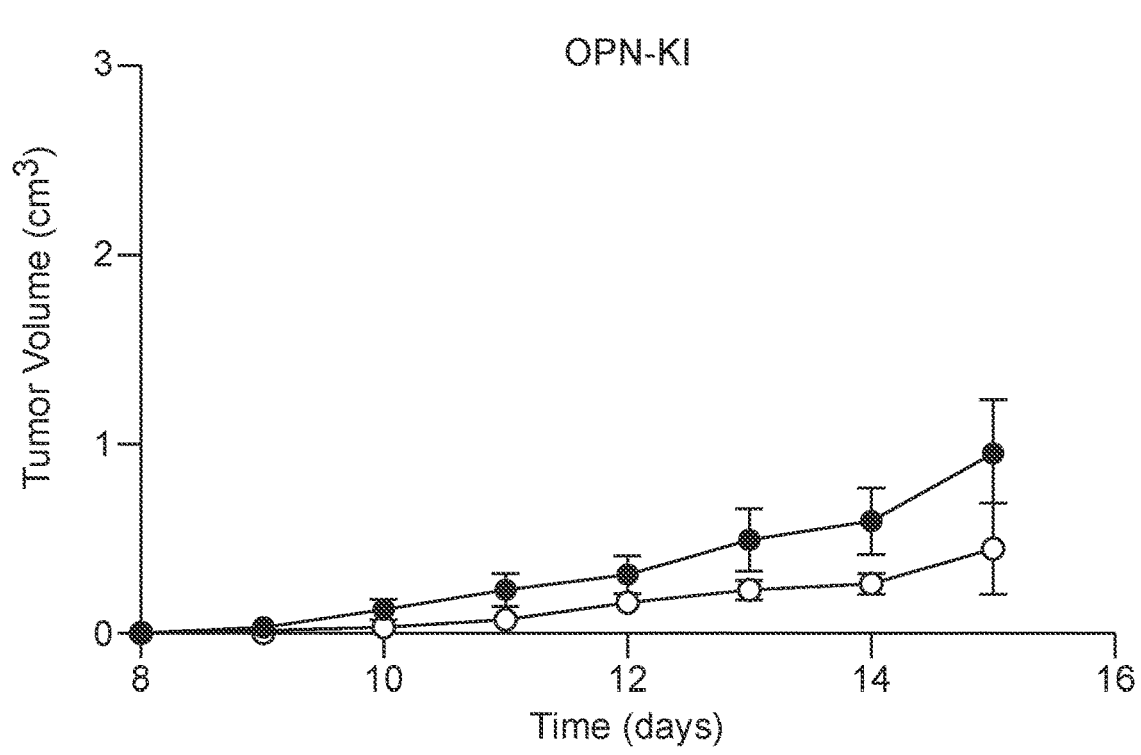
Figure 3C:
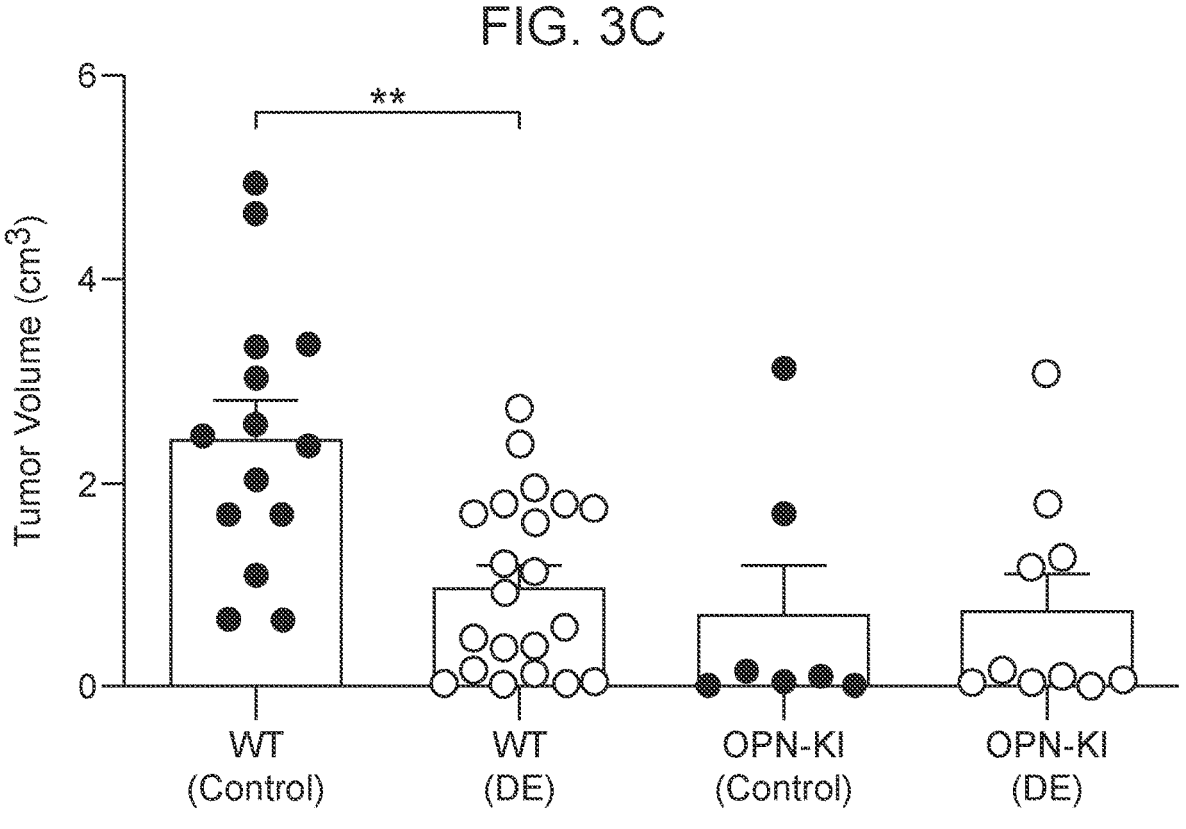
Figure 3D:
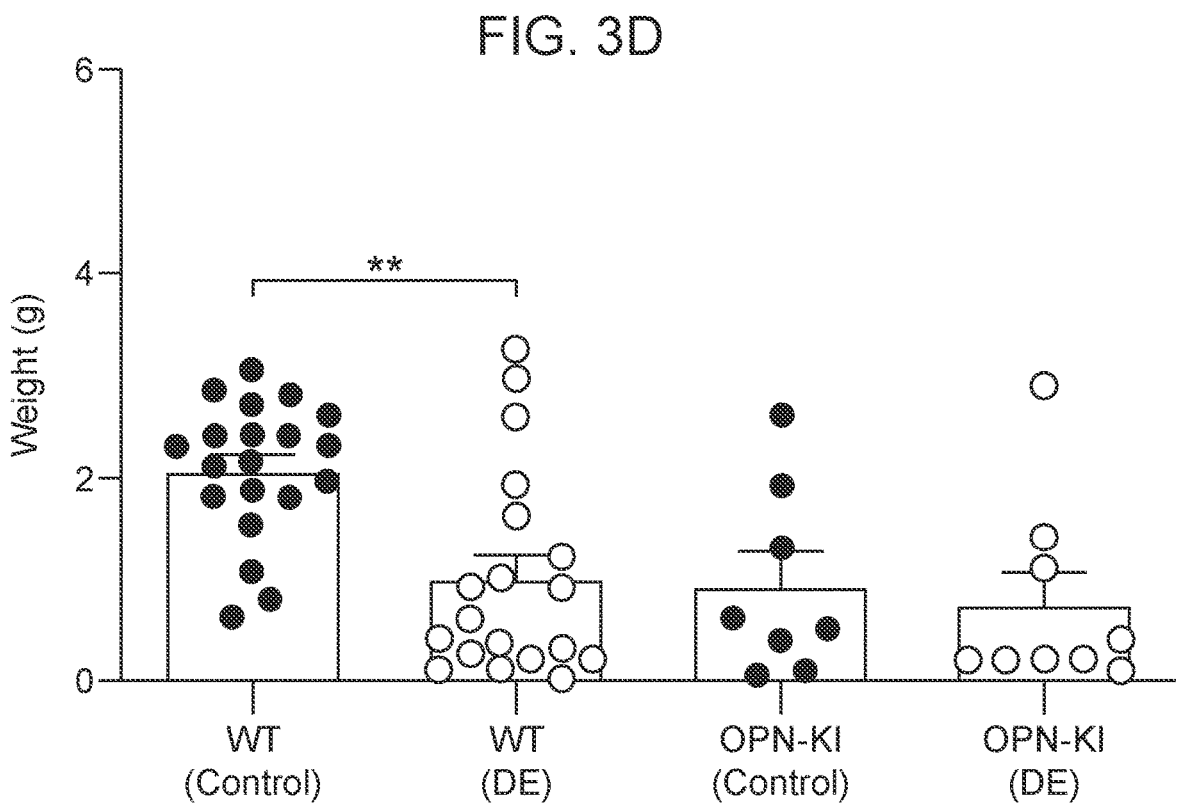
Figure 3E:
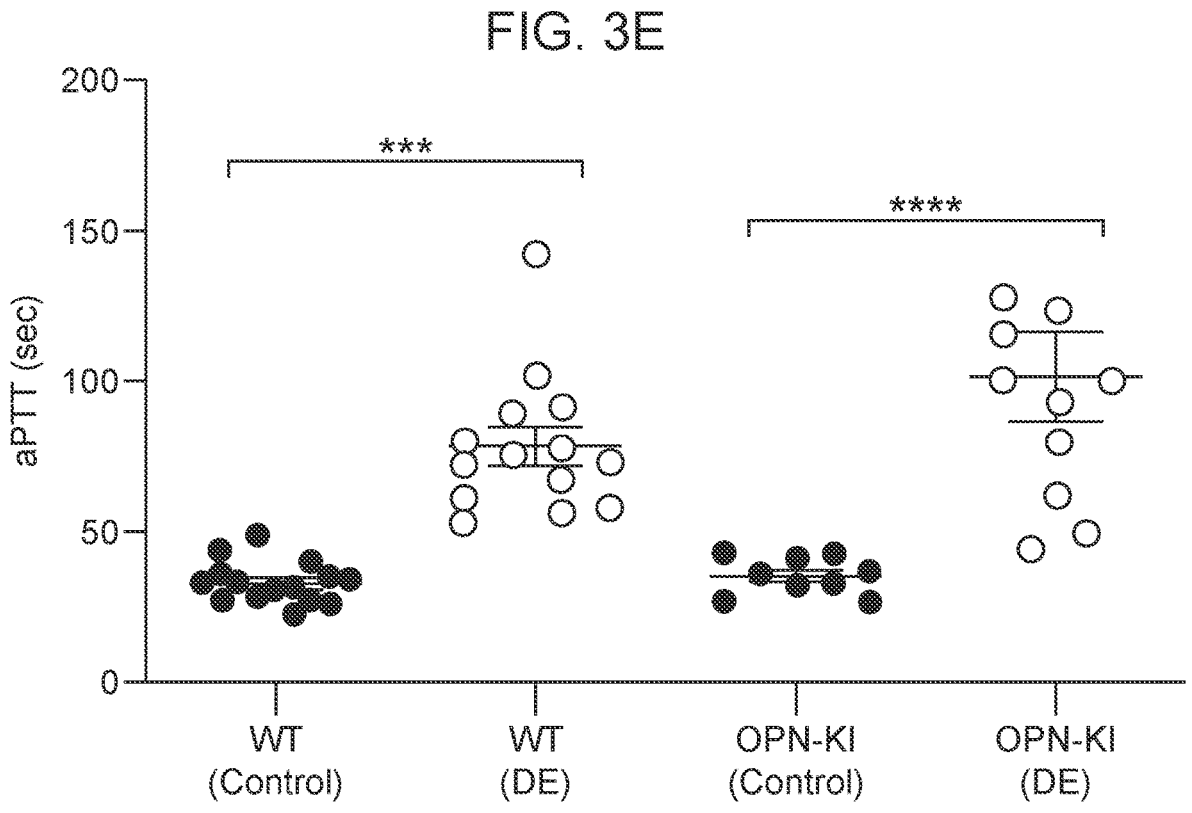
Figure 3F:
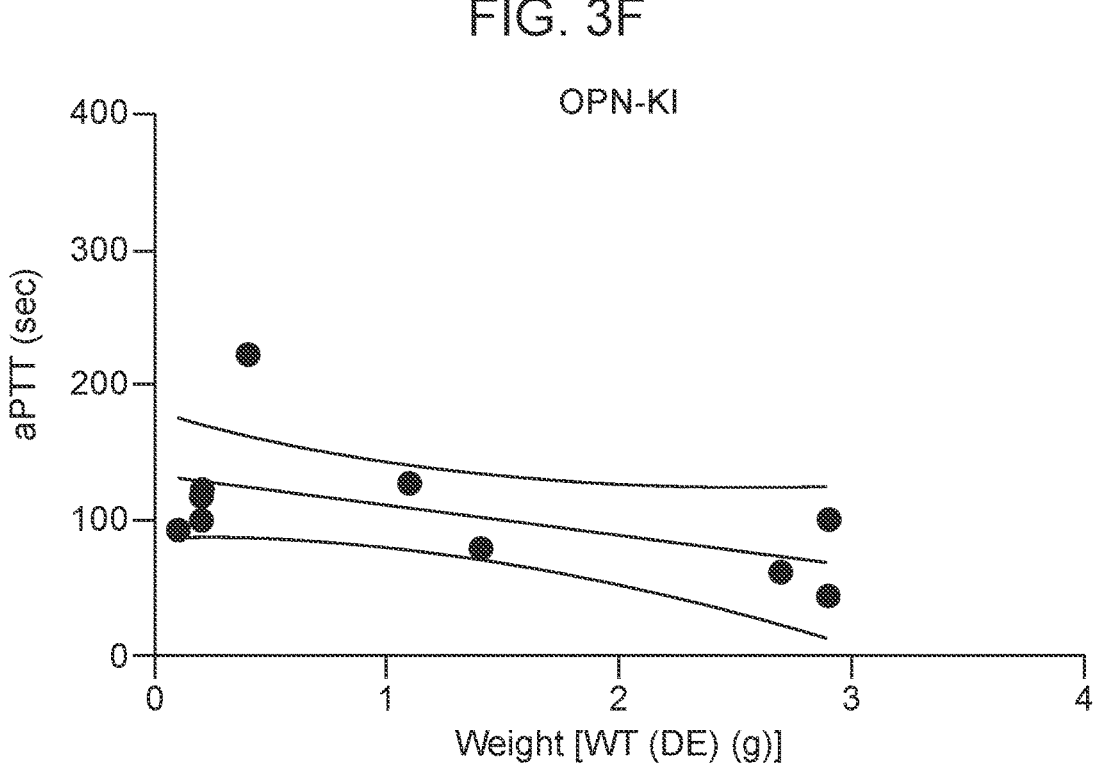

Based on previous reports that growth of murine melanoma B16 tumors is suppressed in OPN-KO compared to WT mice (Nemoto et al., 2001; Ohyama et al., 2004), we tested if the same phenotype would be observed in OPN-KI mice. B16 tumor growth was suppressed in OPN-KO or OPN-KI mice (FIG. 1C). After 2 weeks, tumor weight was lower in OPN-KI mice (mean 2.7±0.4 g, n=23) and OPN-KO mice (mean 3.0±0.7 g, n=19) than WT mice (mean 5.1±0.5, n=22; OPN-KI vs. WT p=0.0032 and OPN-KO vs. WT p=0.0187) (FIG. 1D). Comparison of results in male and female mice showed no difference between genders in the reduction of tumor size in OPN-KI mice versus WT mice (FIG. 11). Similarly, varying the number of B16 cells inoculated did not remove the difference in tumor size in OPN-KI mice versus WT mice (FIG. 11). There was no difference in tumor growth or weight between OPN-KO and OPN-KI mice. Taken together, thrombin resistant OPN-KI mice phenocopy OPN-KO mice in the B16 melanoma tumor model by also having smaller tumors than WT mice.
Suppression of B16 Metastasis in OPN-KI Mice Similar to OPN-KO Mice In addition to primary tumors, OPN-KO mice also exhibit reduced tumor metastases compared to WT mice in a hematogenous pulmonary metastasis model (Nemoto et al., 2001). We repeated this model to assess whether OPN-KI mice display a similar phenotype. After sacrifice, clinical inspection revealed that the tumor burden was reduced in both OPN-KI and OPN-KO mice when compared to WT mice (FIG. 2A). Quantitation by counting metastatic pulmonary nodules showed a comparable reduction in tumor burden in both OPN-KI mice (1.4±0.7/lung, n=5) and OPN-KO mice (1.5±0.4/lung, n=10) compared to WT mice (15.8±5.1/lung, n=6; OPN-KI vs. WT: p=0.0061; OPN-KO vs WT: p=0.0016; FIG. 2B). Determination of the melanin content of the lungs showed that it was lower in OPN-KI mice (1.6±0.2 g/mg lung tissue, n=5) and OPN-KO mice (1.82±0.11 µg/mg lung tissue, n=10) compared to WT mice (3.2±0.3 g/mg lung tissue, n=6, OPN-KI vs. WT: p=<0.0001; OPN-KO vs WT: p=<0.0001; FIG. 2C). The numbers of metastatic pulmonary nodules and melanin content were reduced equivalently, suggesting that both the process by which the B16 cells exited the vasculature and established tumors in the extravascular compartment as well as the growth of those tumors were inhibited by the prevention of thrombin cleavage of OPN.
Inhibition of Thrombin in WT Mice Phenocopies the OPN-KI Phenotype Since B16 tumor growth and metastases were suppressed in thrombin-resistant OPN-KI mice similarly to OPN-KO mice, we investigated if blocking OPN cleavage by inhibiting thrombin with an oral thrombin inhibitor would also reduce tumor size in WT mice. Mice were treated with the orally active thrombin inhibitor, dabigatran etexilate (DE), compounded into their chow or matched control chow (Sparkenbaugh et al., 2014) from 4 days before B16 inoculation until sacrifice. WT mice treated with DE showed tumor suppression (FIG. 3A) similar to that observed in OPN-KI mice irrespective of whether the KI mice had been treated with DE (FIG. 3B). The tumor volume after sacrifice was lower in WT mice treated with DE (1.0±0.2 cm³; n=14 vs. 2.5±0.4 cm³; p=0.0017; n=21; FIG. 3C). Tumor volume of OPN-KI were similar with and without DE treatment (0.73±0.3 cm³; n=10 vs. 0.77±0.5 cm³, p=0.9999; n=7; FIG. 3C) and were also similar to DE treated WT. The tumor weights observed in DE-treated WT mice (1.0±0.2 g vs. 2.5±0.4 g, p=0.0018) were similar to those found in OPN-KI mice (0.8±0.9 vs. 0.73±0.9; p=0.9716; FIG. 3D). We confirmed this dosing regimen blocked thrombin activity by measuring activated partial thromboplastin time (aPTT) (FIG. 3E) and noted a trend of increased anticoagulation to be inversely correlated with tumor weight (FIG. 3F, R=−0.37). Thus, inhibition of thrombin in WT mice recapitulates the thrombin-resistant OPN-KI phenotype. Treatment of OPN-KI mice with DE did not further reduce B16 tumor weight and volume, suggesting that there were no additional effects of thrombin inhibition beyond prevention of OPN cleavage.

Figure 3G:
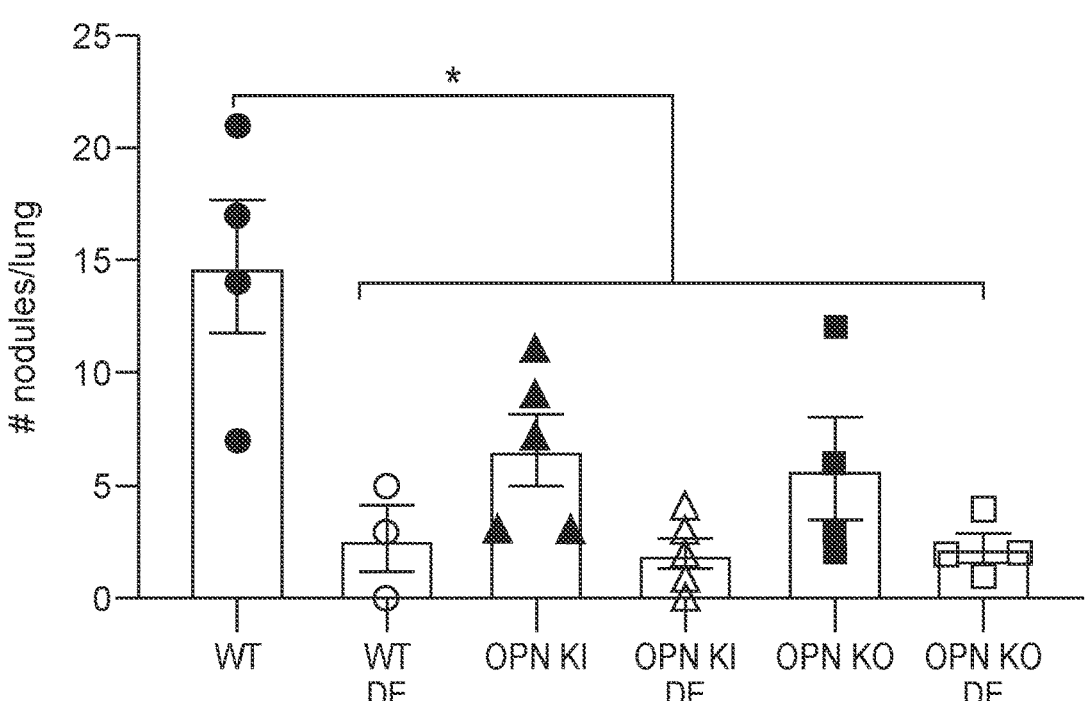
Figure 3H:
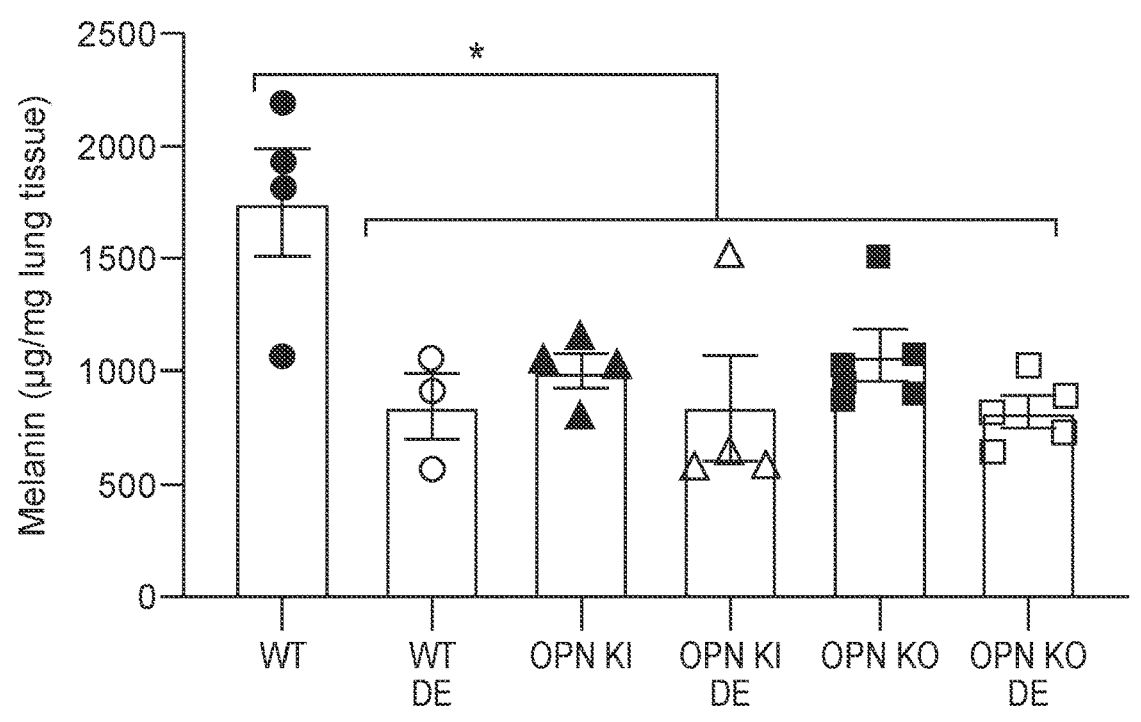

We also repeated the DE experiments using the pulmonary metastases model. Compared to control WT mice, DE-treated mice exhibited fewer metastatic nodules/lung and reduced melanin content (FIGS. 3G, 3H). While DE treatment had no effect on local tumor growth in OPN-KI (FIG. 3A) and OPN-KO mice, there was a trend for DE-treated OPN-KI or OPN-KO mice to exhibit fewer pulmonary metastases and decreased melanin content compared to untreated OPN-KI or OPN-KO mice respectively (FIGS. 3G, 3H).

Detection of OPN Cleavage Products in B16 Tumors and Plasma in WT Mice

Figure 4A:
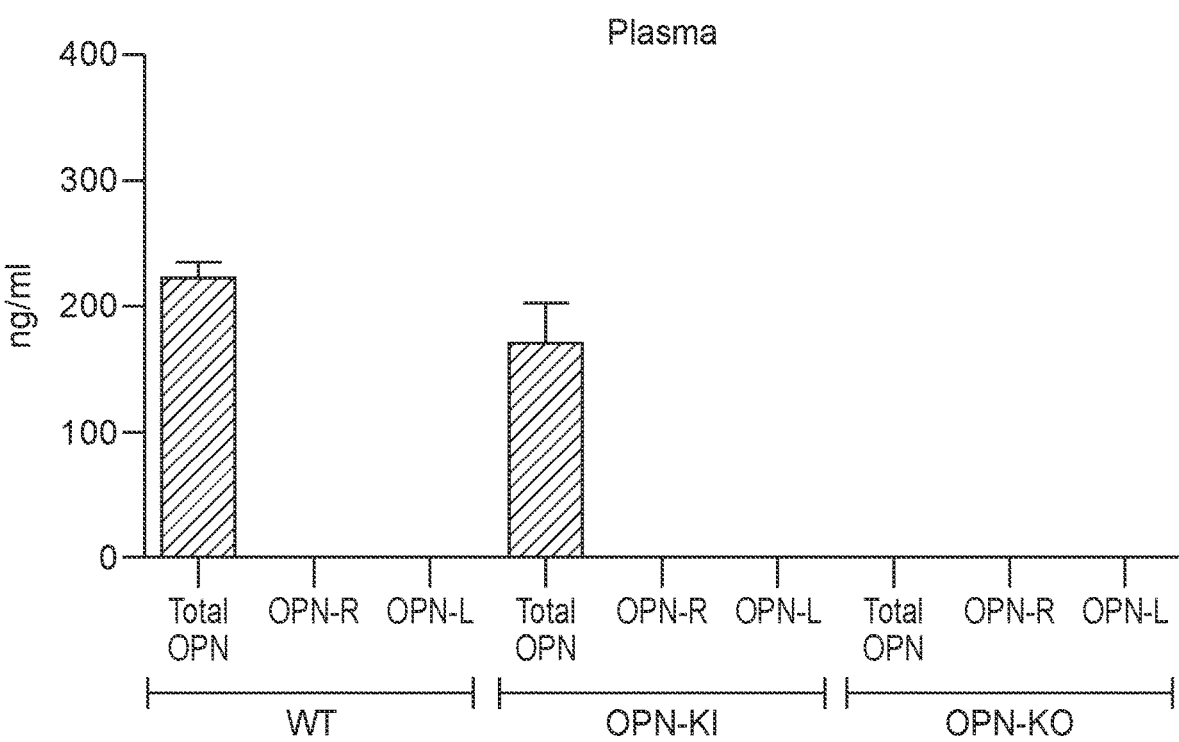
Figure 4B:
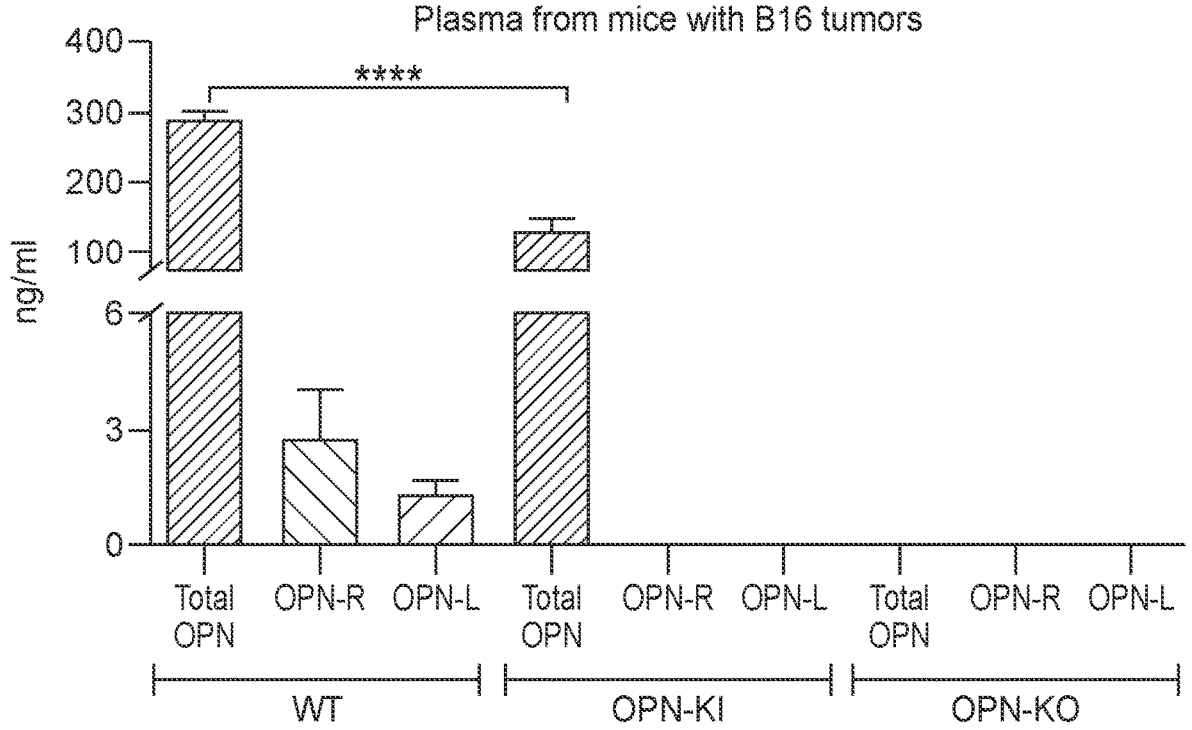
Figure 4C:
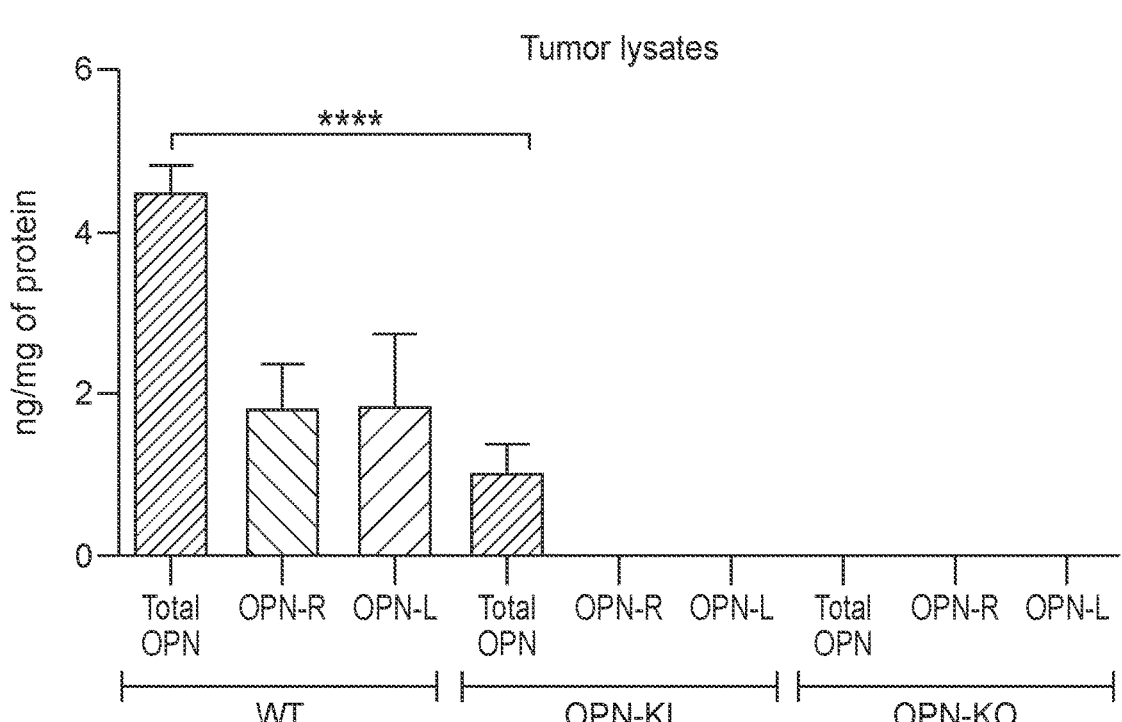

We assessed OPN cleavage products in WT mice pre- and post-tumor implantation. Total OPN plasma levels were similar in WT mice (223.5±11.3 ng/ml) and OPN-KI mice (170.6±34.2 ng/ml; p=0.1668) and OPN-KO mouse plasma contained no detectable OPN. Prior to tumor implantation, no OPN cleavage products were detected in all genotypes. 14 days after B16 tumor implantation, total OPN plasma levels were increased in WT mice and OPN-KI mice. We detected low levels of thrombin cleavage products, OPN-R and OPN-L, in WT mice but not in OPN-KI mice (FIG. 4B). Within tumor lysates, total OPN was ~4 fold higher in samples from WT mice compared to that from OPN-KI mice (4.5±0.32 ng/mg vs. 1.0±0.35 ng/mg, p=<0.0001) with none detectable in tumors from OPN-KO mice. Moreover, there was >80% cleavage of the OPN into OPN-R and OPN-L in WT tumor lysates (FIG. 4C). In contrast, OPN-R and OPN-L were not detected in tumor lysates from OPN-KI mice. These data show that the thrombin cleavage products of OPN are present both in the B16 tumor and in plasma in WT mice, with the potential of modifying the tumor locally and the host responses systemically.

B16 Cells do not Express OPN but Express OPN-Binding Integrins

Figure 12:
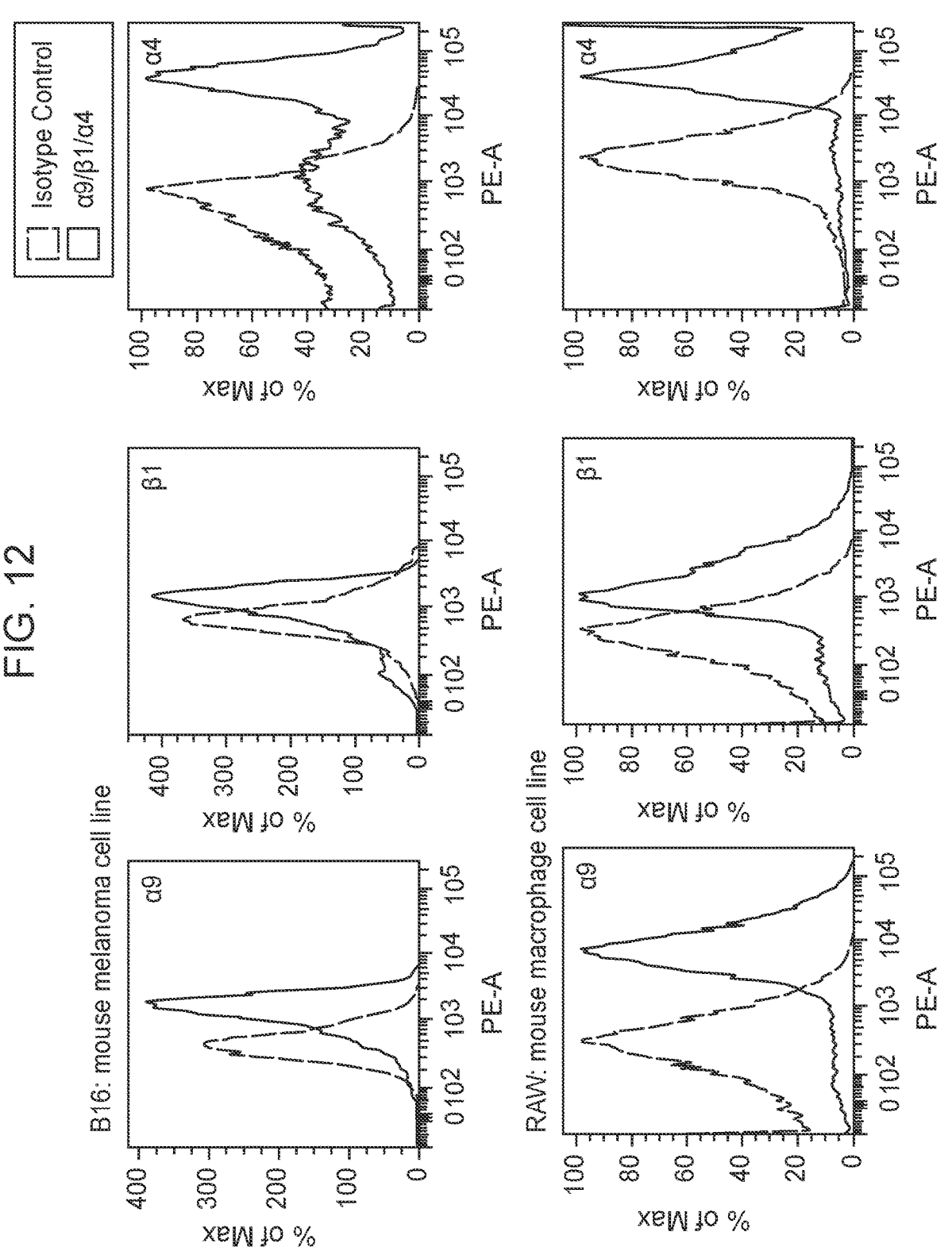
FIG. 12: Expression of α9β1 and α4β1 integrins on B16 and RAW cells by flow cytometry using specific antibodies compared to isotype controls.
Figure 13A:
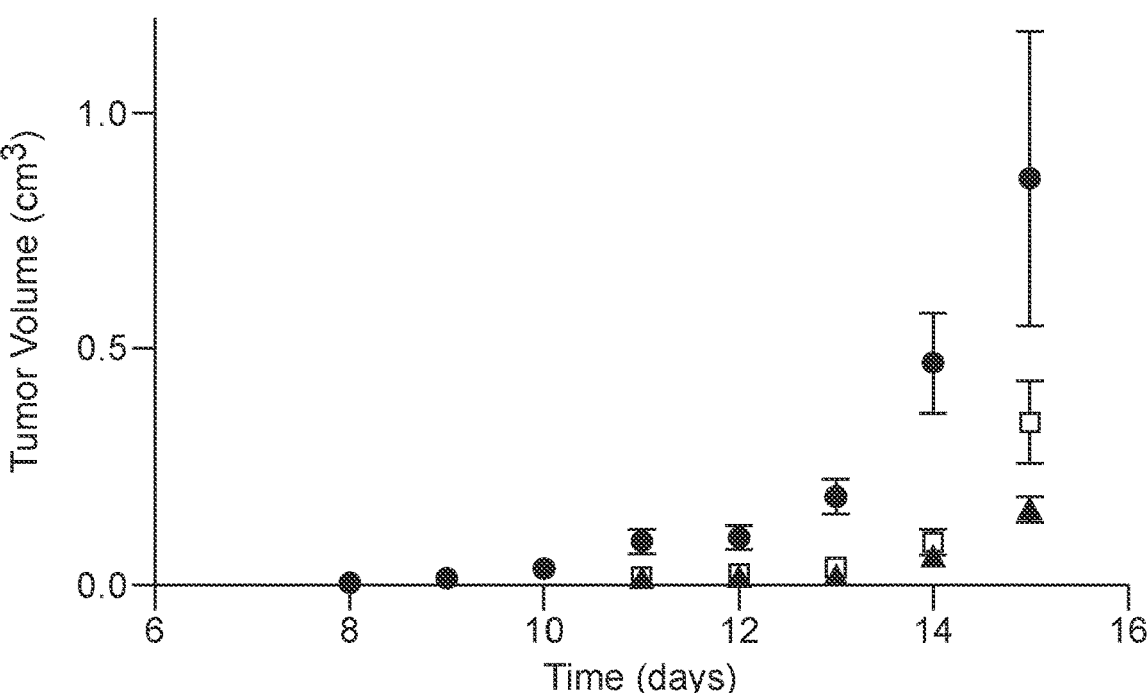
FIGS. 13A-13F: Comparison of B16 tumor growth on NOG mice inoculated with different numbers of B16 cells. Growth rates of B16 tumors in (FIGS. 13A-13C; WT blue circles, NOG-OPN-KI green triangles and NOG-OPN-KO red squares), and weight of B16 tumors after sacrifice in NOG-WT (FIG. 13D), NOG-OPN-KI (FIG. 13E) and NOG-OPN-KO (FIG. 13F) following inoculation with $0.5×10^6$, $1×10^6$ and $2×10^6$ B16 cells respectively. Data analyzed by ANOVA followed by Tukey post hoc test and showed no differences between groups.
Figure 13B:
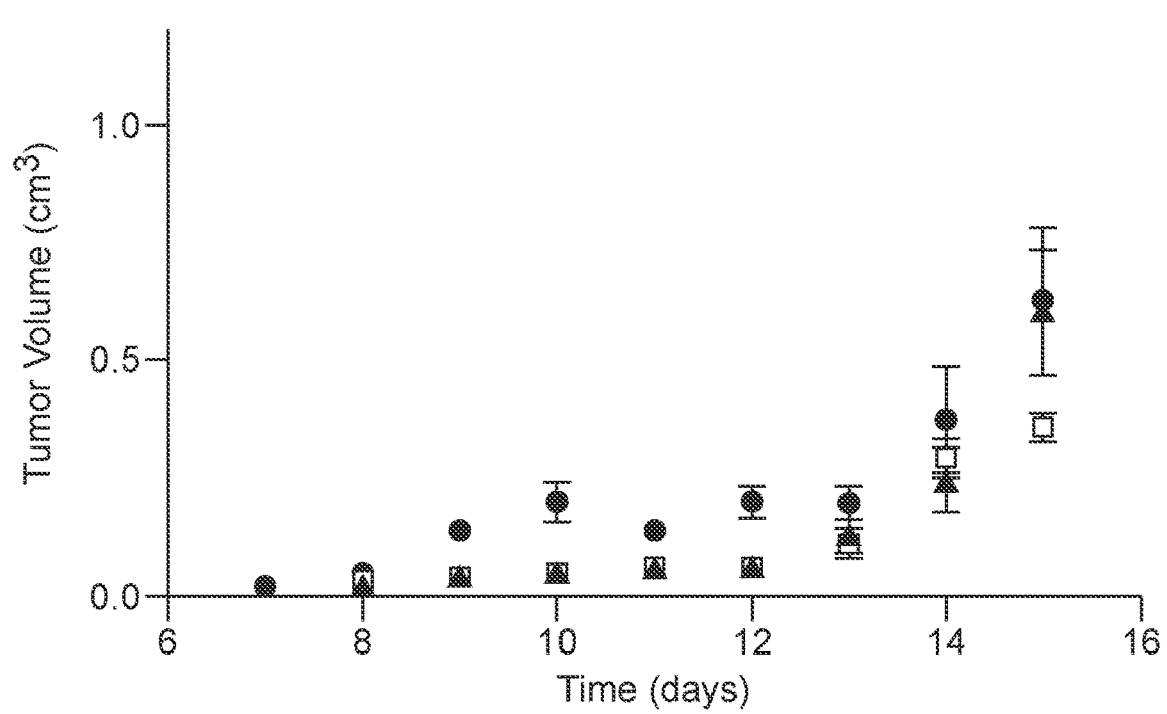
Figure 13C:
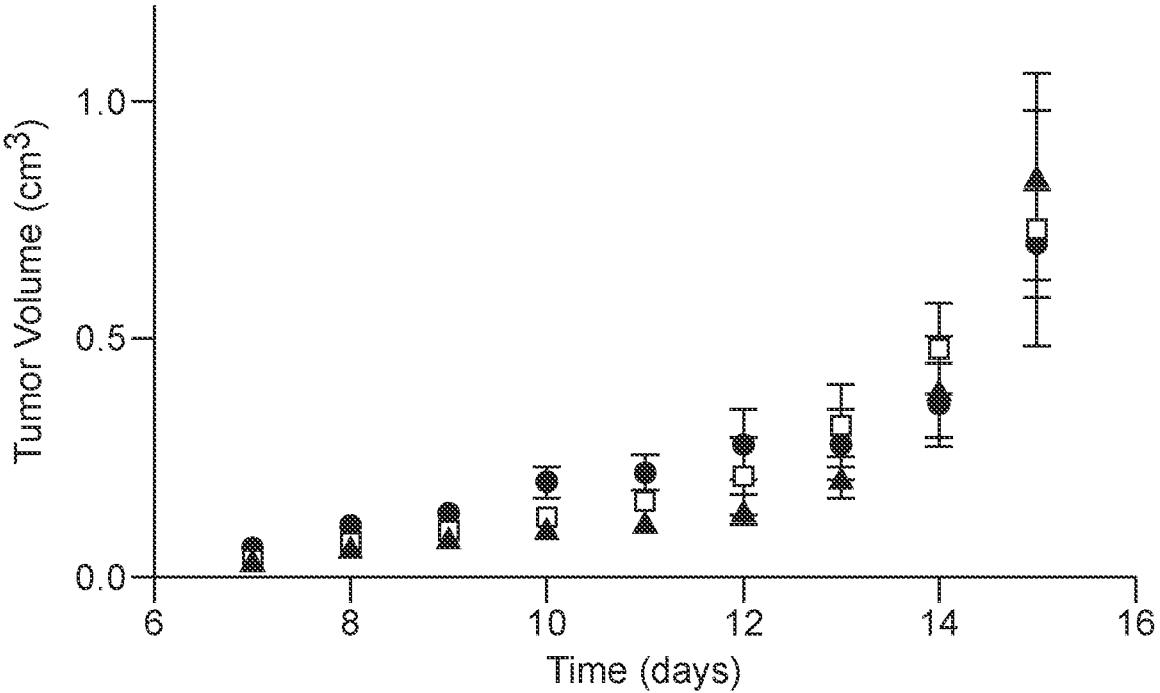
Figure 13D:
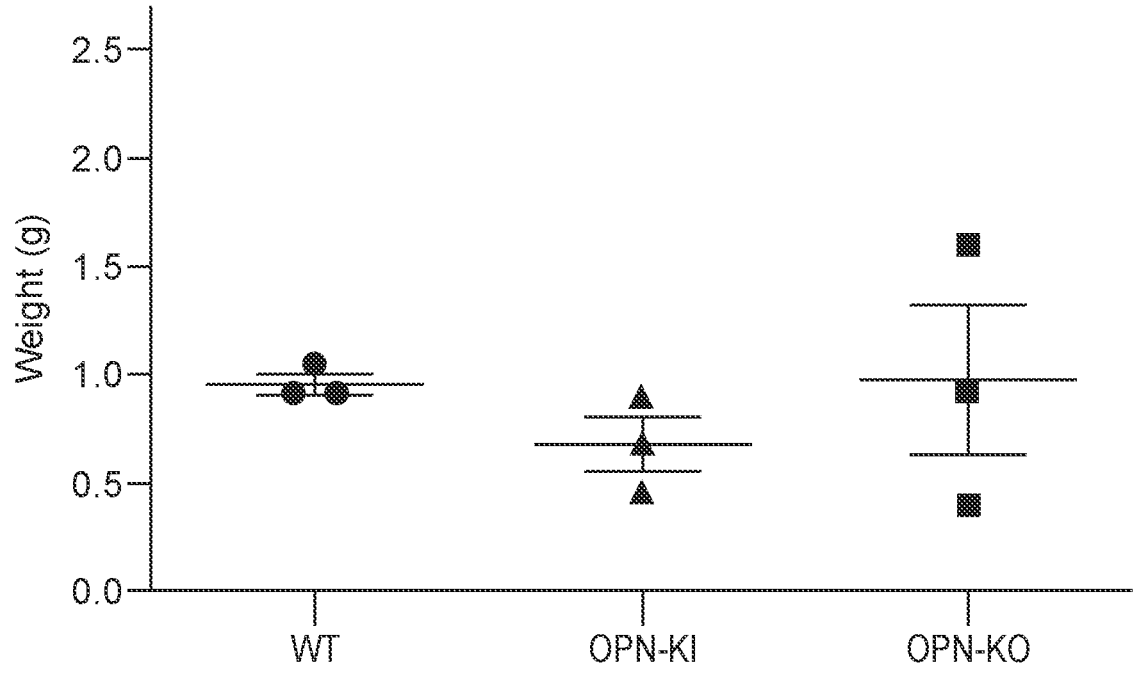
Figure 13E:
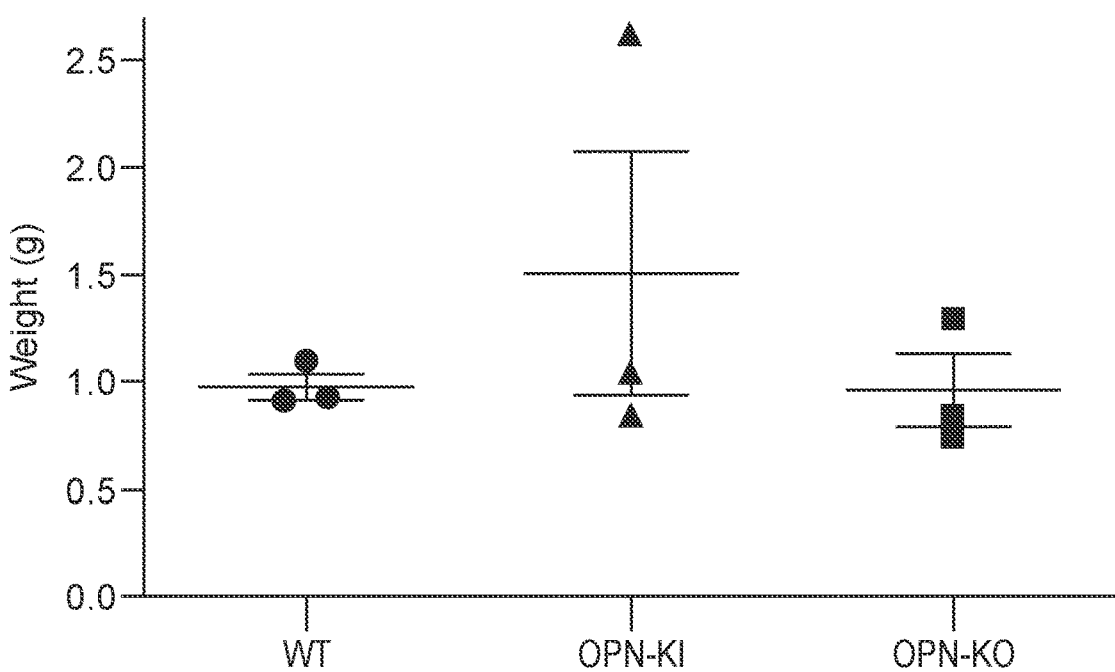
Figure 13F:
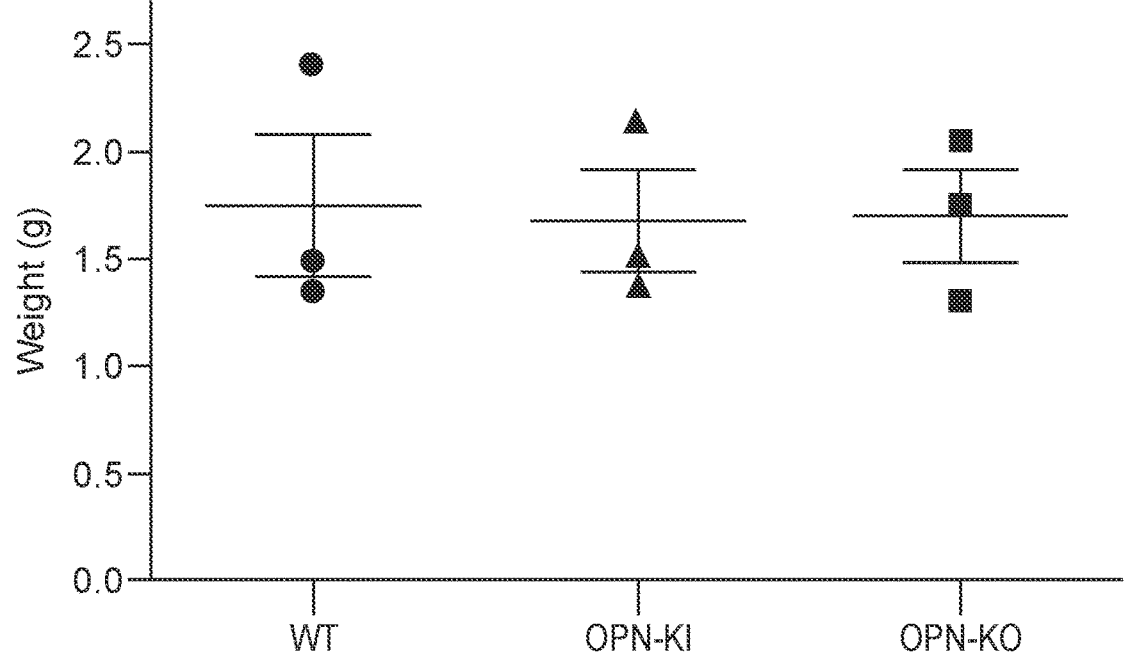
Figure 14A:
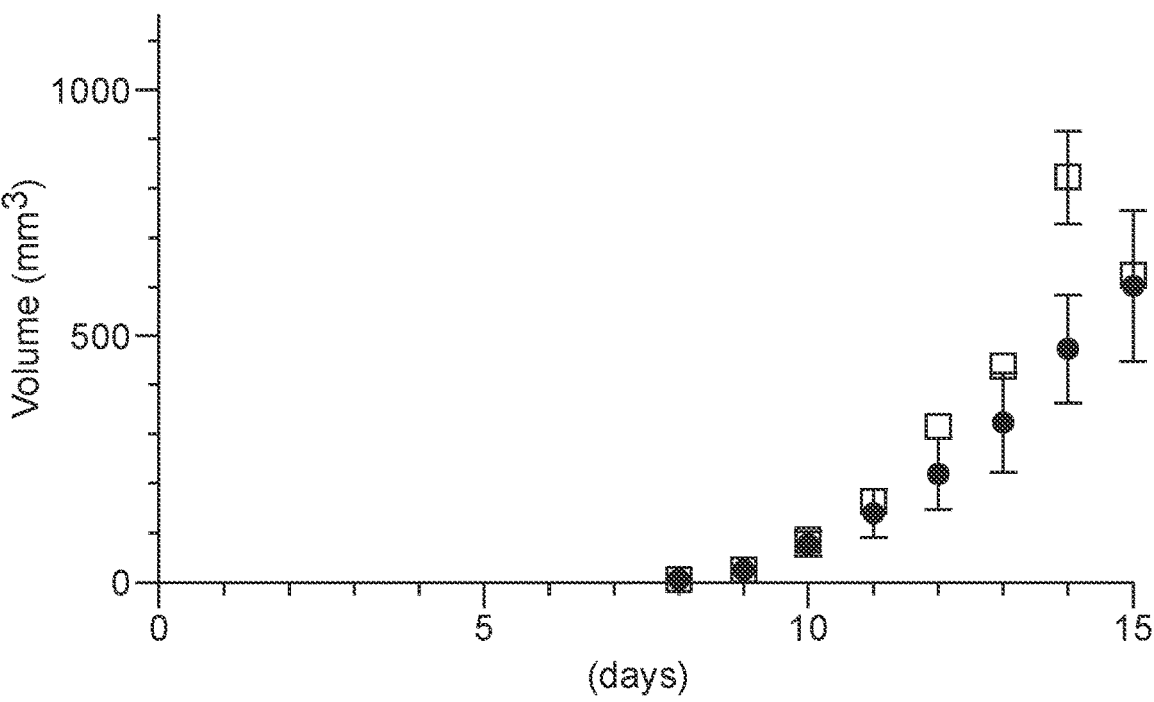
FIGS. 14A-14D: Comparison of B16 growth in male and female NOG mice. Growth rates of B16 tumors in male (closed symbols) or female (open symbols) NOG-WT (FIG. 14A), NOG-OPN-KI (FIG. 14B) and NOG-OPN-KO (FIG. 14C) mice, and weight of B16 tumors after sacrifice in male (closed symbols) or female (open symbols) NOG-WT, NOG-OPN-KI and NOG-OPN-KO mice (FIG. 14D).
Figure 14B:
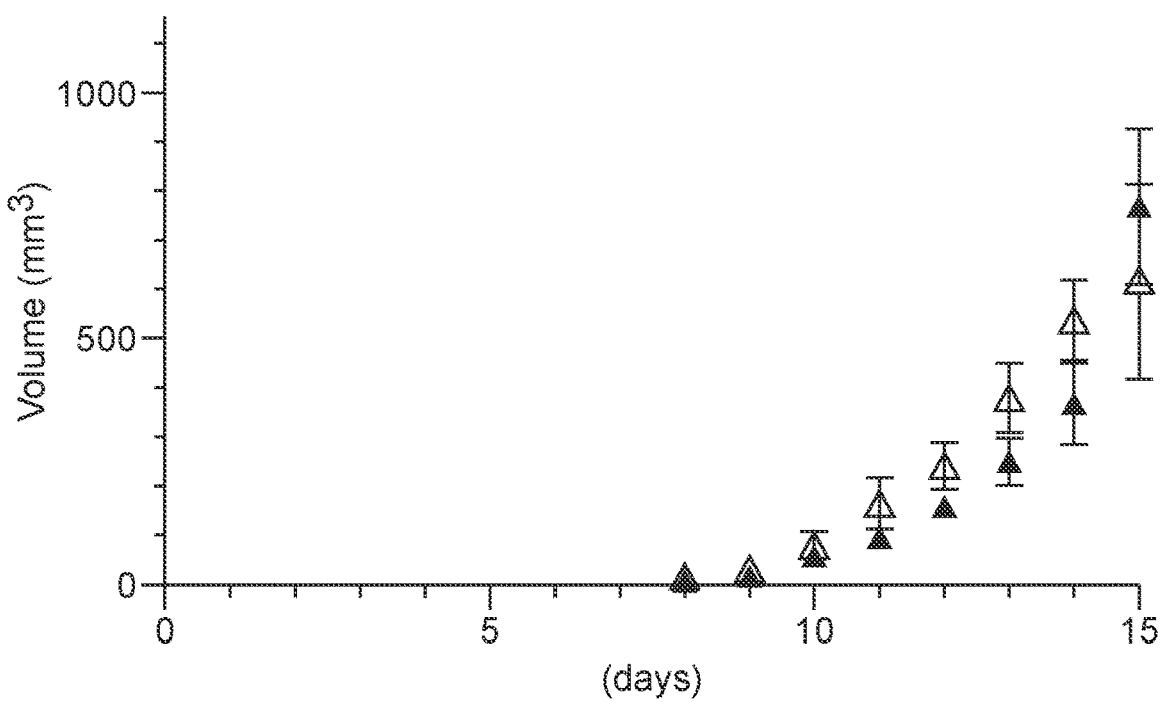
Figure 14C:
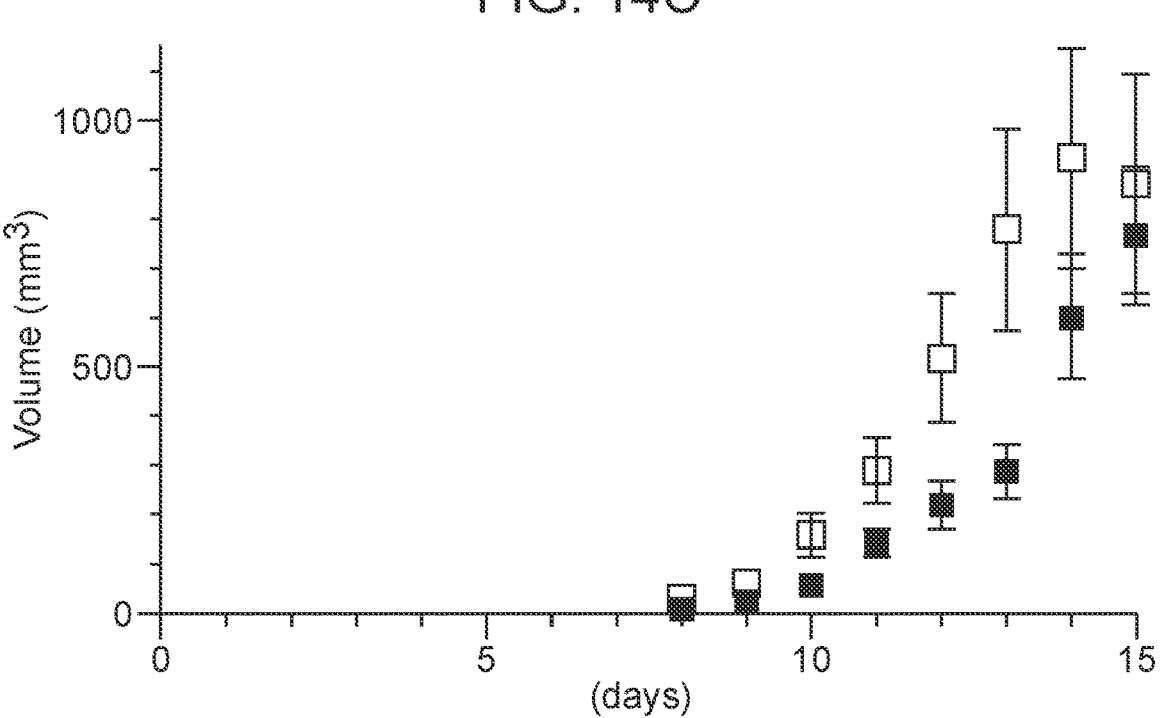
Figure 14D:
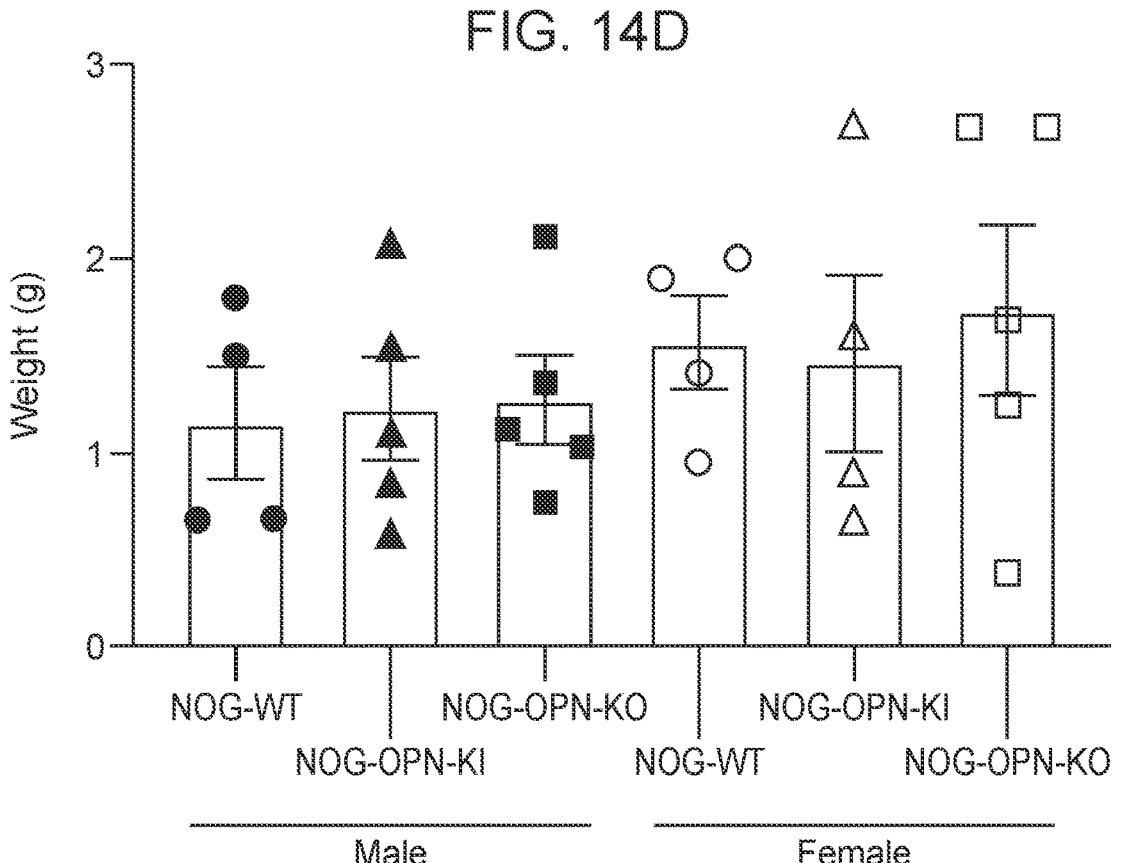

B16 cells have no detectable OPN mRNA expression (Nemoto et al., 2001). We confirmed that OPN was not detectable by ELISA in B16 cell conditioned medium. Thus, B16 cells do not produce OPN and the suppression of B16 tumor growth in OPN-KO and OPN-KI mice compared to WT mice is due to thrombin cleavage of the host OPN. Thrombin-cleaved OPN reveals a cryptic integrin-binding site for integrins α4β1 and α9β1 (Yokosaki et al., 1999), and we demonstrated by FACS that B16 cells express of α4β1 and α9β1 integrins on the cell surface (FIG. 12). We hypothesized that thrombin-cleaved OPN fragments may directly modulate B16 tumor growth and metastases via α9β1 and α4β1 integrins.

Effects of OPN Fragments on B16 Cells

Figure 4D:
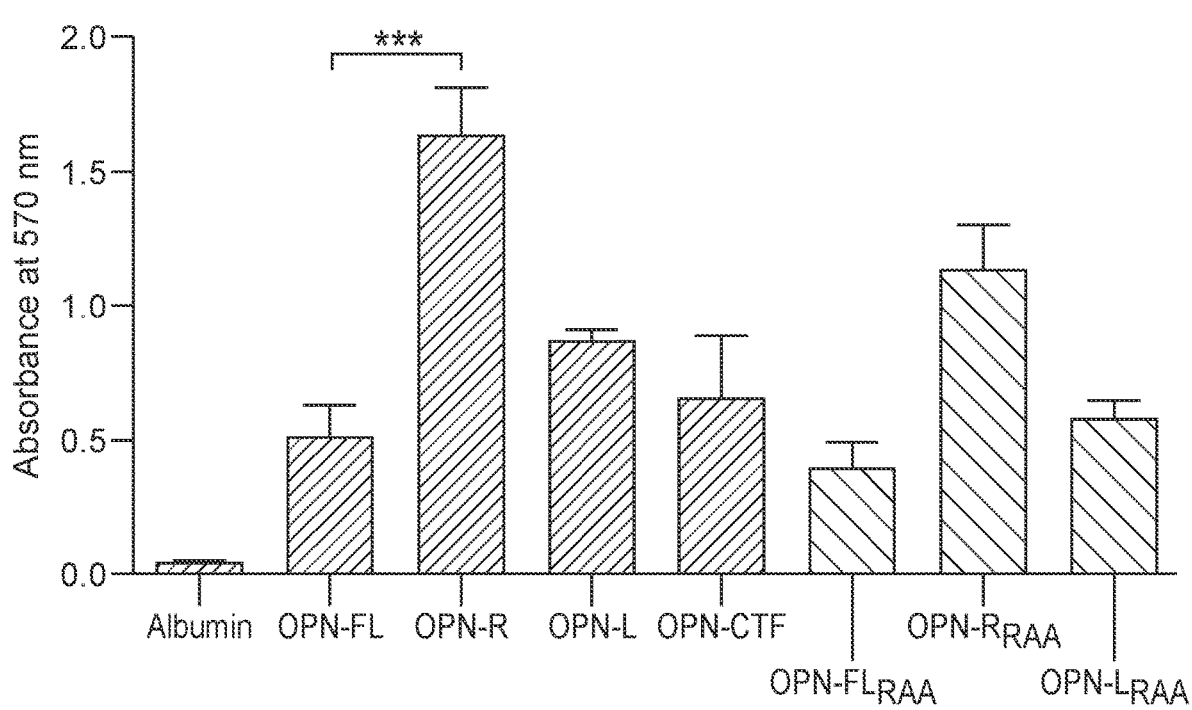
Figure 4E:
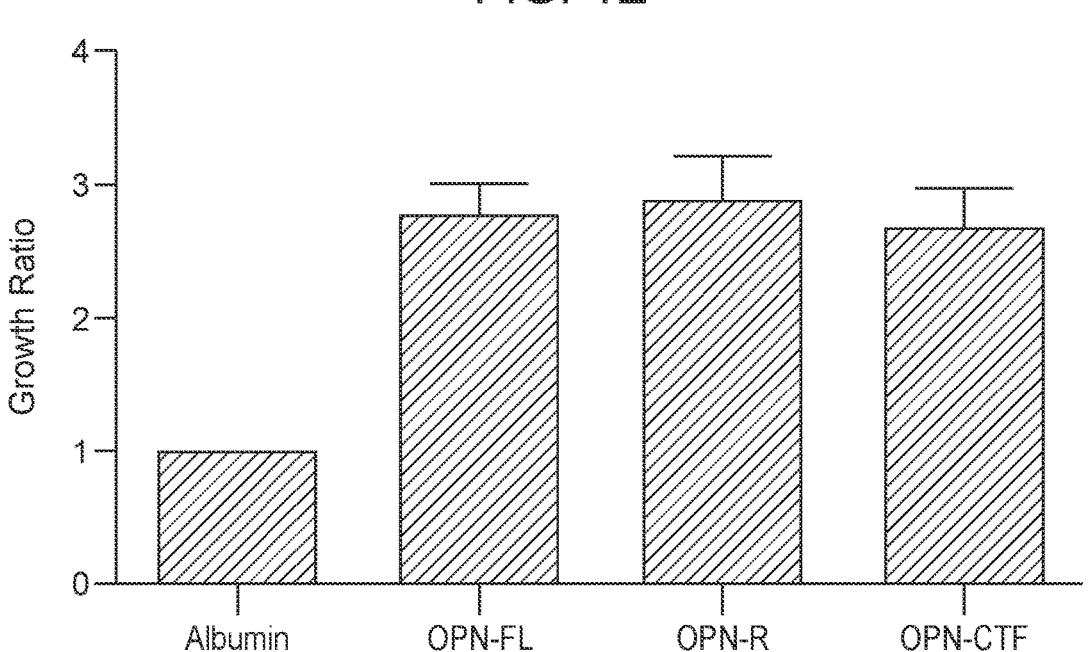

We treated B16 tumor cells with different thrombin-cleaved OPN fragments, including OPN-R, OPN-L and OPN-CTF (Shao et al., 2014). Compared to bovine serum albumin (BSA), all the different OPN fragments increased cell adhesion (FIG. 4D). However, OPN-R had a significant increase (~3.5 fold) compared to the OPN-FL, confirming the importance of thrombin cleavage of OPN. Both OPN-L and OPN-R$_{RAA}$ (in which the RGD sequence in OPN-R has been mutated to RAA) had reduced adhesion compared to OPN-R, indicating that both the RGD and thrombin cleavage-exposed integrin-binding site (SVVYGLR) at the C-terminus of OPN-R are important in cell adhesion, consistent with reported results showing involvement of both a4 and b1 integrins (Cardones et al., 2003; Katagiri et al., 1996). OPN cleaved fragments did not increase B16 cell proliferation (FIG. 4E).

Figure 4F:
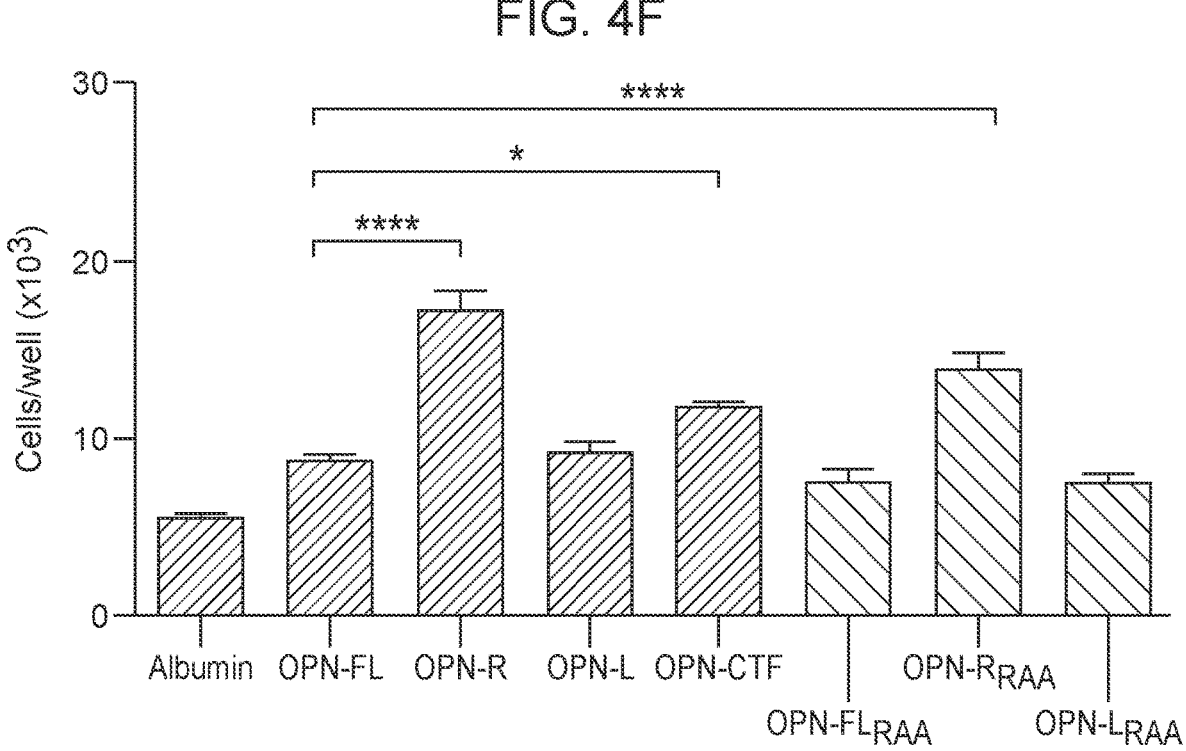

OPN enhances chemotaxis (Hayashi et al., 2007) so we tested the effects of the different OPN fragments on B16 cell migration. Compared to BSA, OPN-FL, OPN-R and OPN-R$_{RAA}$ all had increased migration (FIG. 4F). When compared to OPN-FL, chemotaxis was only significantly increased in OPN-R (~3.5-fold), but not in OPN-R$_{RAA}$ or OPN-L, again indicating that both RGD and the cleavage-exposed SVVYGLR (SEQ ID NO:4) at the C-terminus in OPN-R play a role in increasing cell migration. Interestingly OPN-CTF, which does not have either the RGD or the SVVYGLR sequence (SEQ ID NO:4), also showed an increase in cell migration comparable to OPN-FL suggesting that OPN-CTF is functionally active and may interact independently with a different receptor on B16 cells.

Figure 4G:
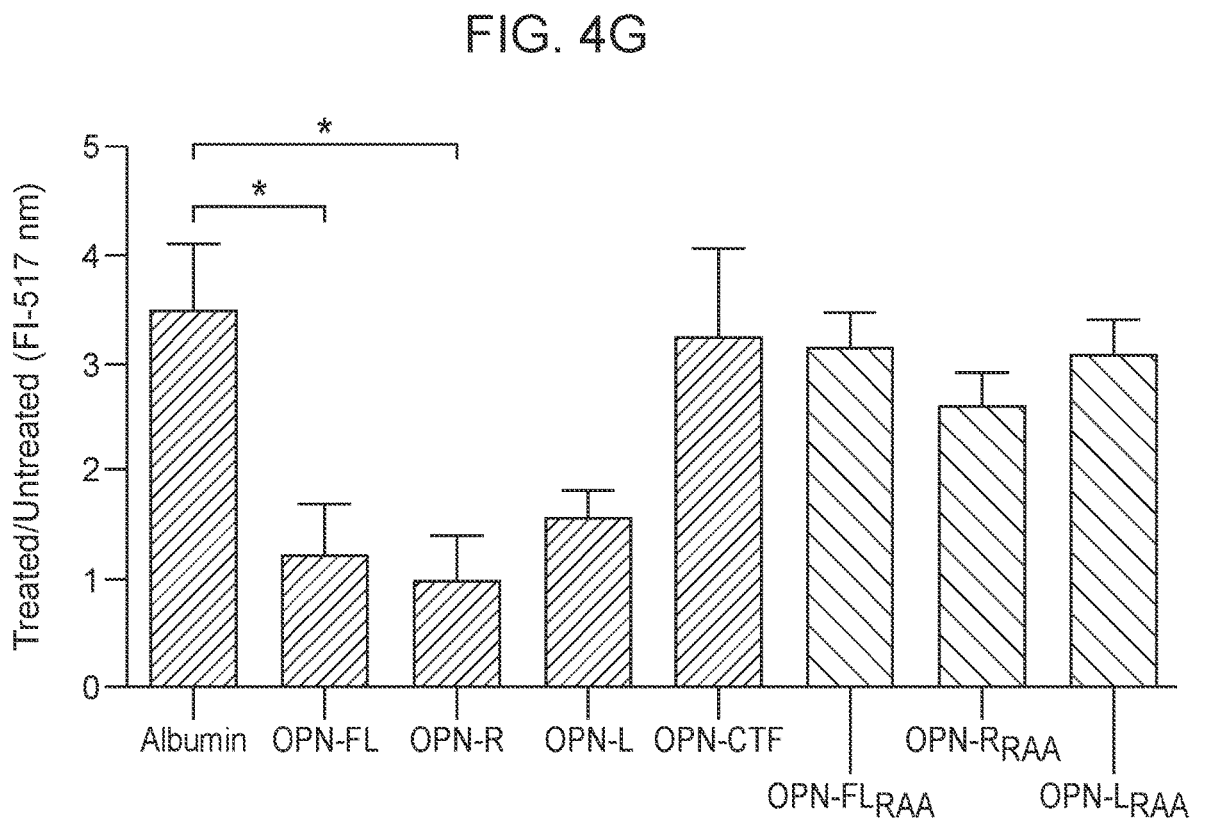

We also studied the effect of OPN and its fragments on B16 cell apoptosis. OPN-FL, OPN-R and OPN-L reduced apoptosis equally by ~3 fold compared to BSA, while OPN-CTF, OPN-FL$_{RAA}$, OPN-R$_{RAA}$ and OPN-L$_{RAA}$ had no anti-apoptotic effect, showing that OPN confers a protective anti-apoptotic effect in B16 cells mediated solely by the RGD site, and is not affected by its cleavage by thrombin (FIG. 4G). Thus, B16 tumor suppression in the OPN-KI mice is not due to the loss of anti-apoptotic effect in OPN$_{R153A}$ resulting in increased tumor cell apoptosis.

Taken together, thrombin-cleaved OPN products modestly affected B16 tumor cell adhesion and chemotaxis. Given the dramatic in vivo phenotype, we hypothesized that thrombin-cleaved fragments also modulate the host-anti-tumor immune response to promote tumor growth and metastases.

B16 Tumors from OPN-KO and OPN-KI Mice Contain More Macrophages

Figure 5A:
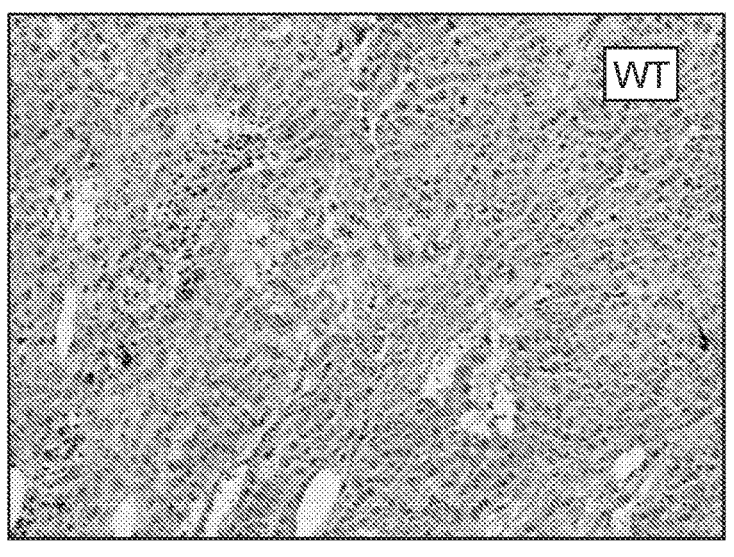
FIGS. 5A-5D: B16 tumors from OPN-KI and OPN-KO mice contain more macrophages.
Figure 5A:
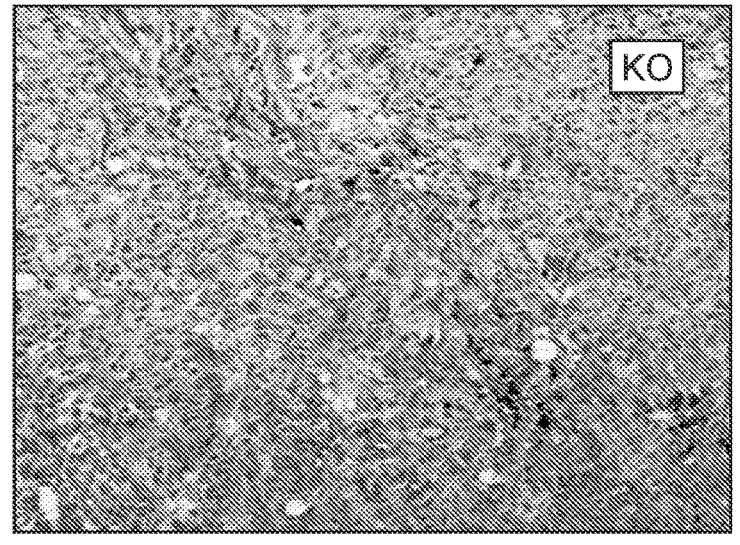
Figure 5A:
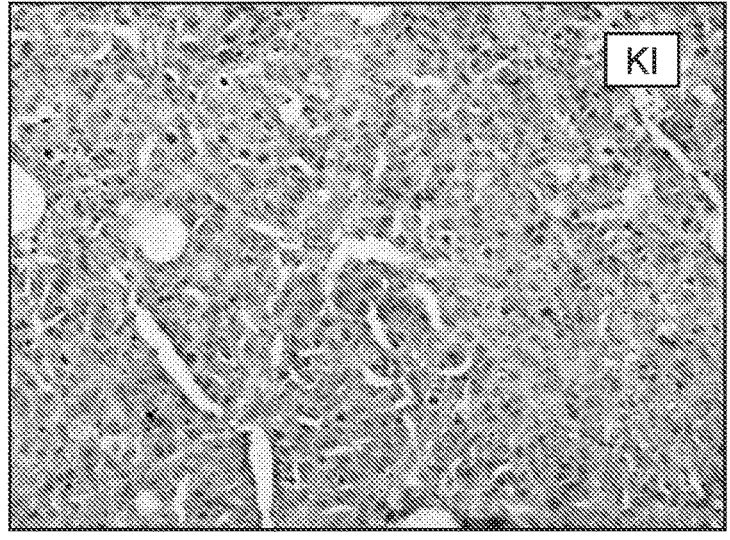
Figures 5B, 5C:
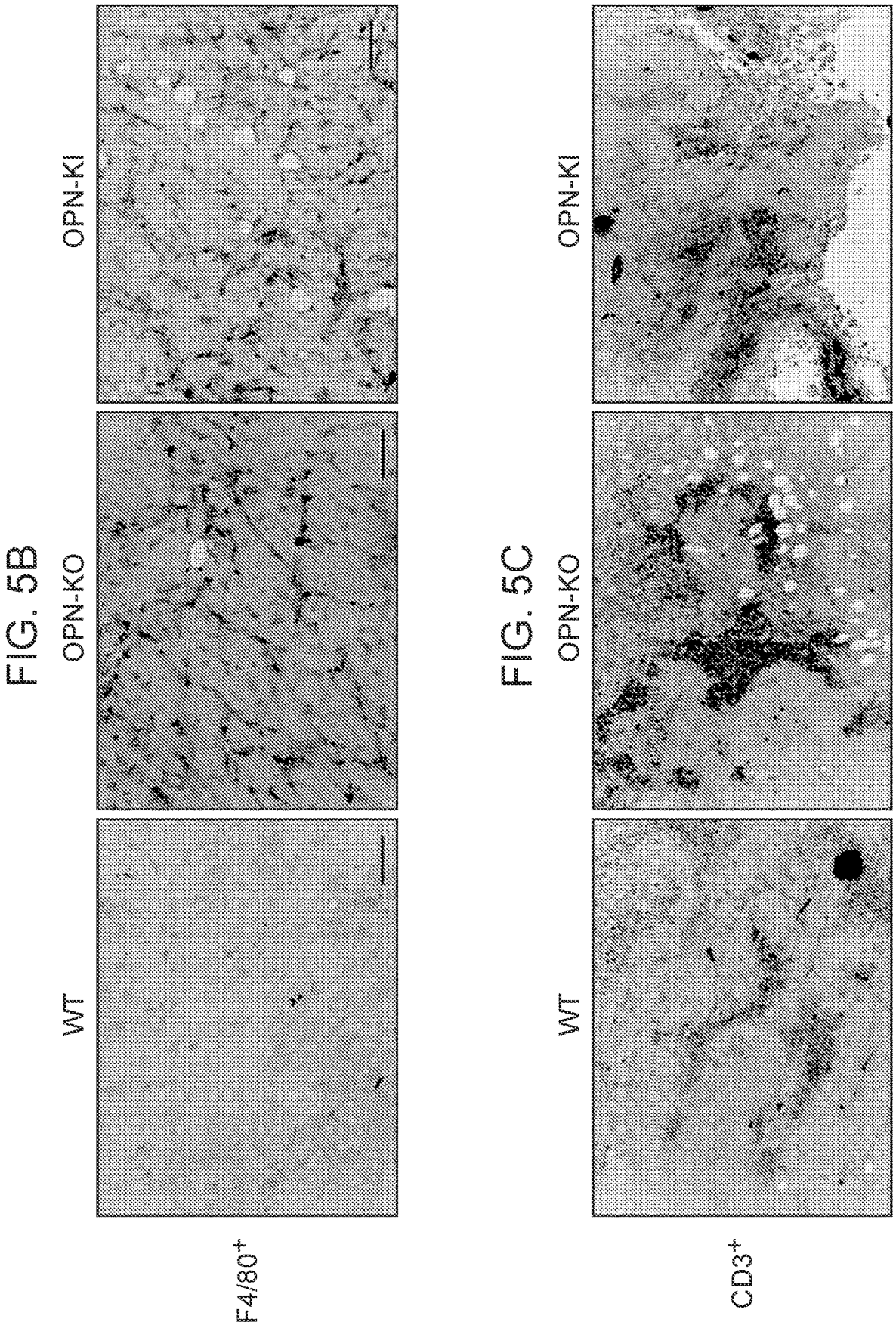

Histological examination did not show significant differences between the B16 tumors from the different mouse genotypes (FIG. 5A). There was no difference in numbers of T cells determined by anti-CD3 antibody in immunohistological studies between B16 tumors grown on the different mouse genotypes (FIG. 5B). However, immunohistological studies and flow cytometric analysis showed significantly more F4/80+ cells in tumors from OPN-KO and OPN-KI than WT mice (FIGS. 5C, 5D) suggesting that the phenotype of tumor suppression might be mediated in part via modulation of the macrophage response.

Figure 6A:
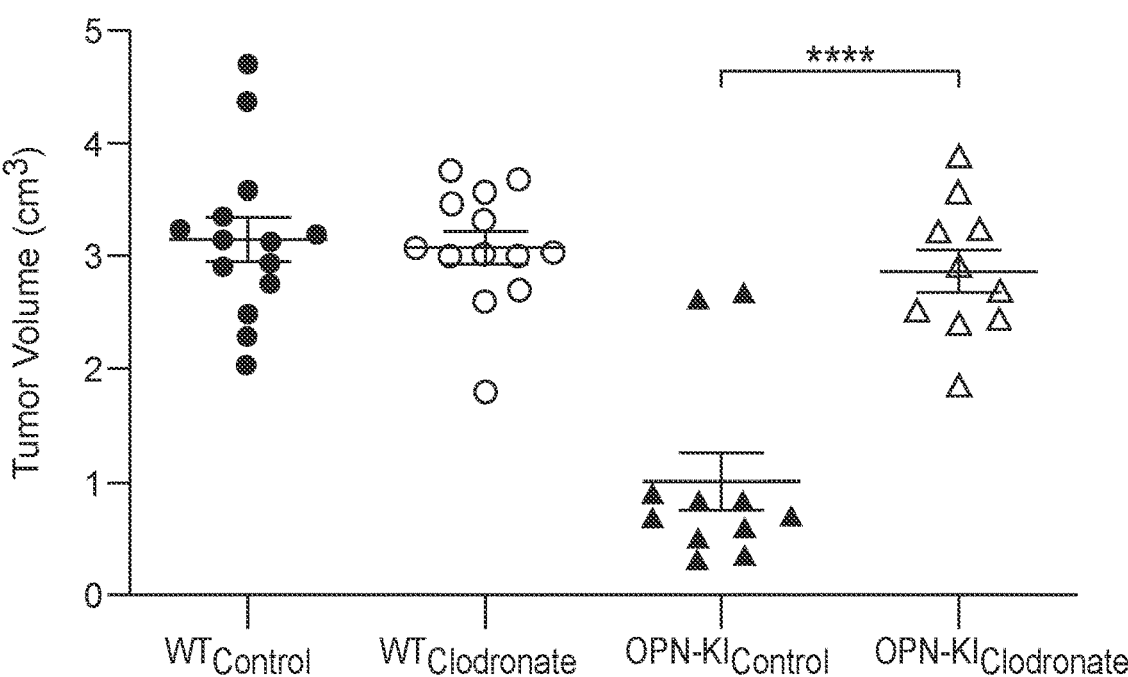
FIGS. 6A-6G: Depletion of macrophages by clodronate reverses the B16 tumor suppression phenotype in OPN-KI mice.
Figure 6B:
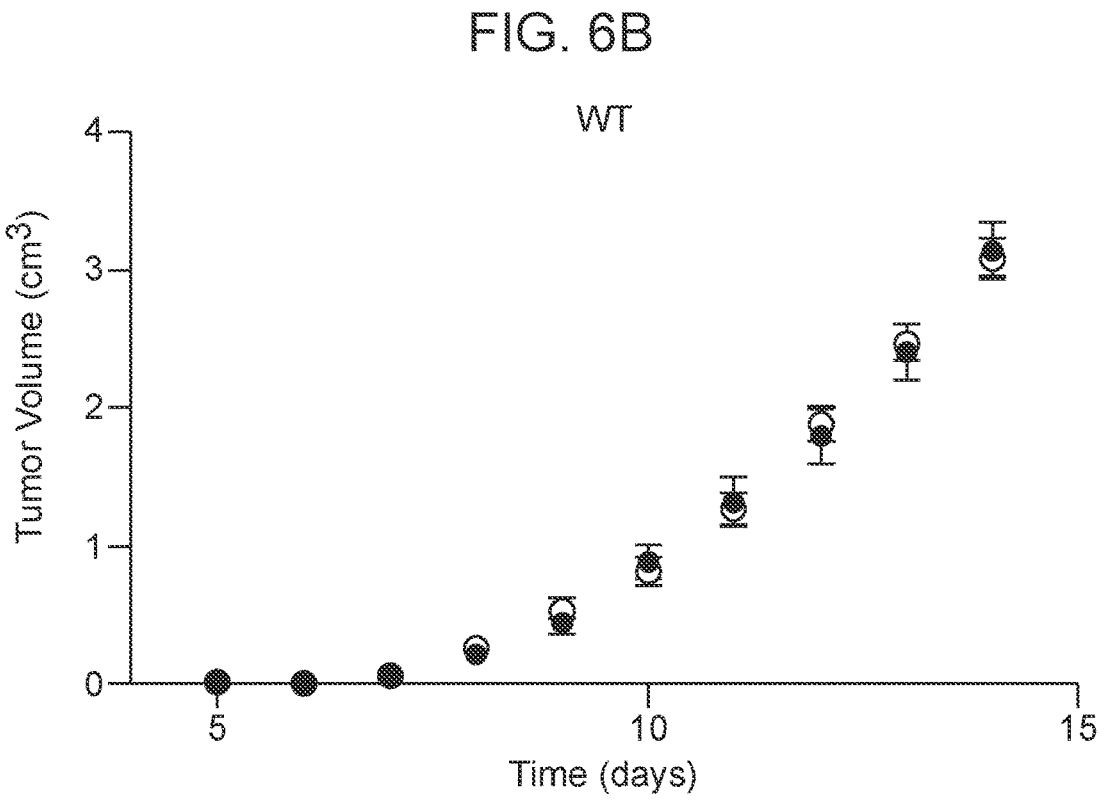
Figure 6C:
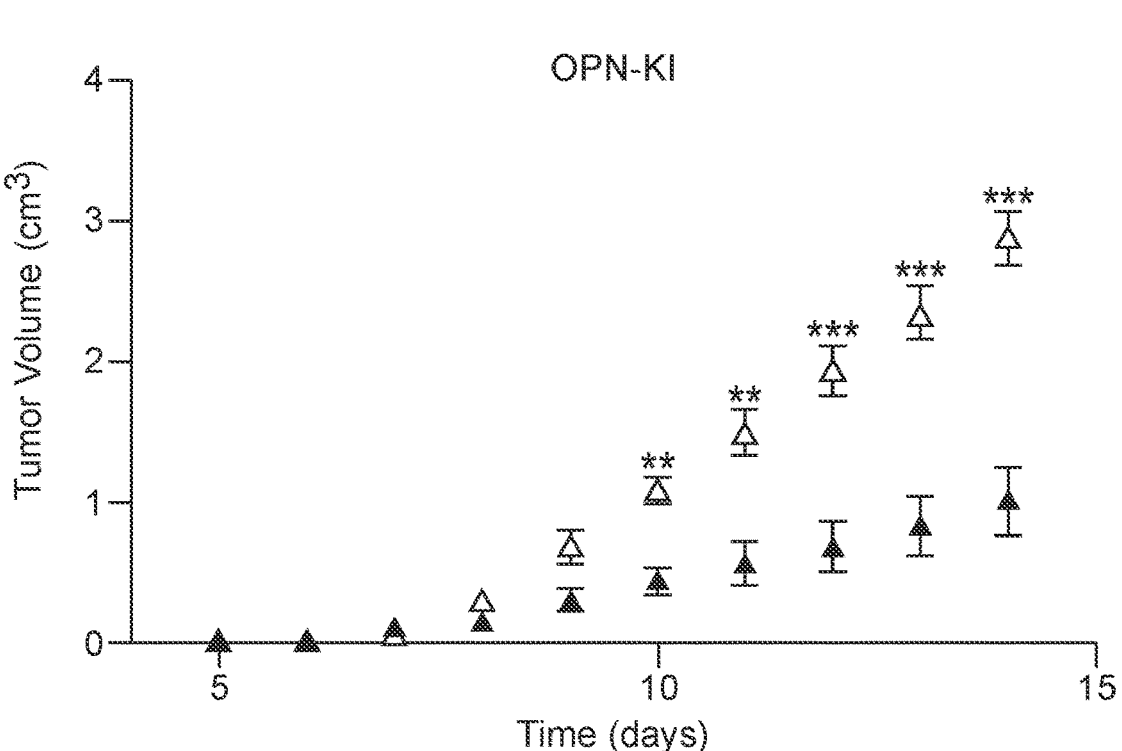
Figure 6D:
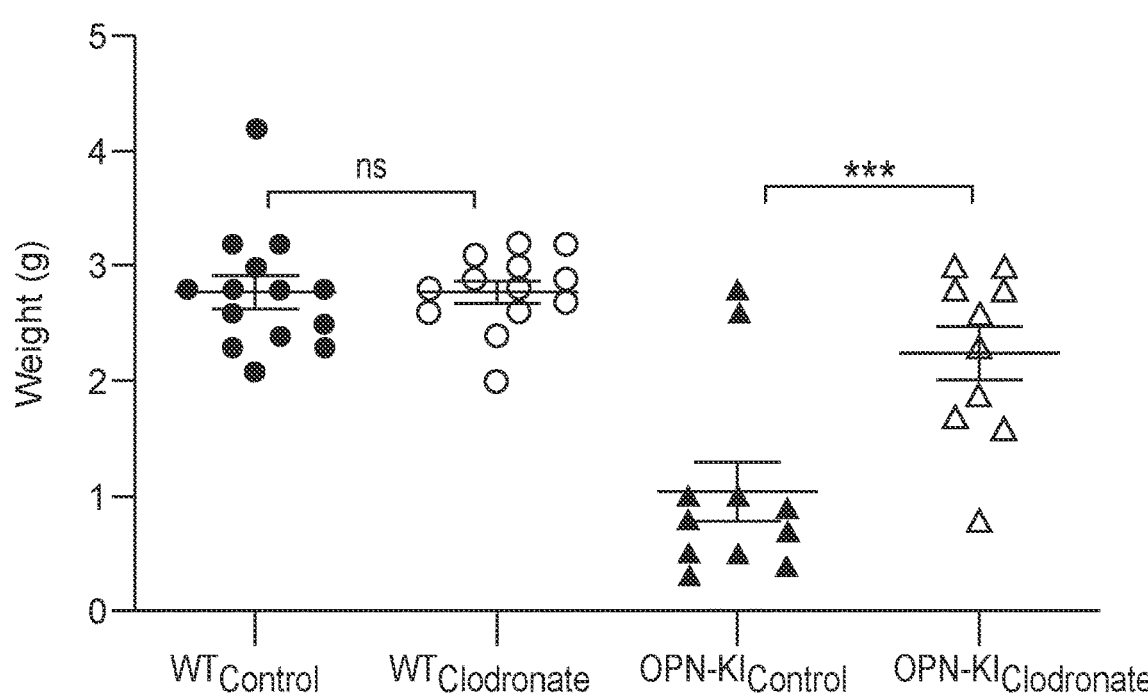
Figure 6E:
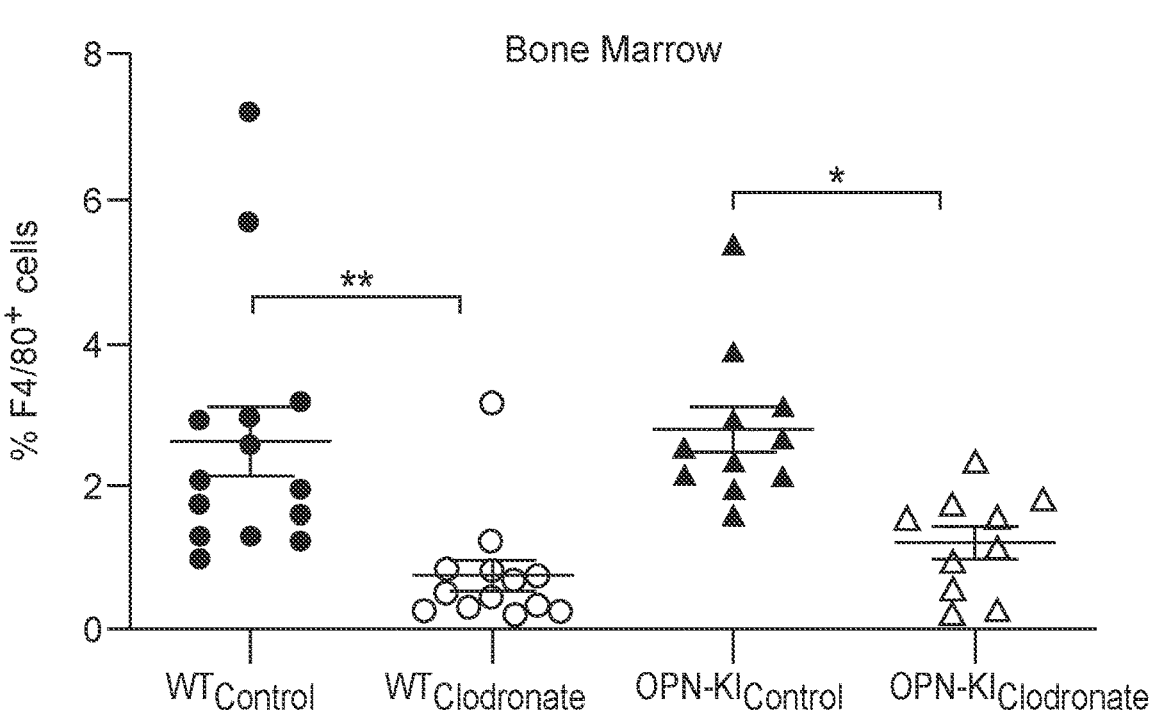
Figure 6F:
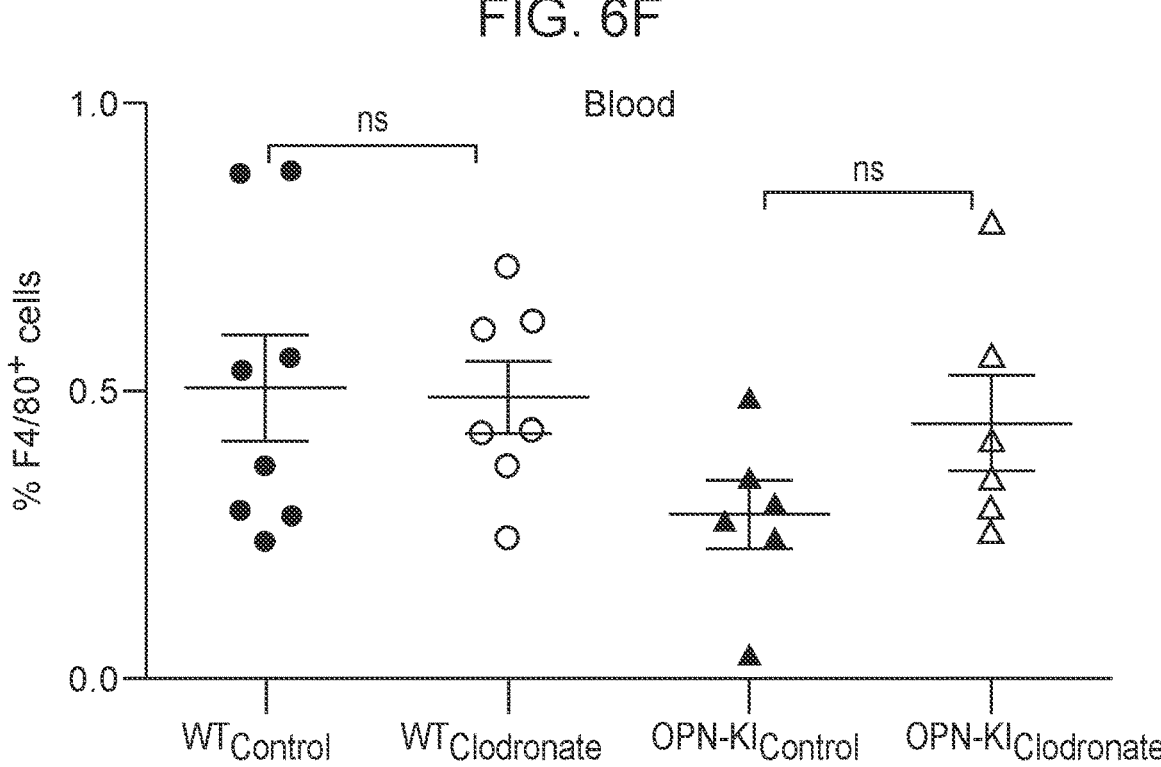
Figure 6G:
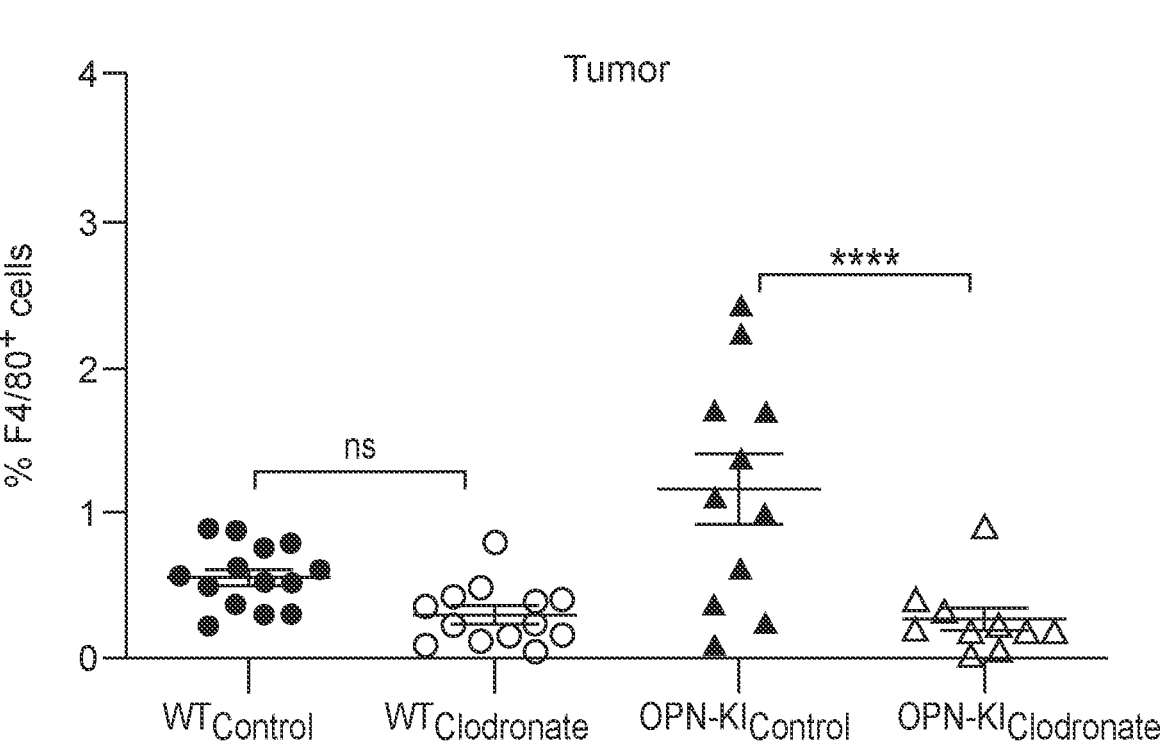

Depletion of Macrophages by Clodronate Reverses the B16 Tumor Suppression Phenotype in OPN-KI Mice Since WT mice tumors had fewer macrophages, we investigated whether tumor suppression in OPN-KI mice is mediated by phagocytes by depleting them with clodronate (Van Rooijen and Sanders, 1994). Treatment with clodronate did not alter B16 tumor growth in WT mice. In OPN-KI mice, macrophage depletion increased B16 tumor volume (clodronate vs. control: 2.88±0.2 cm³; n=10 vs. 1.0±0.25 cm³, p=<0.0001; n=11) similar to WT (clodronate vs. control: 3.1±0.15 cm³; n=13 vs. 3.15±0.2 cm³, p=9930; n=14; FIGS. 6A, 6B) and tumor weight (clodronate vs. control: 2.25±0.23 g vs. 1.0±0.26 g, p=<0.003), similar to levels found in WT mice (clodronate vs. control: 2.8±0.09 g vs. 2.8±0.14 g, p=>0.9999; FIG. 6C). The F4/80+ cell population, a macrophage marker, was reduced in both the bone marrow and tumor compartments of WT and OPN-KI mice treated with clodronate compared to controls while the number of F4/80$^+$ cells in blood was unaffected (FIGS. 6D-6F). This suggests that tumor suppression in OPN-KI mice was due to increased macrophages in the tumors. Although macrophages were depleted by clodronate in WT mice, there was no increase in tumor size.

B16 Tumor Suppression Phenotype is Lost in Immune-Deficient NOG-OPN-KO and NOG-OPN-KI Mice We generated OPN-KO and OPN-KI mice in the severely immunodeficient NOD/Shi-scid/IL-2Rγ$^{null}$ (NOG) mice to create NOG-OPN-KO and NOG-OPN-KI mice respectively (Ito et al., 2002). These mice lack T cells, B cells, NK cells, and exhibit dysfunction of macrophages and dendritic cells. If thrombin-cleaved OPN fragments modulate host anti-tumor immune response, we would expect the tumor suppression phenotype in OPN-KO and OPN-KI mice to be lost in their NOG counterparts. We tested these mice in our B16 tumor and metastasis models.

Figure 7A:
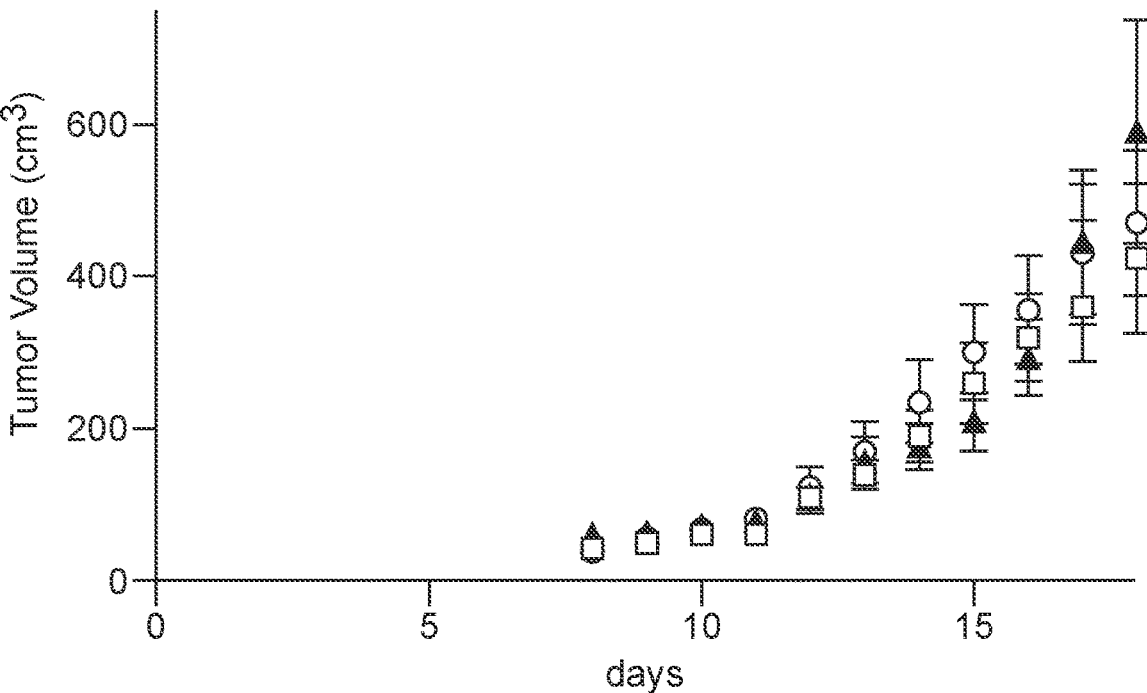
FIGS. 7A-7D: B16 growth in immune-deficient mice is not affected by OPN status.
Figure 7B:
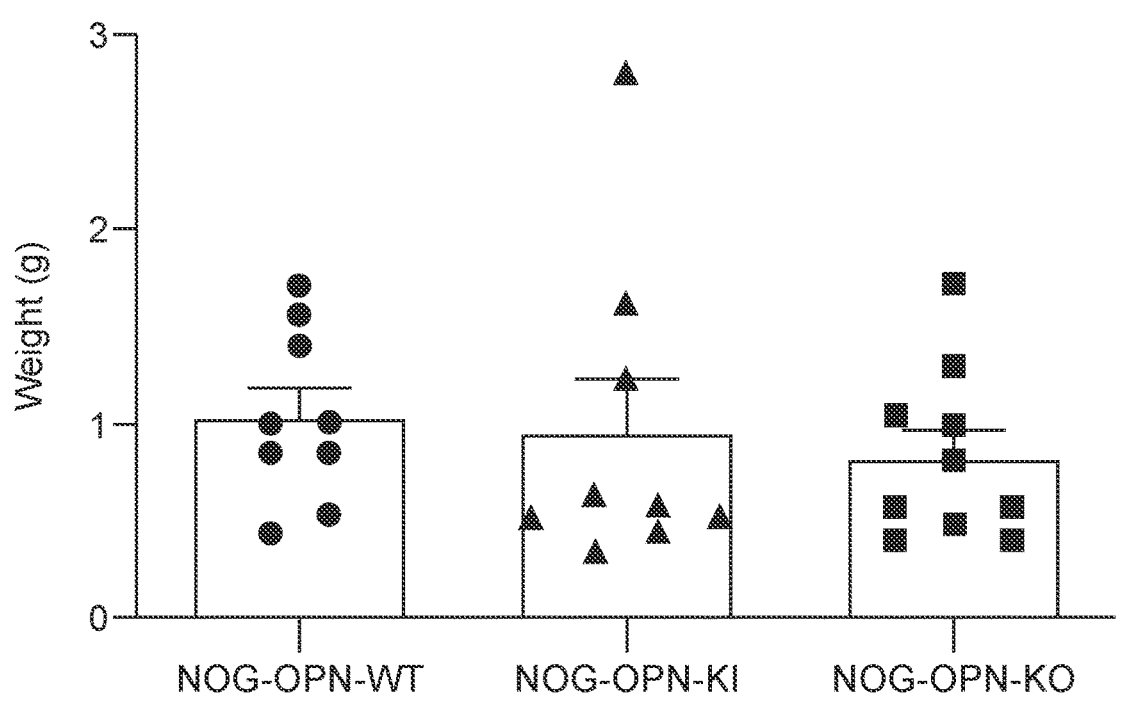
Figure 7C:
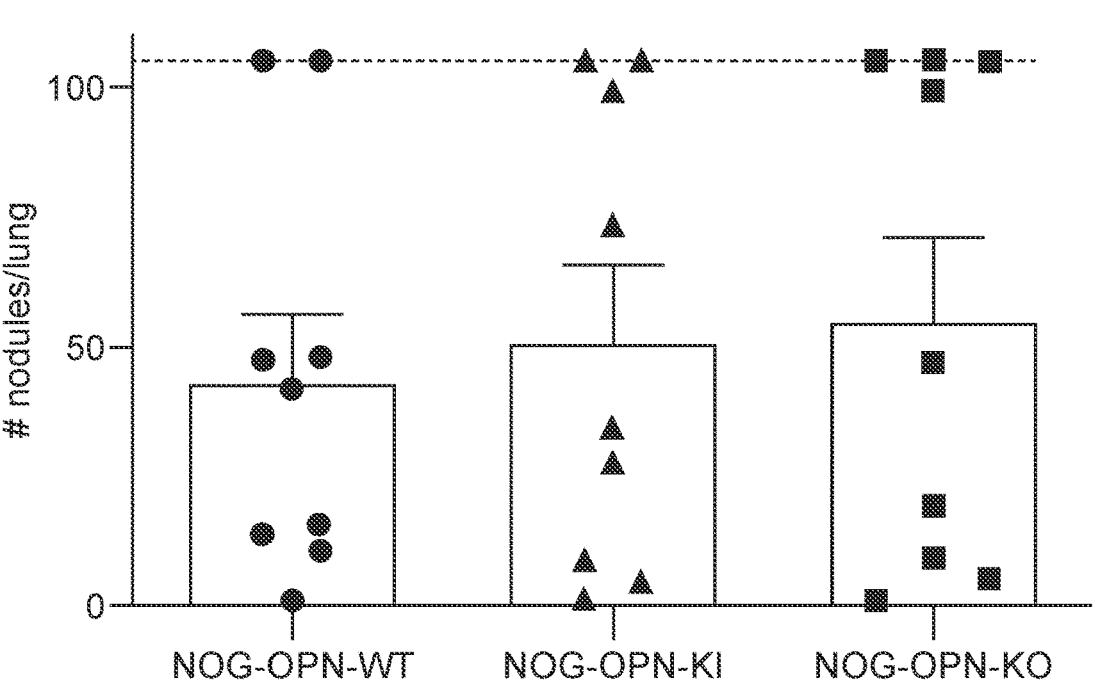
Figure 7D:
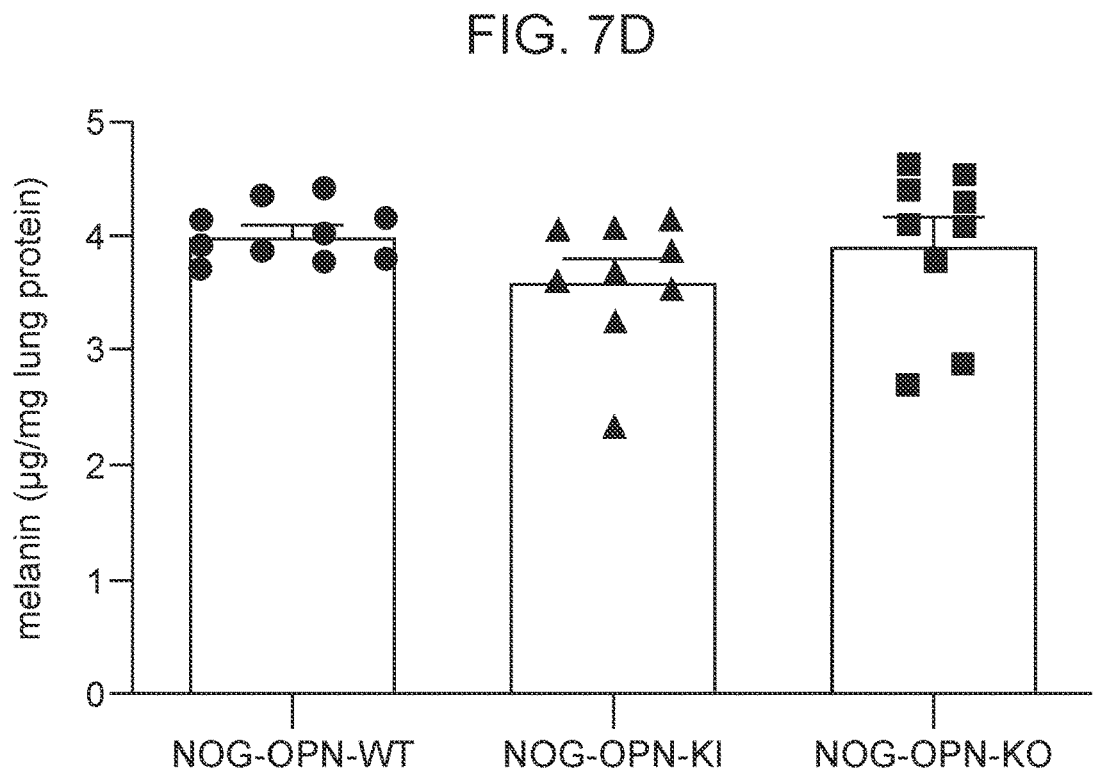

There were no differences in B16 tumor size or weight between NOG control mice, NOG-OPN-KO, and NOG-OPN-KI, even when we titrated the size of B16 inoculum (FIGS. 7A, 7B, FIG. 13). We also found no gender specific differences (FIG. 14). In the pulmonary metastases model, there were no differences in metastatic pulmonary nodules or melanin content between NOG control mice, NOG-OPN-KO, and NOG-OPN-KI mice (FIGS. 7C, 7D). Taken together, tumor suppression in OPN-KI mice requires an intact immune system.

Taken together, the data on the effects of clodronate depletion of macrophages plus that from the NOG immune deficient mice suggest that suppression of B16 tumor growth and metastasis in OPN-KI and OPN-KO mice is due to an enhanced host-anti-tumor immune response mediated by increased F4/80+ tumor-associated macrophages (TAMs).

B16 Tumors from OPN-KO and OPN-KI Mice Contain More Macrophages

To localize this immune effect, we assessed B- and T-cell infiltration of B16 tumors by fluorescence activated cell sorting (FACS) and/or histology and found no significant differences between B16 tumors grown on the different mouse genotypes (FIGS. 7E, 7F). In contrast, immunohistology and flow cytometric analysis demonstrated significantly more macrophages (F4/80$^+$) in tumors from OPN-KO and OPN-KI than WT mice (FIGS. 5B, 5C). Thus, tumor suppression in OPN-KI mice may be mediated by macrophages.

Figure 5D:
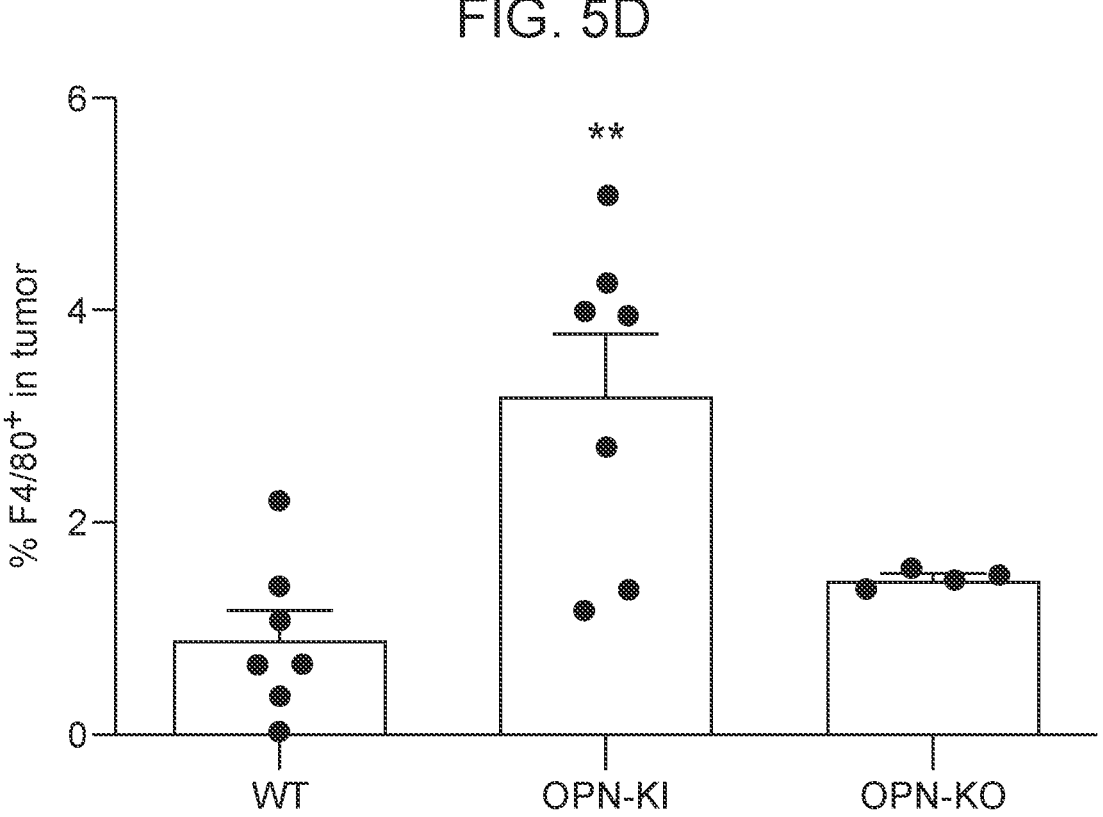

Depletion of Macrophages by Clodronate Reverses the B16 Tumor Suppression Phenotype in OPN-KI Mice To test the hypothesis that tumor suppression in OPN-KI mice is mediated by phagocytes, we depleted them with clodronate (Van Rooijen and Sanders, 1994). Treatment with clodronate did not alter B16 tumor growth in WT mice. In OPN-KI mice, macrophage depletion increased B16 tumor volume (clodronate vs. control: 2.88±0.2 cm$^3$, n=10 vs. 1.0±0.25 cm$^3$, n=11, p=<0.0001) similar to WT (clodronate vs. control: 3.1±0.15 cm$^3$, n=13 vs. 3.15±0.2 cm$^3$, n=14, p=9930; FIGS. 5D, 5E) and tumor weight (clodronate vs. control: 2.25±0.23 g vs. 1.0±0.26 g, p=<0.003), similar to levels found in WT mice (clodronate vs. control: 2.8±0.09 g vs. 2.8±0.14 g, p=>0.9999; FIG. 5F). The F4/80$^+$ cell population, a macrophage marker, was reduced in both the bone marrow and tumor compartments of WT and OPN-KI mice treated with clodronate compared to controls while the number of F4/80$^+$ cells in blood was unaffected (FIGS. 5G-5I). This suggests that tumor suppression in OPN-KI mice was due to increased macrophages in the tumors.

Although macrophages were depleted by clodronate in WT mice, there was no increase in tumor size.

Taken together, the data on the effects of clodronate depletion of macrophages plus that from the NOG immune deficient mice suggest that suppression of B16 tumor growth and metastasis in OPN-KI and OPN-KO mice is due to an enhanced host-anti-tumor immune response mediated by increased F4/80$^+$ tumor-associated macrophages (TAMs).

Figure 8A:
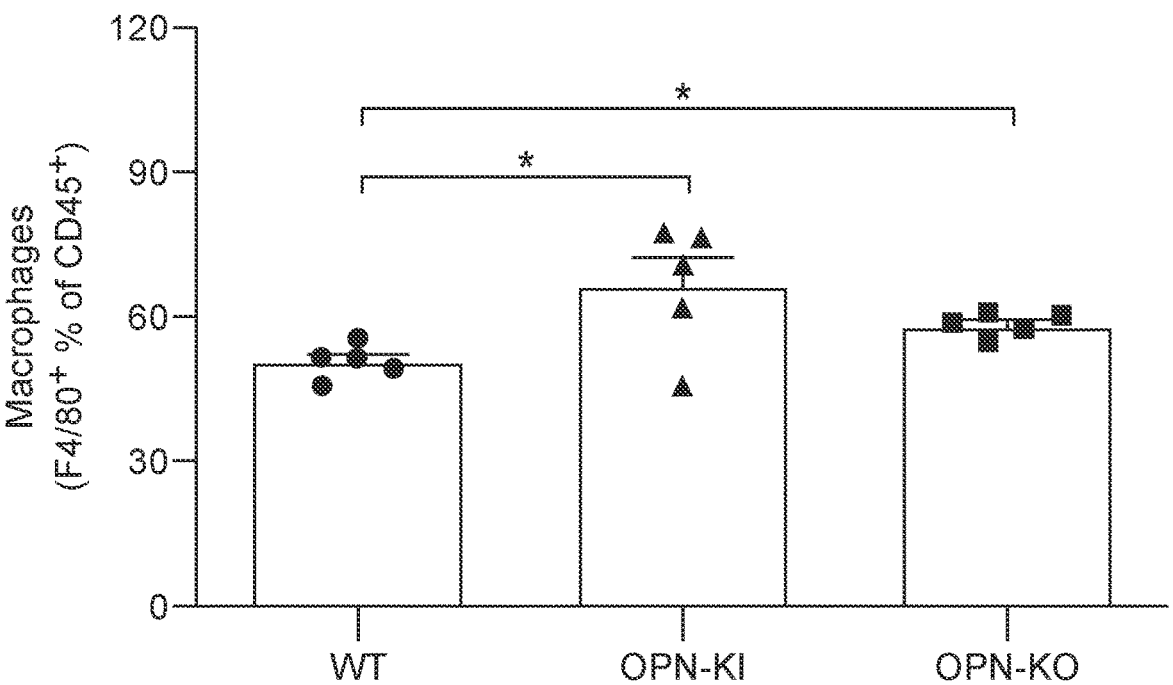
Figure 8B:
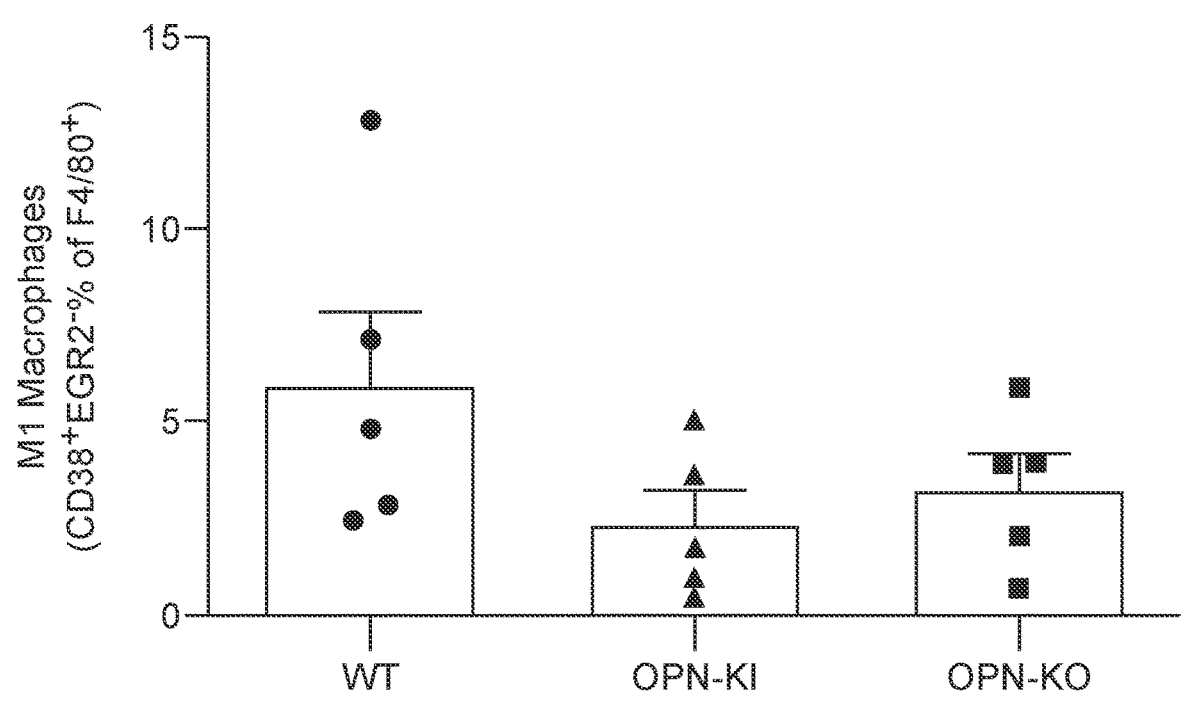
Figure 8C:
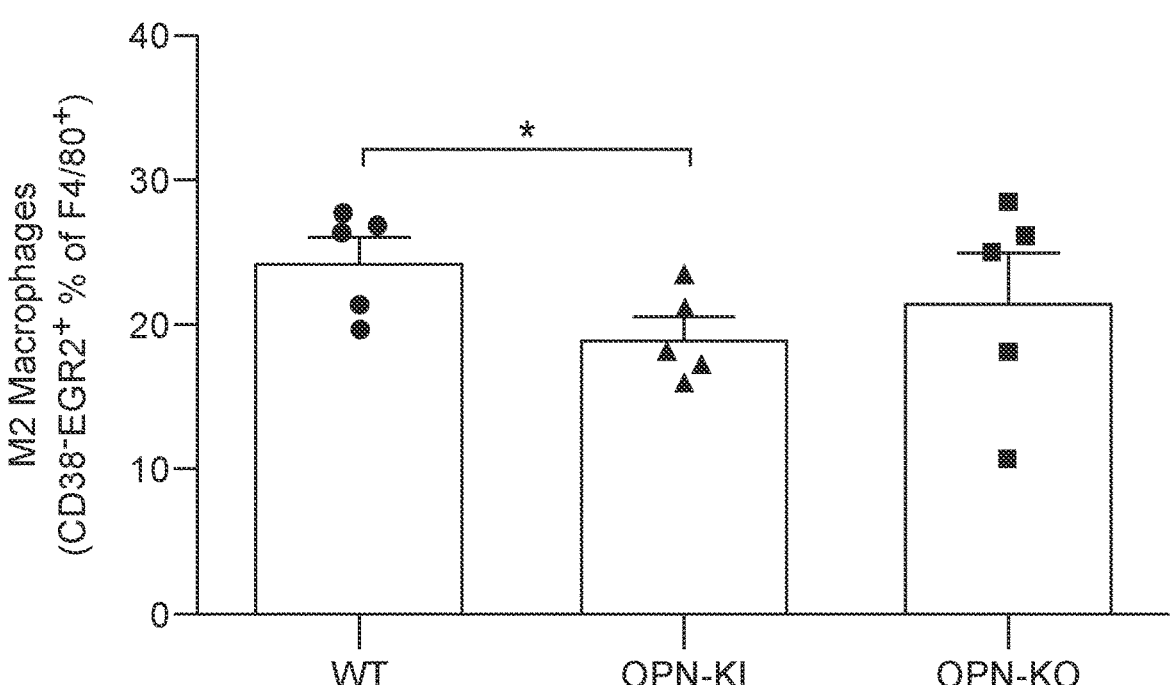
Figure 8D:
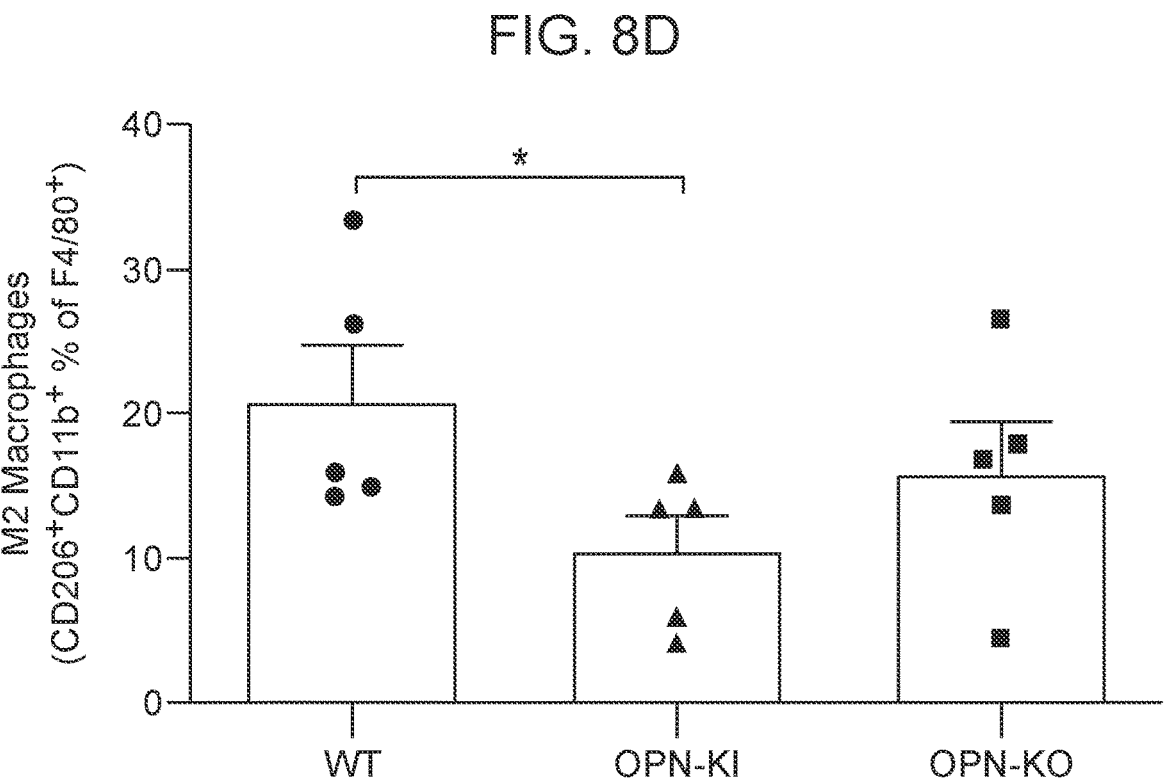
Figure 8E:
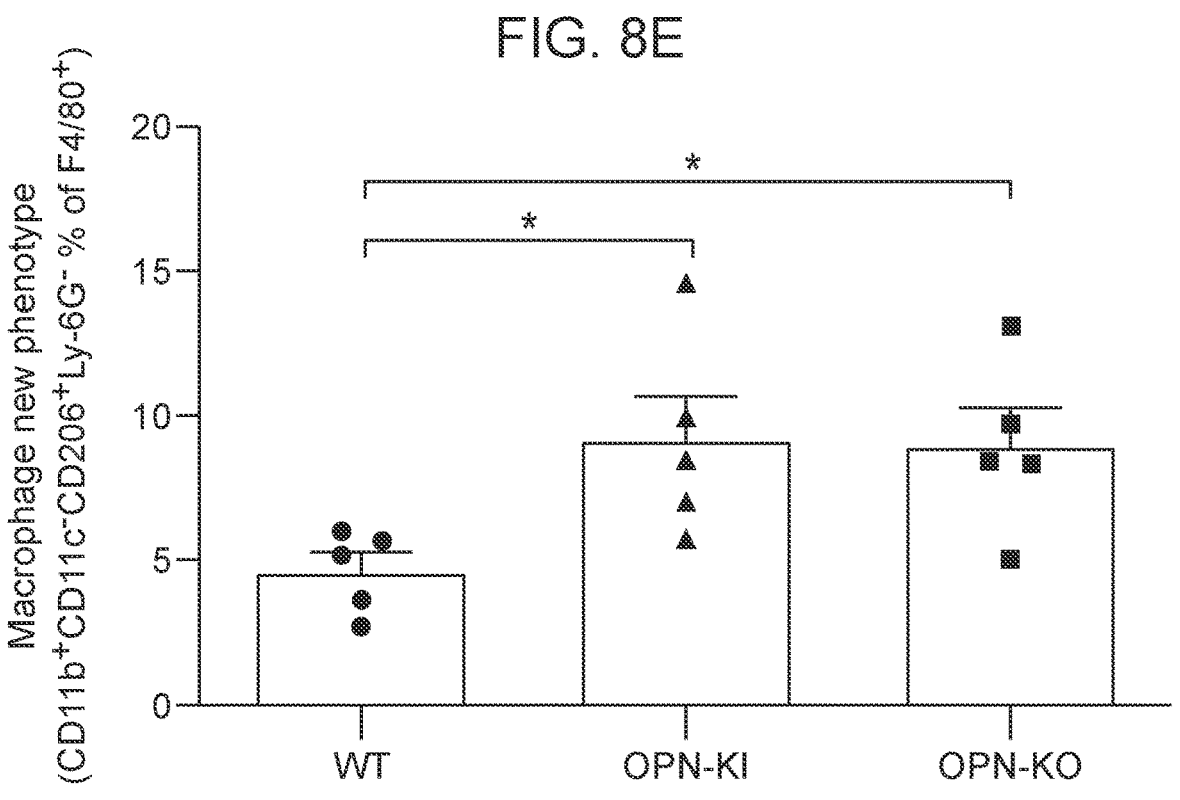
Figure 8F:
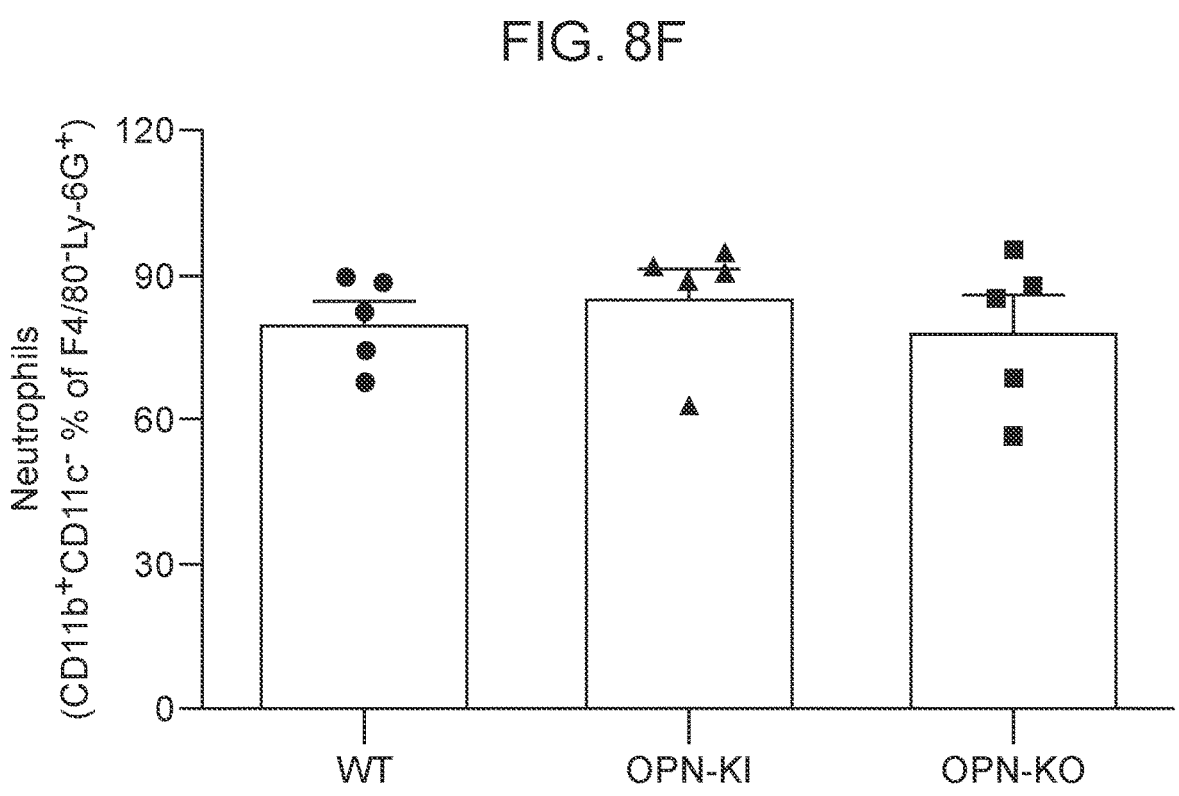
Figure 8G:
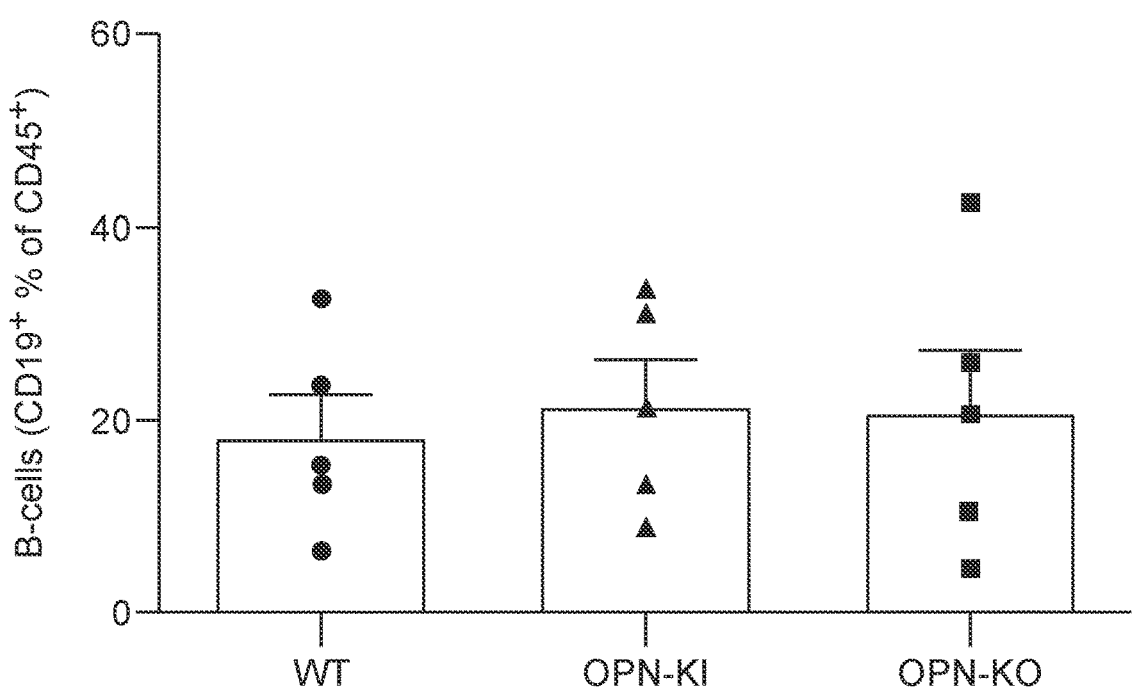
Figure 8H:
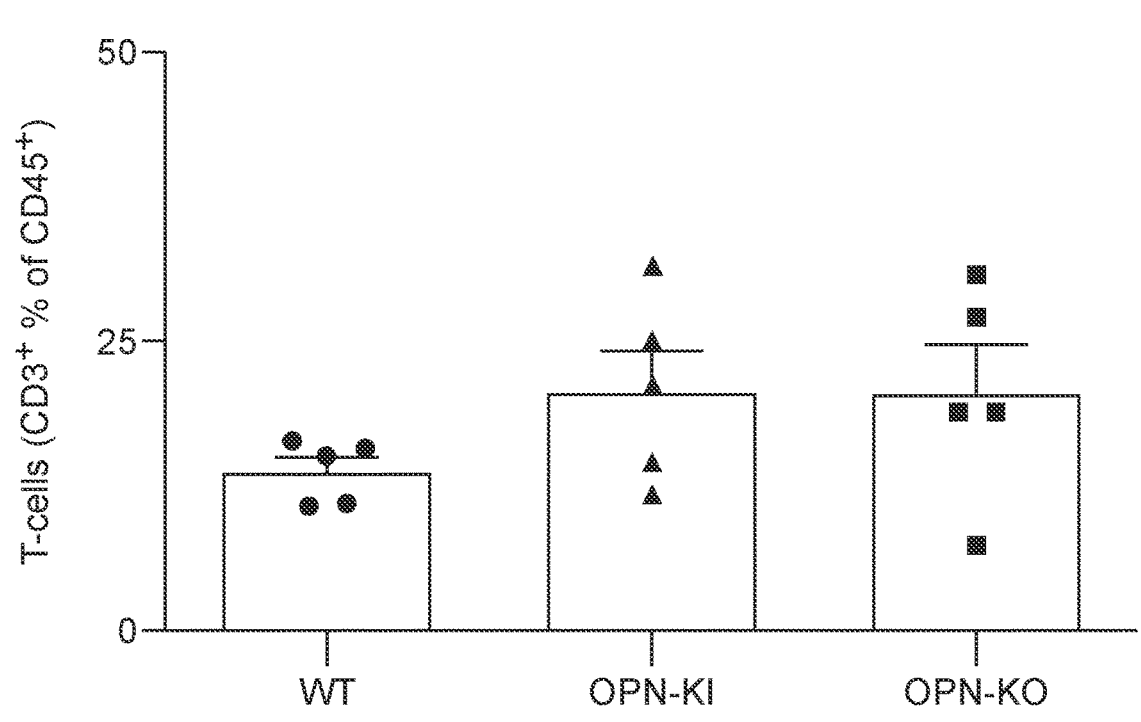
Figure 8I:
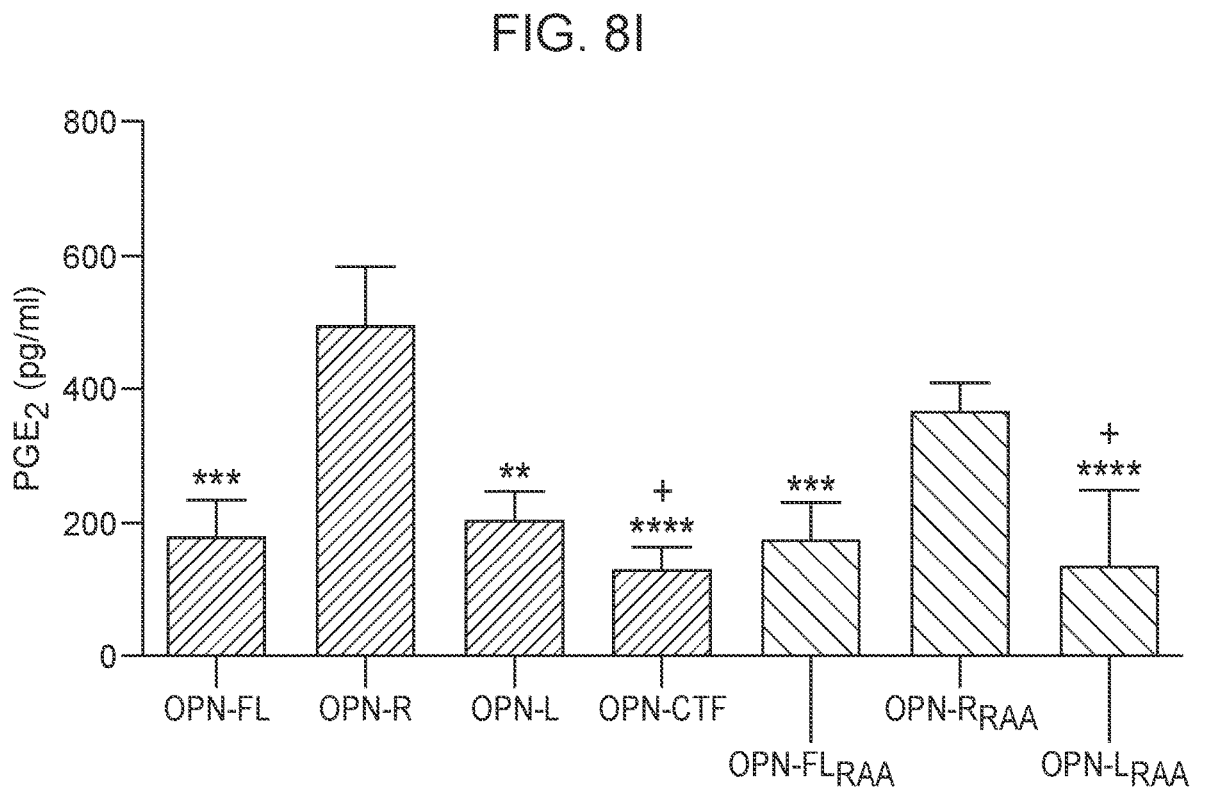
Figure 8J:
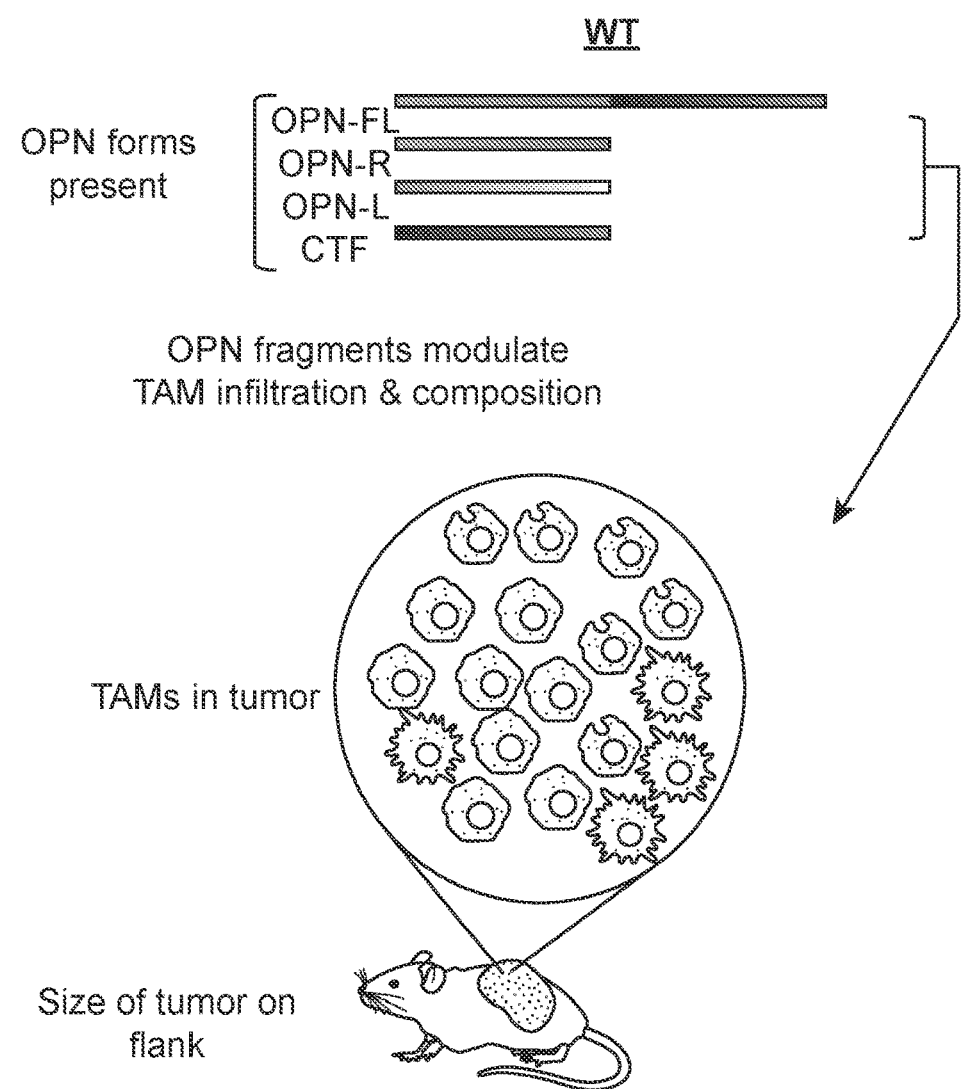
Figure 8J:
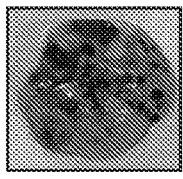
Figure 8J:
Figure 8J:
Figure 8J:
Figure 8J:
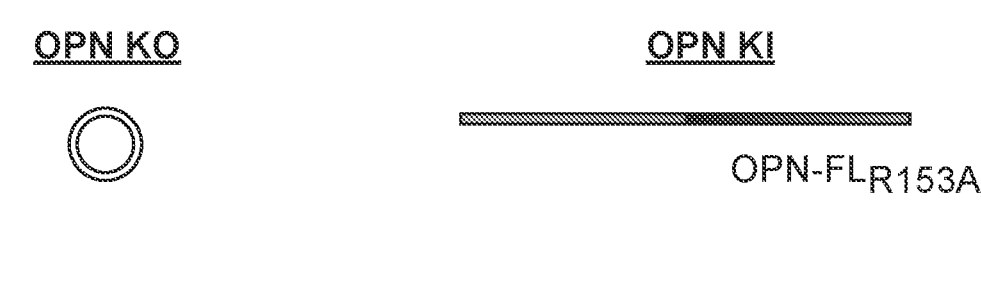
Figure 8J:
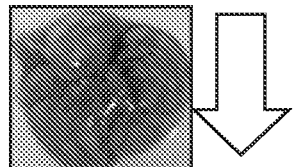
Figure 8J:
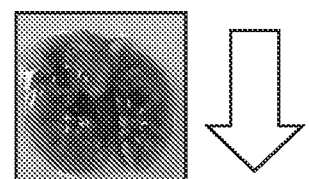
Figure 9A:
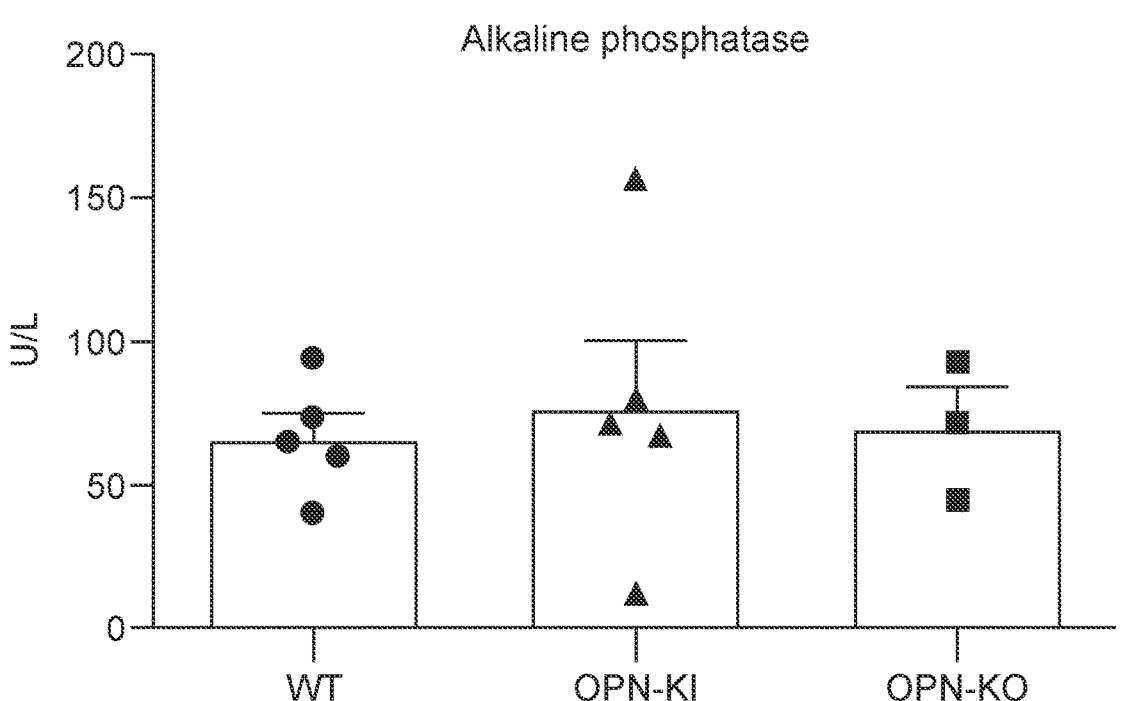
FIGS. 9A-9I: Levels of alkaline phosphatase (FIG. 9A), ALT (FIG. 9B), AST (FIG. 9C), BUN (FIG. 9D), BUN/creatinine ration (FIG. 9E), cholesterol (FIG. 9F), creatinine (FIG. 9G), lactate dehydrogenase (LDH.
Figure 9B:
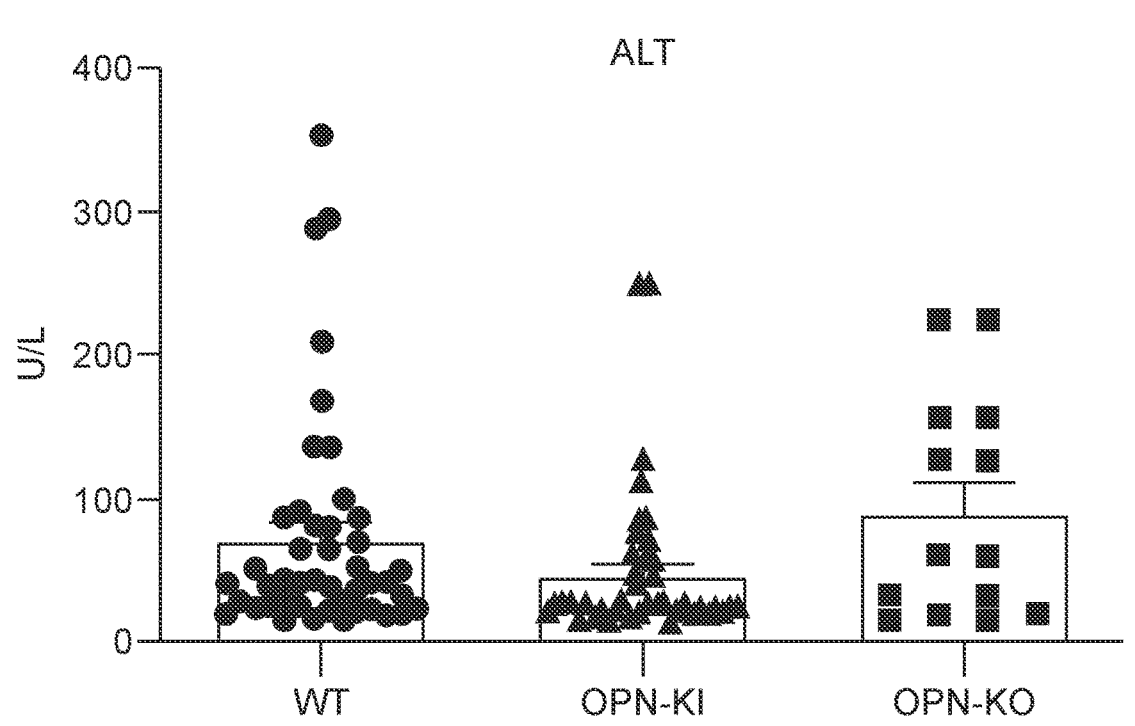
Figure 9C:
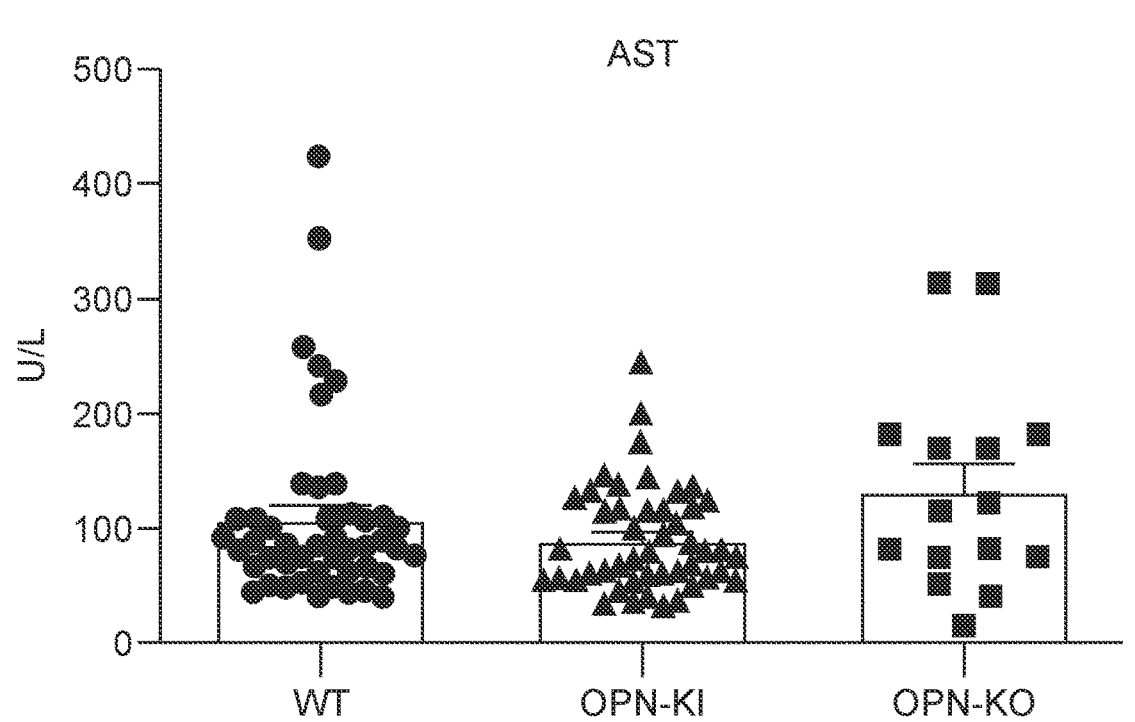
Figure 9D:
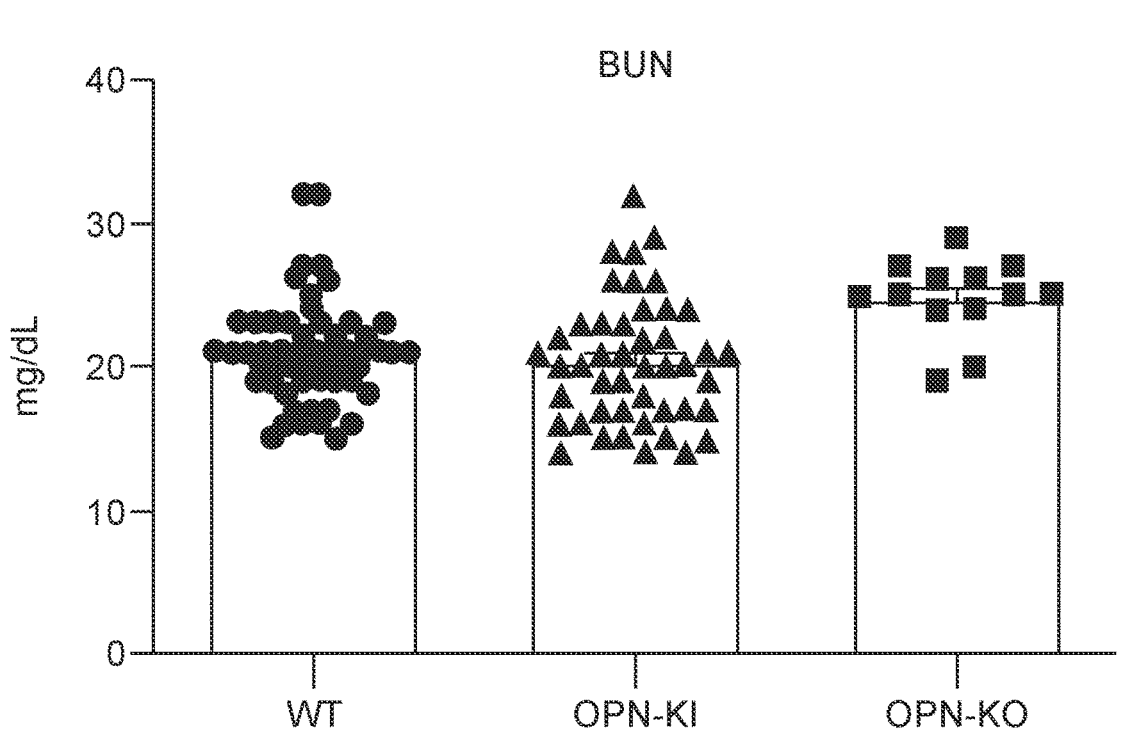
Figure 9E:
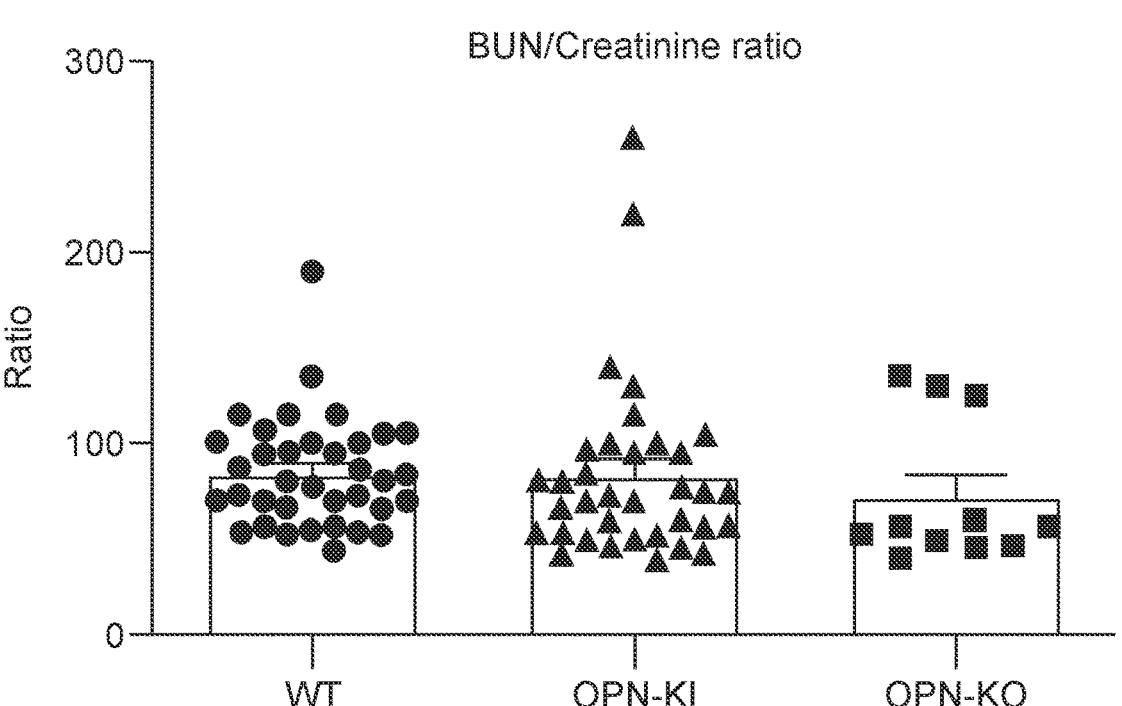
Figure 9F:
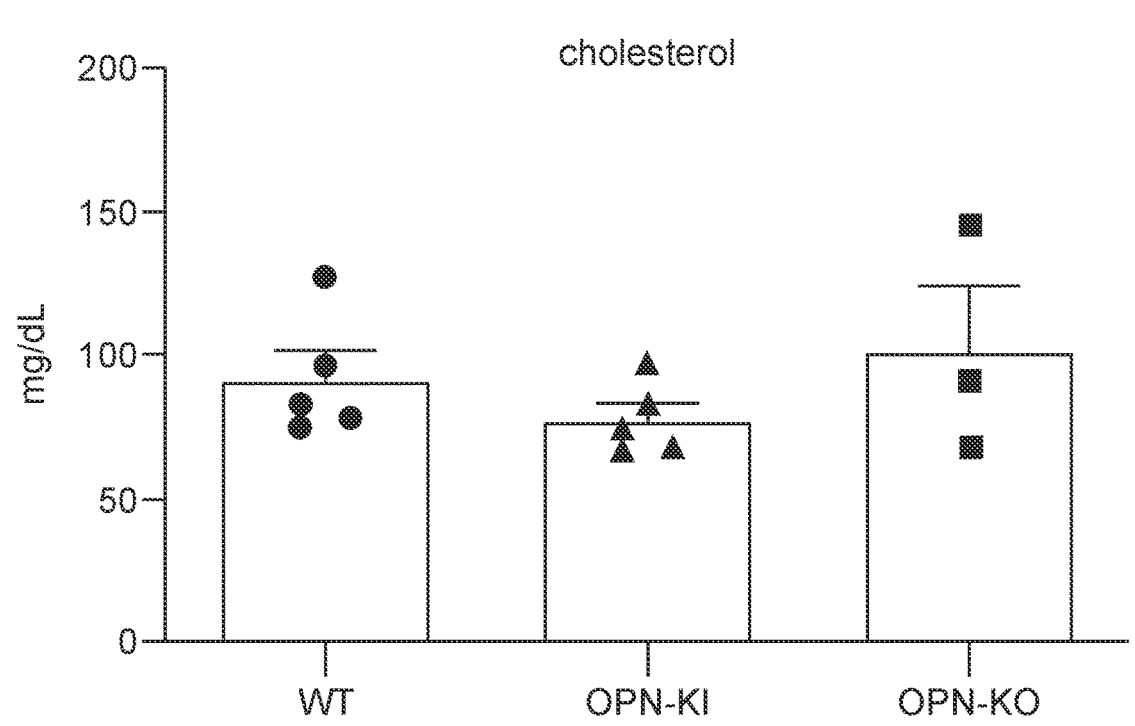
Figure 9G:
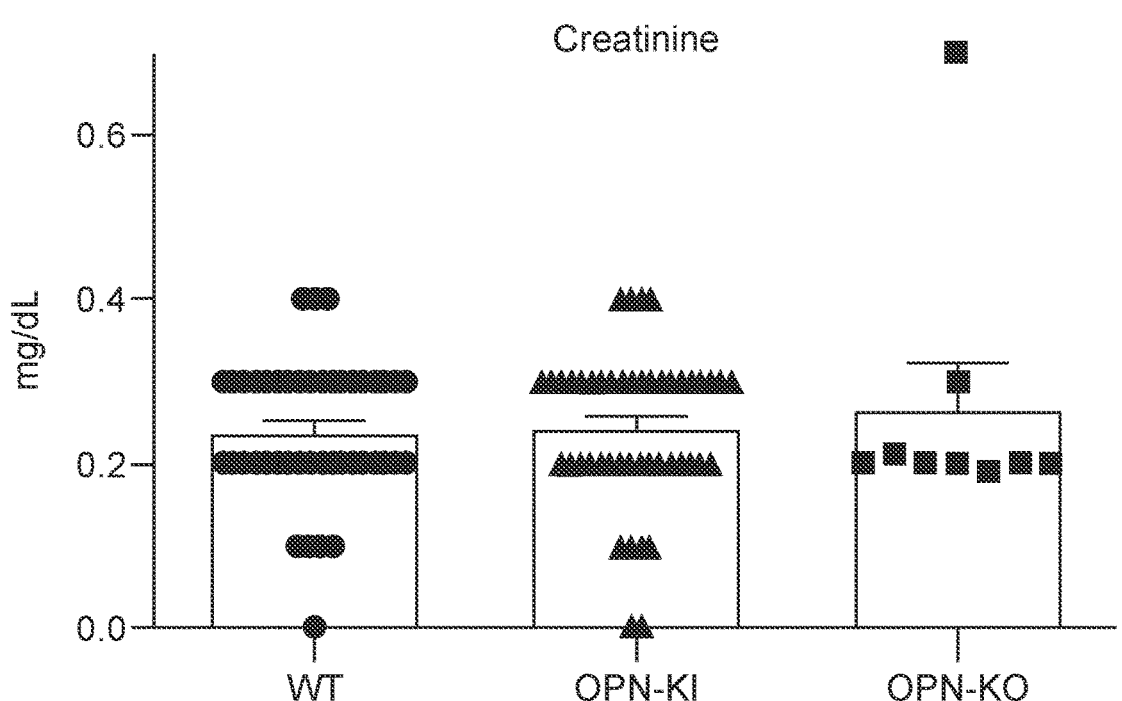
Figure 9H:
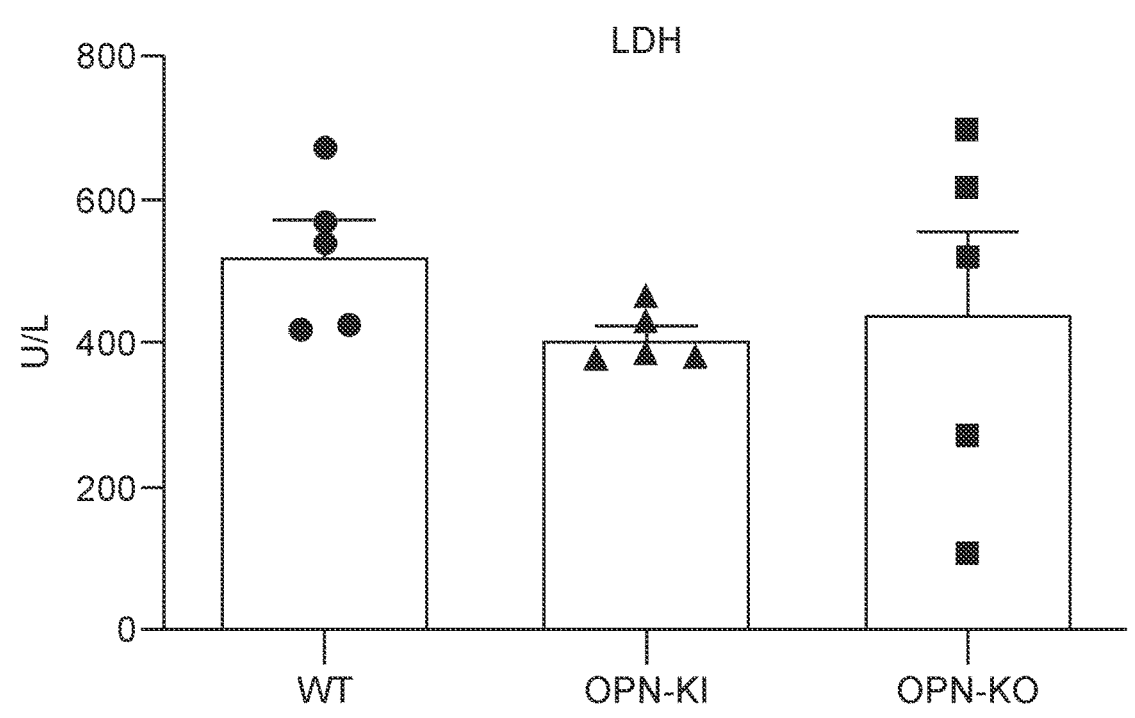
Figure 9I:
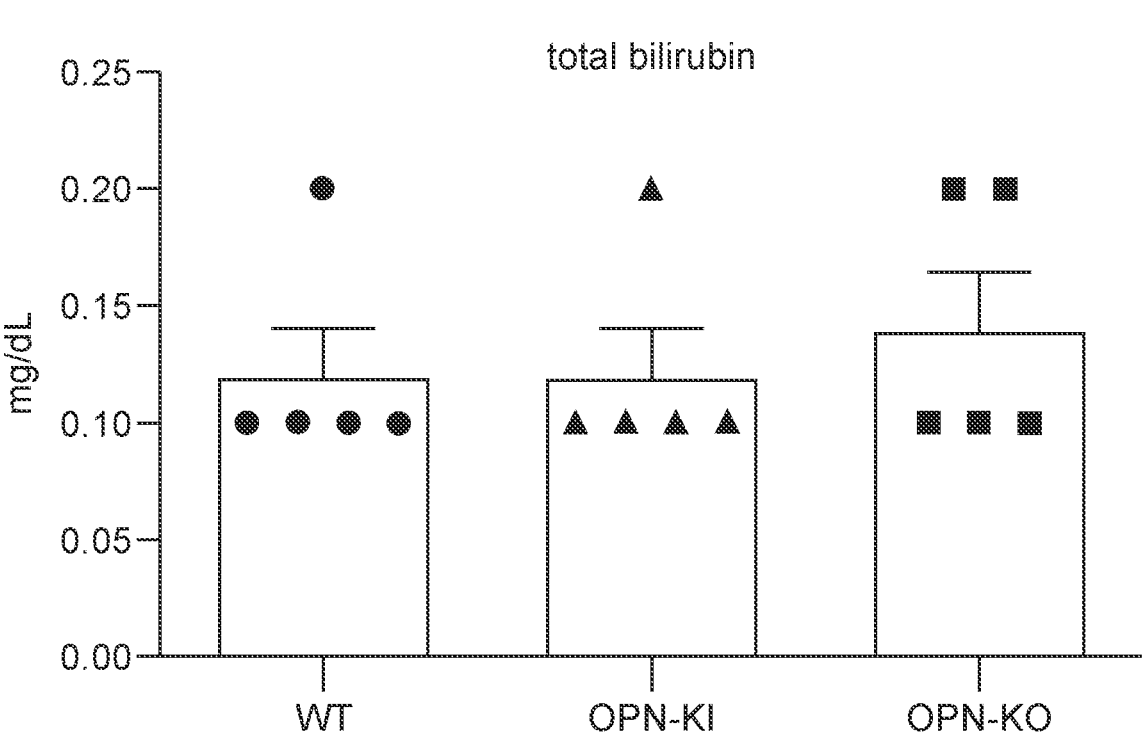
Figure 10A:
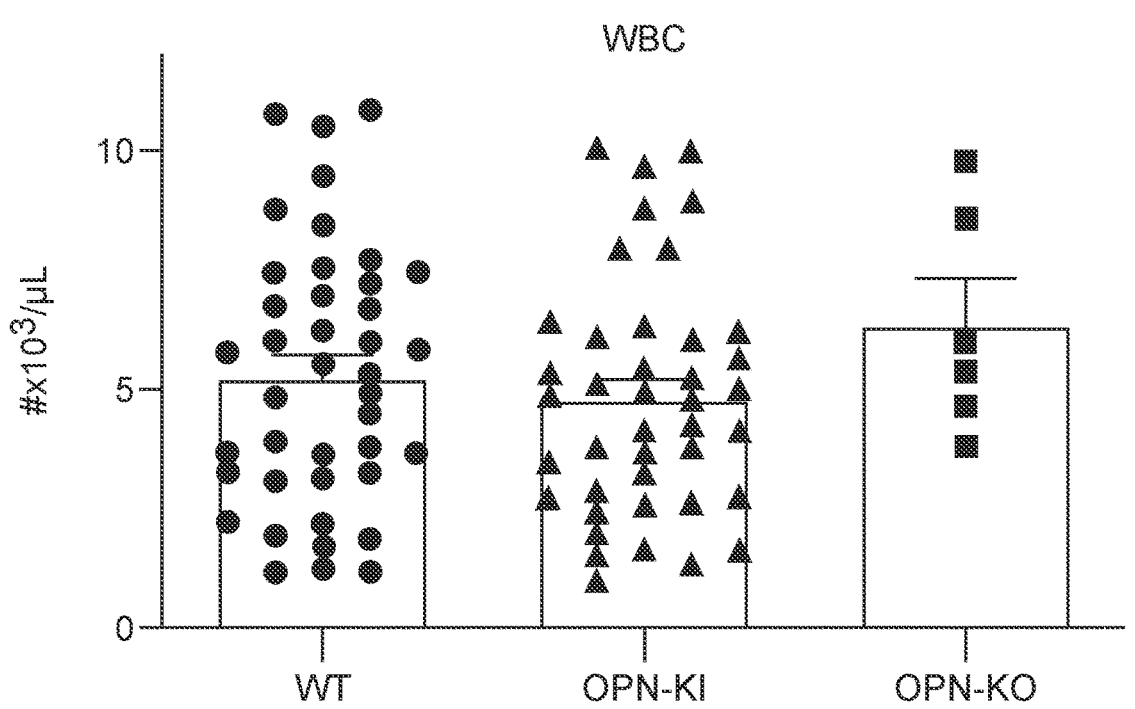
FIGS. 10A-10H: Blood cell counts from WT, OPN-KI and OPN-KO mice. Numbers of WBCs (FIG. 10A), lymphocytes (FIG. 10B), monocytes (FIG. 10C), neutrophils (FIG. 10D), platelets (FIG. 10E), RBCs (FIG. 10F), reticulocytes (FIG. 10G) and level of hemoglobin (Hgb.
Figure 10B:
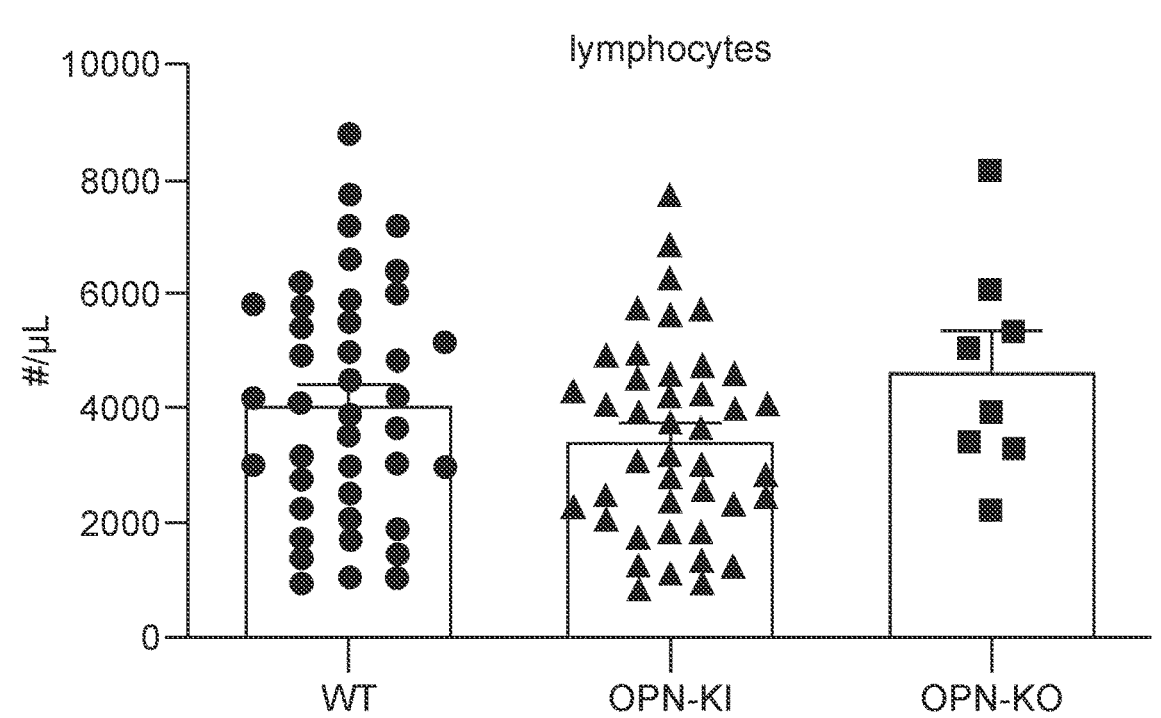
Figure 10C:
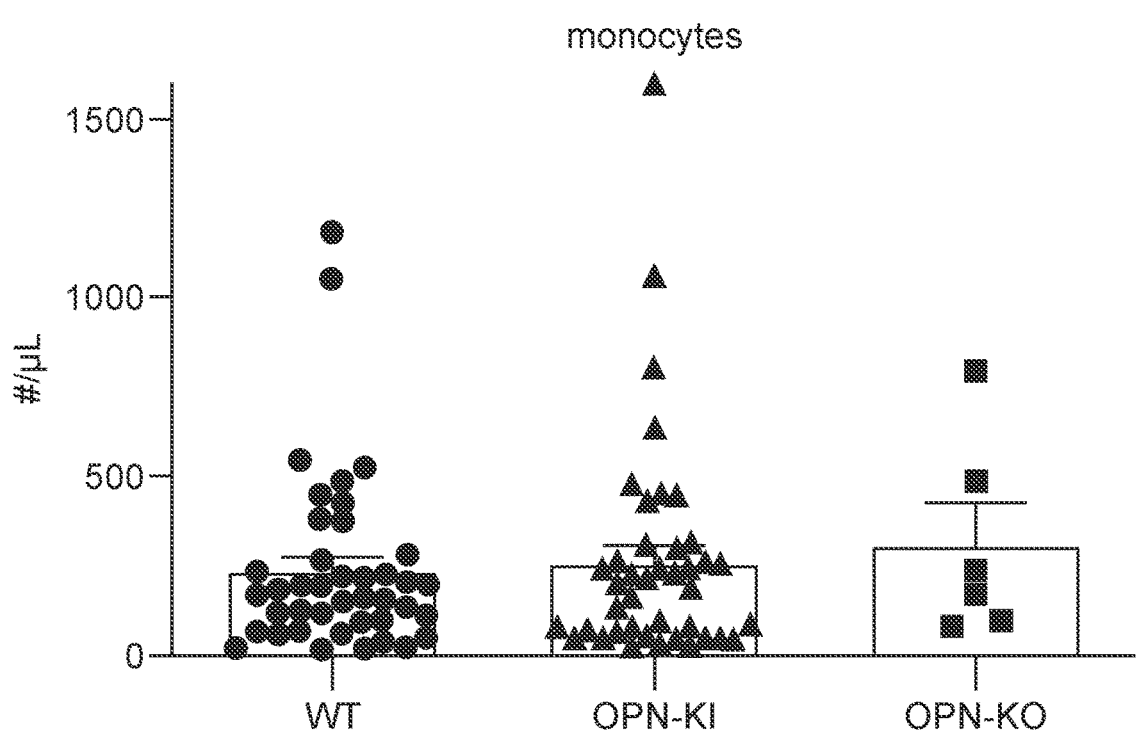
Figure 10D:
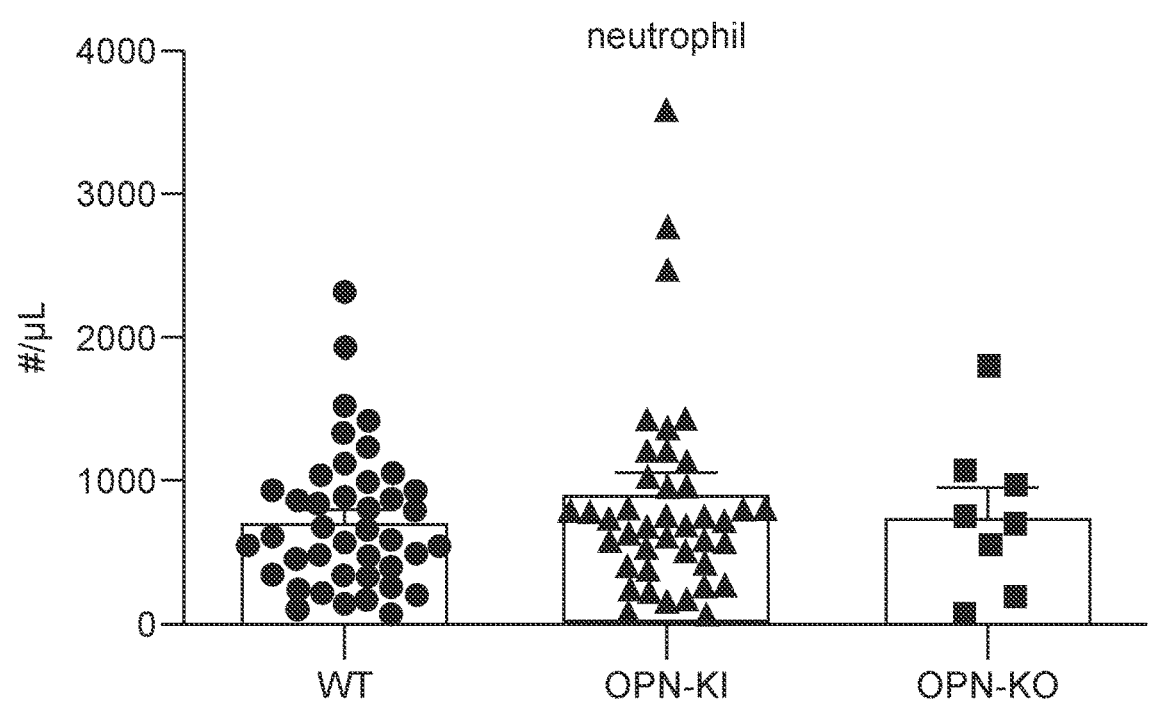
Figure 10E:
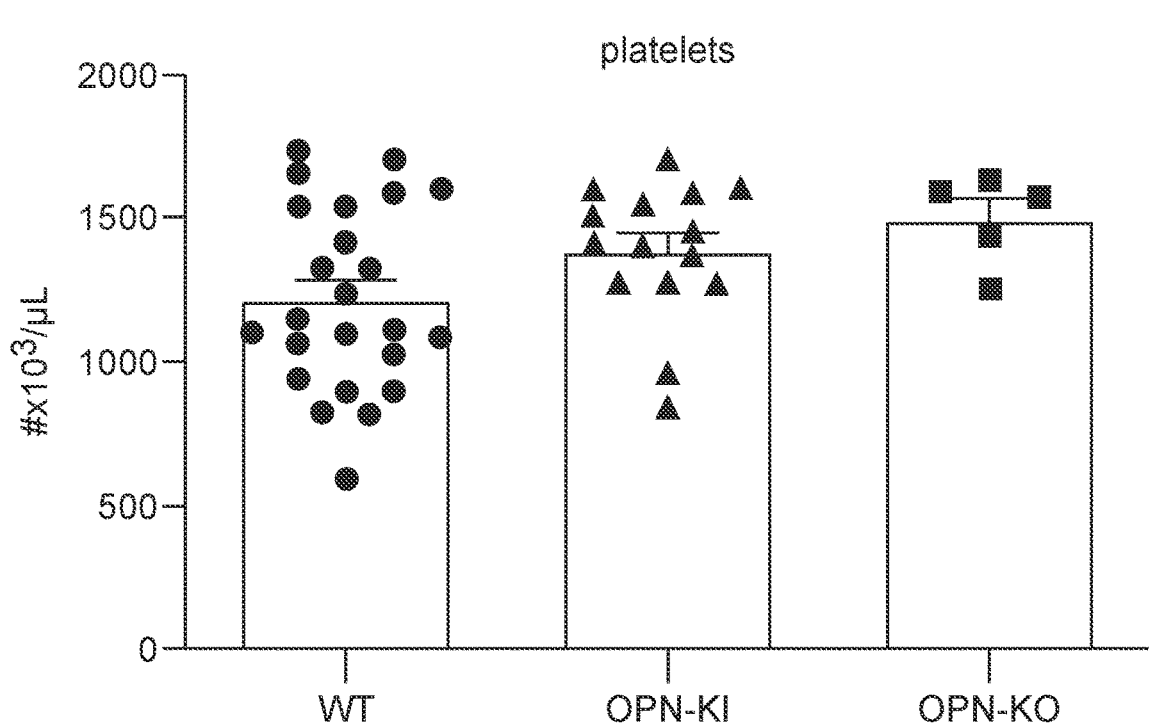
Figure 10F:
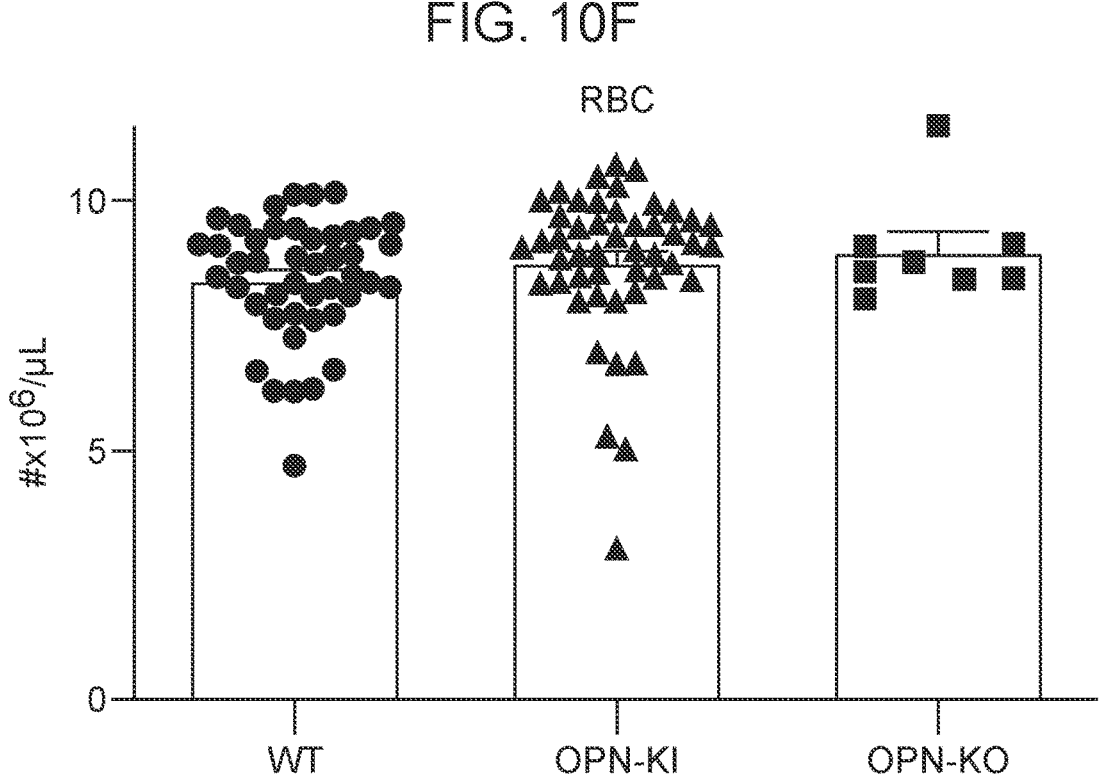
Figure 10G:
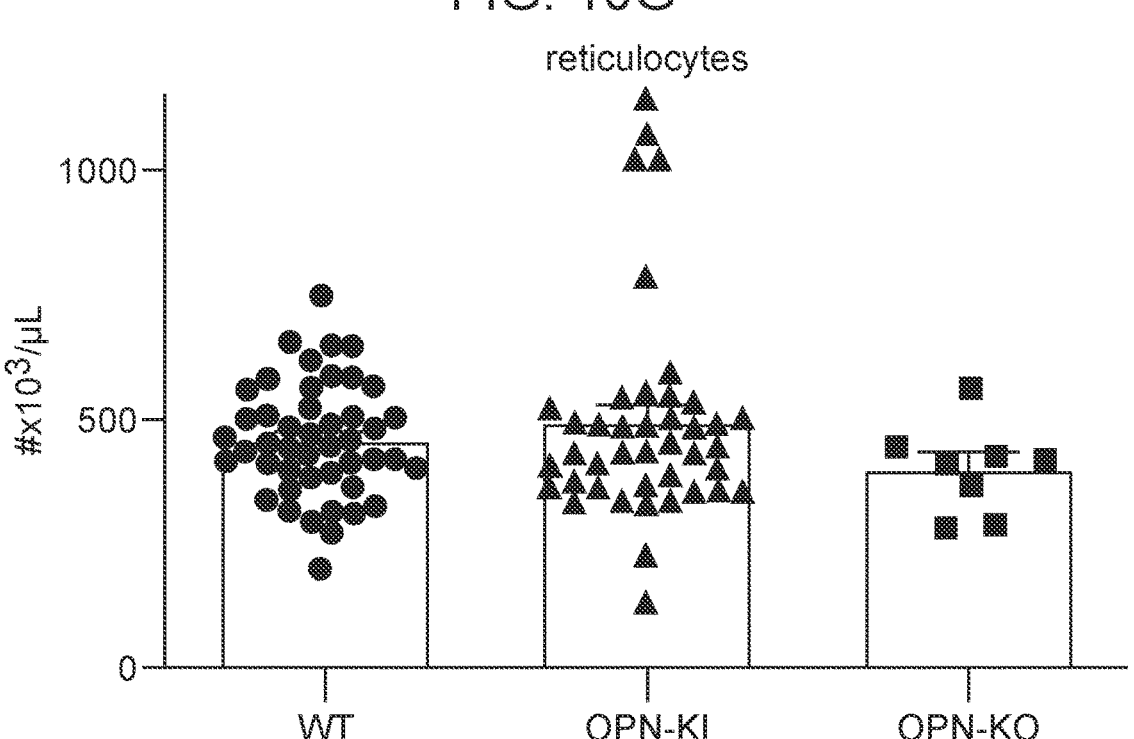
Figure 10G:
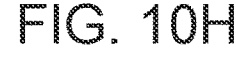
Figure 10H:
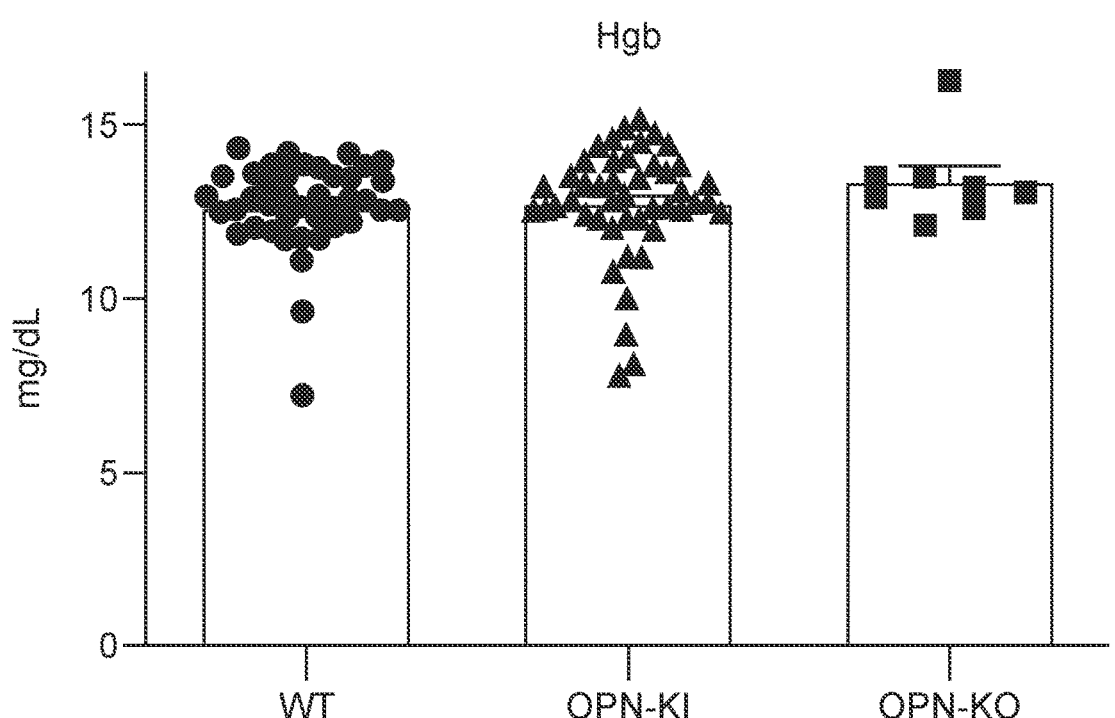
Figure 11A:
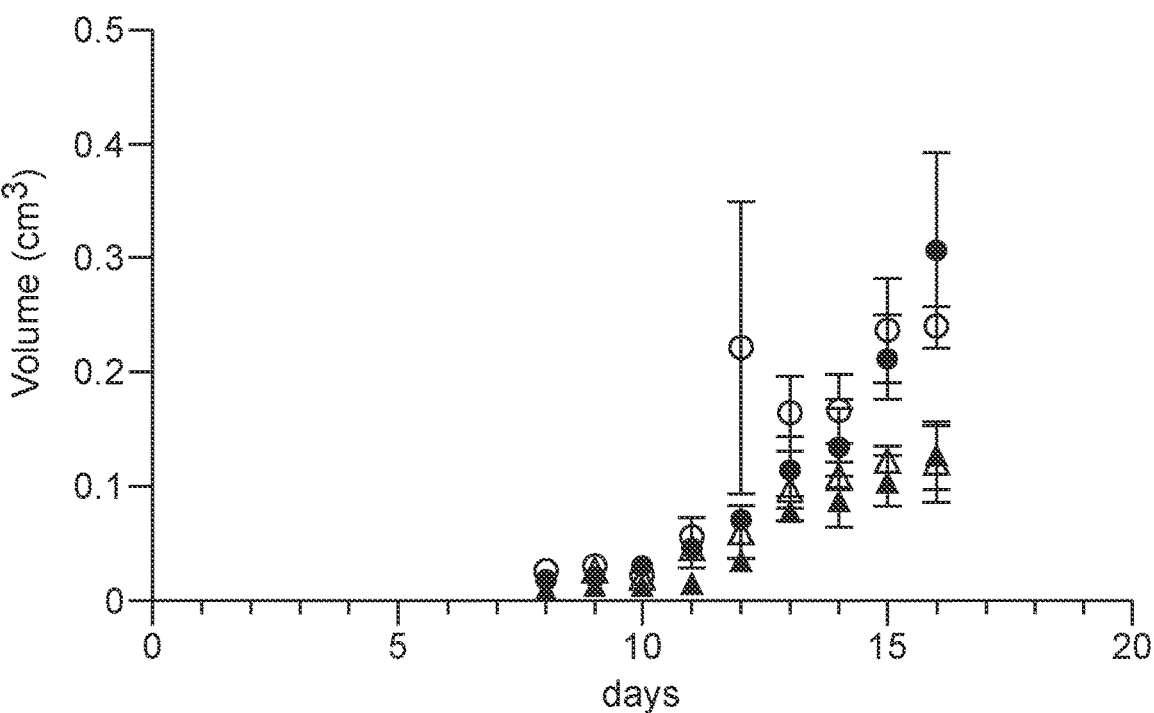
FIGS. 11A-11D: Comparison of B16 growth in male (solid symbols) and female (open symbols) WT (blue circles) and OPN-KI (green triangles) mice inoculated with different numbers of cells.
Figure 11B:
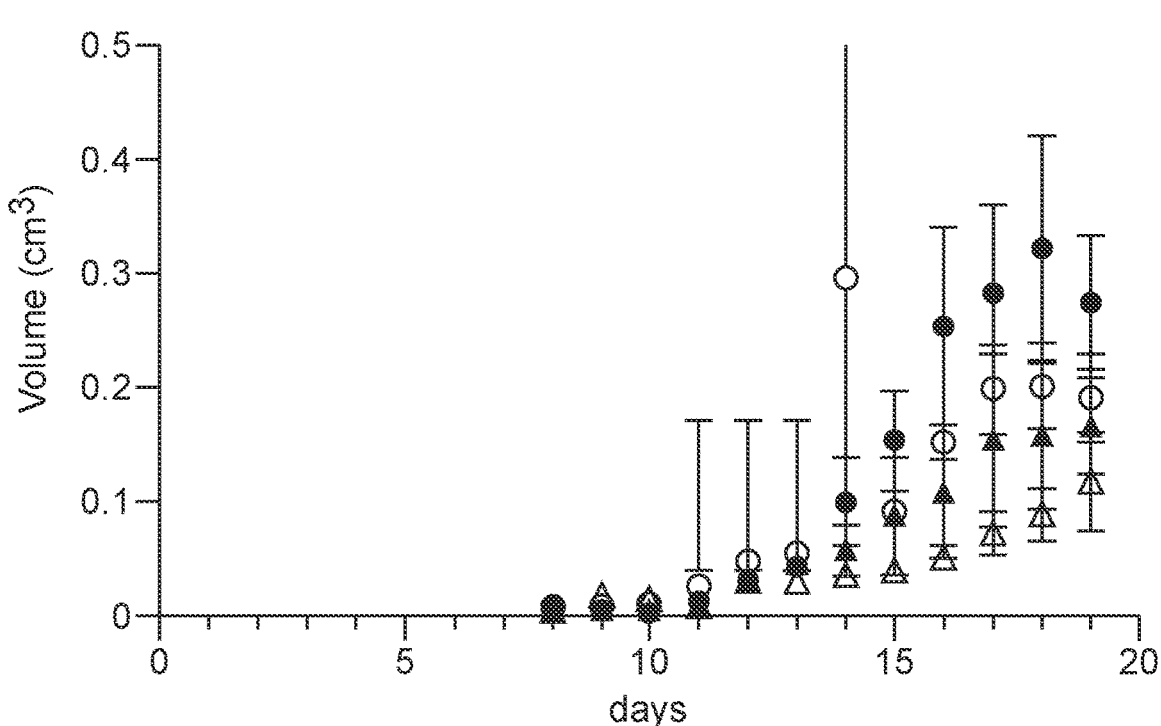
Figure 11C:
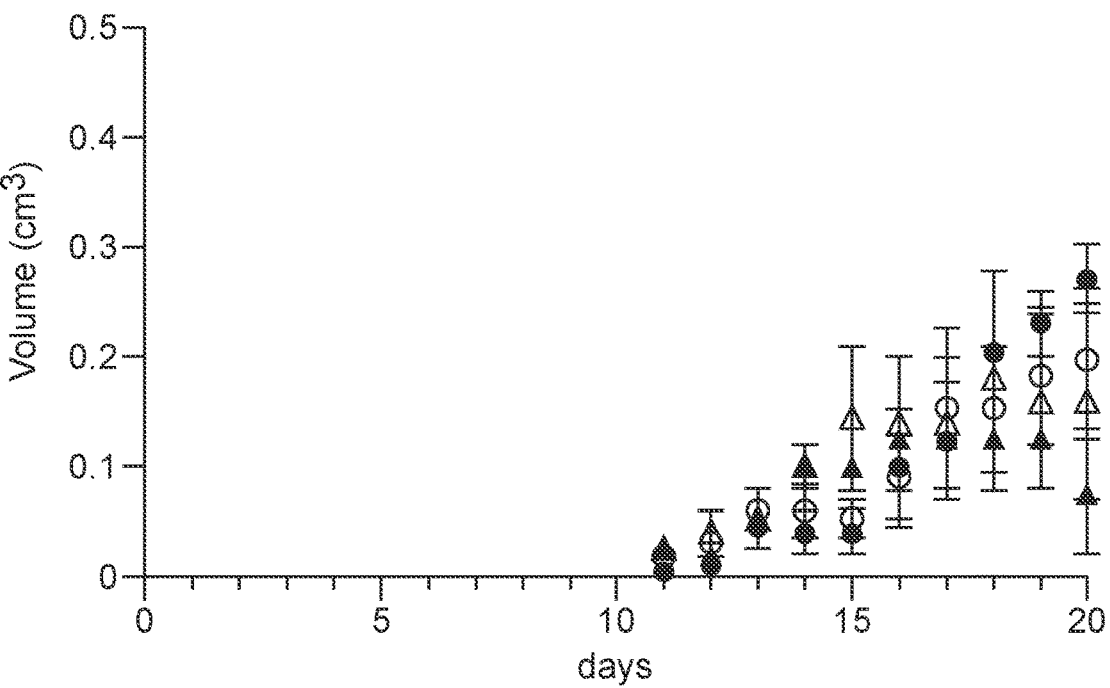
Figure 11D:
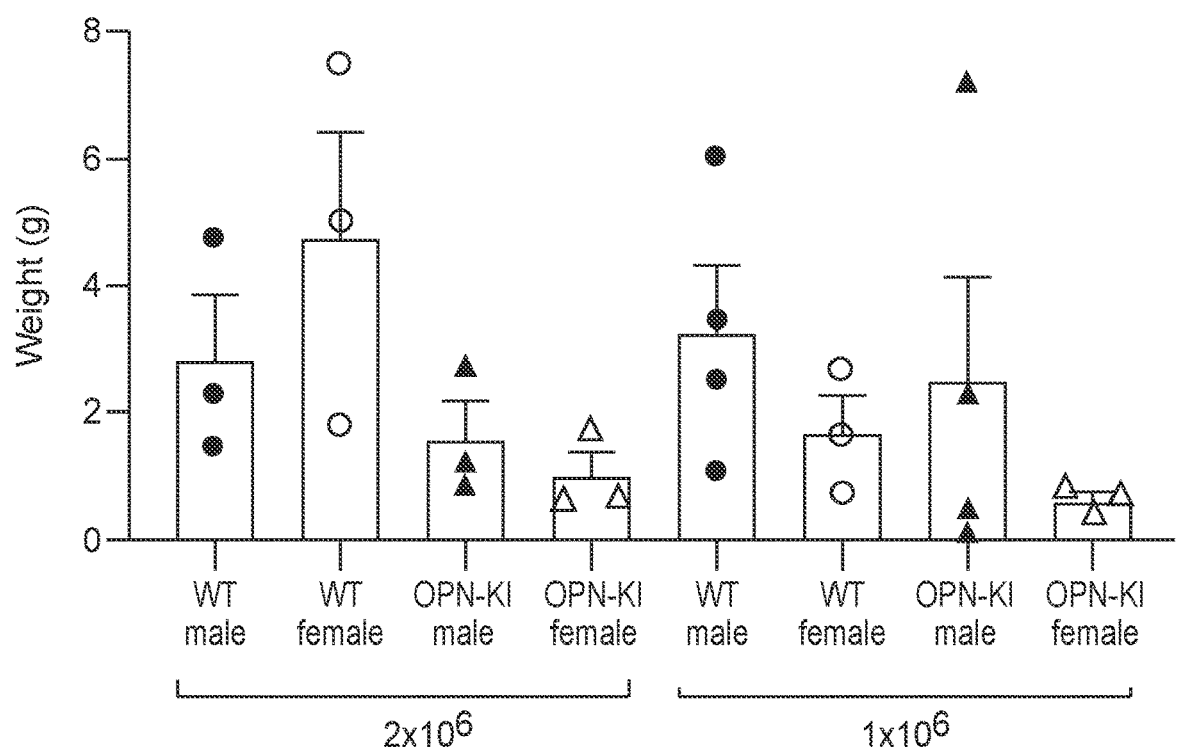

Changes in Macrophage Phenotypes in Tumor-Associated Macrophages (TAMs) from OPN-KI and OPN-KO Mice Compared to WT Mice We analyzed infiltrating macrophages and lymphocytes in the tumors from the different genotypes. In tumors from OPN-KI and OPN-KO mice compared to WT mice, overall tumor-associated macrophages (TAMs) (CD45+F4/80+) were increased (WT: 50.7±1.6% of CD45+; OPN-KI: 66.5±5.9%, p=0.0168 and OPN-KO: 58.3±1.1%, p<0.05 n=5 per group, FIG. 8A). There were no differences in numbers of M1 macrophages defined as EGR2-CD38+ macrophages (FIG. 8B). The fraction of M2 macrophages in the TAMs defined as either EGR2+CD38− or CD206+ CD11b+ macrophages was decreased (FIGS. 8C-8D), while the fraction of TAMs defined as CD11b+CD11c-CD206+ Ly-6G− macrophages was increased (WT: 4.7±0.65%, OPN-KI: 9.2±1.5%, p=0.0399 and OPN-KO: 9.0±1.3%, p=0.0495, n=5 per group, FIG. 8E). Therefore, in addition to an increase in the total number of TAMs in B16 tumors in OPN-KI and OPN-KO mice, there has been a switch from M2 macrophages to TAMs with a different activation profile in these tumors. There were no differences in numbers of infiltrating neutrophils, B- and T-cells in tumors from OPN-KI and OPN-KO mice compared to WT (FIGS. 8F-8H).

RAW Cell Responses to Different OPN Forms

Figure 15:
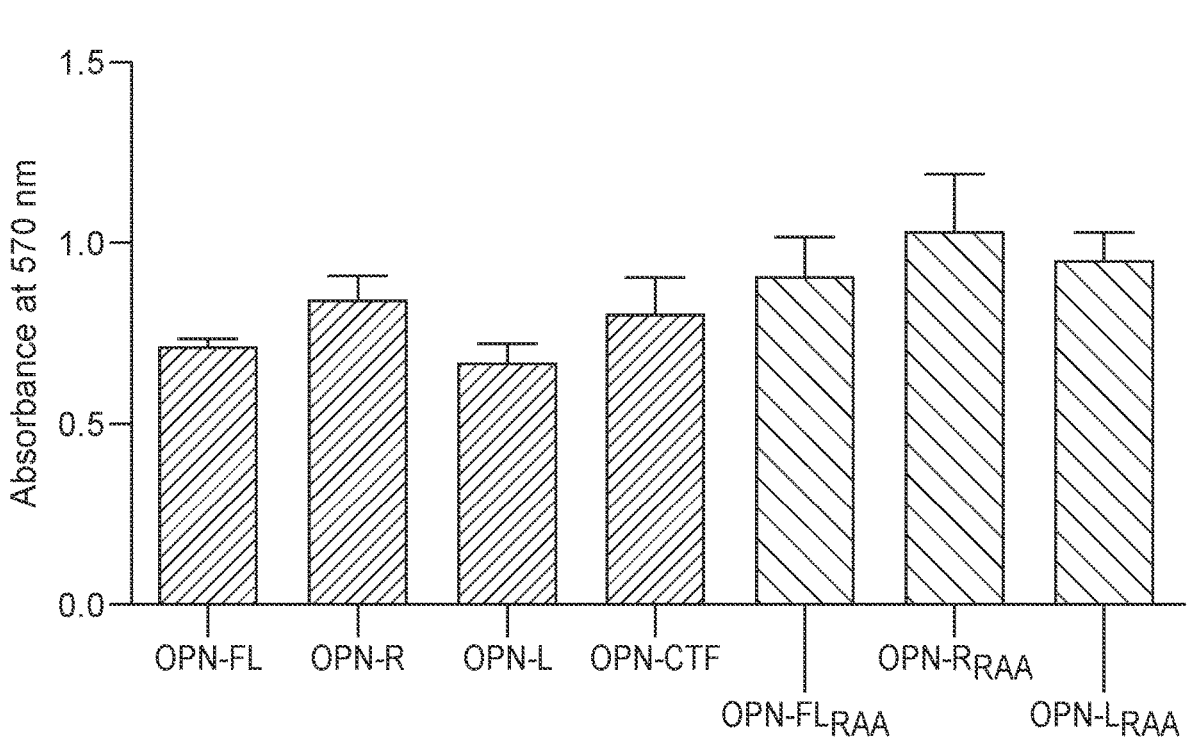
FIG. 15: Adhesion of RAW cells to different fragments of OPN.

RAW cells, a murine macrophage line, have been used as a model for TAMs (Kale et al., 2014, 2015) and we demonstrated that they expressed α9β1 and α4β1 integrins by flow cytometry (FIG. 12). We tested their responses to different fragments of OPN. All OPN fragments increased RAW cell adhesion compared to BSA with no differences between them (FIG. 15). We investigated prostaglandin E$_2$ (PGE$_2$) production as it is a mediator that has been reported to induce tumor angiogenesis and enhance B16 cell growth (Kale et al., 2014, 2015; Kawahara et al., 2015). OPN-R and OPN-R$_{RAA}$ both increased PGE$_2$ secretion in RAW cells by ~4.2 fold compared to OPN-FL (FIG. 8G), indicating that the increase in PGE$_2$ secretion was mediated by the α9β1 and α4β1 integrin-binding site revealed in OPN-R upon thrombin cleavage.

Discussion

In this study, we showed that thrombin cleavage of OPN plays a key pathophysiological role in cancer biology. There was extensive cleavage of OPN within the B16 tumors in WT mice, with levels of the thrombin-cleaved (OPN-R) and thrombin-CPN/CPB2 double-cleaved (OPN-L) OPN fragments accounting for >80% of the total OPN in the tumor samples, and these cleaved fragments became detectable in the plasma of tumor-bearing mice (FIG. 4). The thrombin cleavage-resistant OPN-KI mouse showed marked suppression of both B16 tumor growth and pulmonary metastasis, to a similar extent to that observed in the OPN-KO mouse (FIGS. 1 and 2). Thus, OPN-KI phenocopies OPN-KO in this tumor model, indicating that prevention of thrombin cleavage of OPN alone mediates the observed phenotype, independent of all the other functional domains on OPN. This tumor suppression phenotype in the KI mouse is immune-mediated, since it was not replicated in the severely immune-compromised NOG-OPN-KI and NOG-OPN-KO mice (FIG. 6). It is associated with an increase in F4/80$^+$ TAMs in the tumors, and depletion of macrophages by clodronate treatment reversed the phenotype in the KI mouse, indicating that the tumor suppression phenotype is mediated by macrophages (FIG. 5). Macrophage activation has been broadly defined into two states—a proinflammatory M1 state involved in the responses of type 1 helper T (Th1) cells to pathogens and an "alternatively activated" M2 state involved in Th2-type responses including humoral immunity and wound healing (Gordon, 2003). Substantial clinical and experimental evidence support the notion that TAMs promote tumor initiation and progression (Qian and Pollard, 2010) and macrophages in tumor are biased from M1 to M2 (Mantovani and Sica, 2010). Higher numbers of M2 TAMs are associated with worse clinical prognosis (Komohara et al., 2016). Thus, the M2 phenotype, in comparison to the M1 phenotype, is generally regarded as tumor-promoting (Gordon and Martinez, 2010; Mills, 2012). On the other hand, it is now recognized that the binary M1/M2 activation states are insufficient to describe the much broader complexity of stimuli and responses by the macrophage (Natoli and Monticelli, 2014). Different stimuli lead to a large variety of activation programs (transcription modules) (Xue et al., 2014), and in response to cues in the tumor microenvironment, TAMs can undergo dynamic functional reprogramming (Netea-Maier et al., 2018). Our study showed that in addition to an increase in TAMs, there was a significant change in the macrophage activation phenotype, with a switch from the tumor-promoting M2 phenotype in WT to a phenotype defined by CD45+F4/80+CD11c in the OPN-KI and OPN-KO mice (FIG. 7). In a metastatic breast cancer mode, OPN deficiency leads to tumor suppression and is associated with a switching to a more immunosuppressive cellular subsets in myeloid-derived suppressor cells (Sangaletti et al., 2014). In a glioblastoma model, M2 macrophages were reduced in tumors from OPN-KO mice (Wei et al., 2019). However, there was no investigation of thrombin cleavage of OPN in these studies (Mantovani and Sica, 2010; Qian and Pollard, 2010).

Using RAW cells as a model for TAMs, OPN-R significantly enhanced the secretion of PGE$_2$ (FIG. 8G), which has been reported to enhance angiogenesis and B16 tumor growth (Kale et al., 2014, 2015). Inhibition of PGE$_2$ production in platelets by COX-1 inhibitors reduced B16 metastasis (Lucotti et al., 2019). This pathway is abolished in the OPN-KI mouse and may contribute to the observed tumor suppression. Collectively, our data showed that tumor suppression in the OPN-KI mouse is mediated by an enhanced host-anti-tumor immune response mediated by an increase in TAMs that have been functionally modulated, with a reduction of the tumor-promoting M2 macrophages and replaced by a macrophage population with an altered activation state (FIG. 8H). The mechanisms by which these TAMs are modulated, via OPN-R, OPN-L, and/or OPN-CTF either directly or indirectly, and the functional characteristics of the increased population of CD45$^+$F4/80$^+$ CD11c$^-$ macrophages in the OPN-KO and OPN-KI mice remain to be fully defined.

Cancer represents an inflammatory state and cancer cells express a variety of cancer procoagulants including tissue factor (Hisada and Mackman, 2019; Kirszberg et al., 2009) that activate the coagulation cascade and lead to thrombin generation. There is an extensive literature on the cross-talk between coagulation activation and cancer cell biology (Lima and Monteiro, 2013; Ruf et al., 2016; Wojtukiewicz et al., 2015). Hirudin, a parenteral direct thrombin inhibitor, prevented metastasis of B16 cells (Niers et al., 2009). Cochrane systematic reviews showed a survival benefit of parenteral heparin in cancer patients, particularly in patients with limited small cell lung cancers (Akl et al., 2008a; Akl et al., 2008b; Akl et al., 2008c), although whether anticoagulation has a direct beneficial effect on cancer patient survival remains controversial (O'Rorke et al., 2015). Our data support the notion that thrombin cleavage of OPN leads to suppression of the host-anti-tumor immune response, and cancer cells exploit this mechanism to enhance their survival. We showed that dabigatran, a direct orally active anticoagulant (DOAC), replicated the tumor suppression phenotype in both local tumor growth as well as metastasis in WT mice. It is interesting that rivaroxaban, a DOAC targeting factor Xa in the clotting cascade, has also been shown to promote antitumor immunity by blocking factor Xa-protease-activated receptor 2 signaling in TAMs (Graf et al., 2019). DOACs are now increasingly used clinically and have proven to have a superior therapeutic profile compared to warfarin, the conventional vitamin K antagonist (Hakoum et al., 2018; Kahale et al., 2018; Matar et al., 2018). As such, dabigatran and other DOACs might be considered as an adjunct to conventional chemotherapy in cancer treatment, if these observations are generalizable to other cancers. On the other hand, it is also well recognized that there is a higher incidence of bleeding complications in cancer patients upon anticoagulation, perhaps related to a more leaky tumor vasculature (Schuliga, 2015). Thus, the development of a drug that effectively blocks thrombin cleavage of OPN without compromising the integrity of the blood clotting cascade would represent a novel adjunctive therapy in cancer treatment.

In summary, this is the first direct demonstration of the role for thrombin cleavage of OPN in vivo. Our study shows that thrombin-cleaved OPN fragments have a significant pathophysiological impact on cancer biology and may offer a unique opportunity to develop novel therapeutic agents for cancer treatment by enhancing the host-anti-tumor immune response mediated by TAMs. Their clinical application may not be limited to cancer therapy since thrombin-cleaved OPN has been reported to induce collagen production in cardiac fibroblasts and may play a role in cardiac fibrosis (Herum et al., 2020).

Materials and Methods

| Key Resources Table | | |
| --- | --- | --- |
| Reagent or resource | Source | Identifier |
| Antibodies | | |
| Rabbit anti-mouse OPN-R | Laboratory of Dr. Leung | N/A |
| Rabbit anti-mouse OPN-L | Laboratory of Dr. Leung | N/A |

-continued

| Key Resources Table | | |
|---|---|---|
| Reagent or resource | Source | Identifier |
| PE goat anti-mouse Integrin α9 Antibody | R & D systems | Cat. #: FAB3827P |
| PE rat anti-mouse Integrin β1 (CD29) Antibody | R & D systems | Cat. #: FAB2405P-100 |
| PE anti-mouse CD49d (Integrin α4) Antibody | Affymatrix eBiosciences | Cat. #: 12-0492-82 |
| PE goat IgG isotype control Antibody | R & D systems | Cat. #: IC108P |
| PE rat IgG2a Isotype Control Antibody | Tonbo biosciences | 50-4321-U100 |
| PE rat IgG2b isotype control Antibody | Tonbo biosciences | 50-4031-U100 |
| Brilliant Violet 421 ™ anti-mouse CD45 Antibody | BioLegend | Cat. #: 103133 |
| PE anti-mouse CD206 (MMR) Antibody | BioLegend | Cat. #: 141706 |
| Brilliant Violet 510 ™ anti-mouse I-A/I-E Antibody | BioLegend | Cat. #: 107635 |
| PE/Cy7 anti-mouse CD11c Antibody | BioLegend | Cat. #: 117318 |
| APC/Cy7 anti-mouse/human CD11b Antibody | BioLegend | Cat. #: 101226 |
| Brilliant Violet 785 ™ anti-mouse F4/80 Antibody | BioLegend | Cat. #: 123141 |
| PerCP/Cyanine5.5 anti-mouse CD38 Antibody | BioLegend | Cat. #: 102722 |
| Brilliant Violet 650 ™ anti-mouse Ly-6G/Ly-6C (Gr-1) Antibody | BioLegend | Cat. #: 108441 |
| EGR2 Monoclonal Antibody (erongr2), APC | Invitrogen | Cat. #: 17-6691-82 |
| Sytox ™ Green | BioLegend | Cat. #: 425303 |
| Fc blocking antiCD16/32 | Tonbo | Cat. #: 70-0161-U100 |
| Cell line | | |
| Murine B16F10 melanoma | ATCC | Cat. #: CRL6475, RRID:CVCL__0159 |
| Murine RAW 264.7 | ATCC | Cat. #: TIB-71 |
| Chemicals | | |
| ACK lysis buffer | Lonza | Cat. #: 10-548E |
| Clodronate | Clodrosome | CLD-8901 |
| Control liposomes | Clodrosome | CLD-8901 |
| complete protease inhibitor cocktail | Roche | 4693116001 |
| Dabigagtran Etexilate | Boehringer Ingelheim | |
| Tumor Dissociation Kit | Miltenyi Biotec | Cat. #130-096-730 |
| Red Blood Cell Lysis Solution | BioLegend | Cat. # 420301 |
| UntraComp eBeads Compensation Beads | Invitrogen | Cat. # 01-2222-42 |
| Commercial Assays | | |
| ELISA for mouse osteopontin | R&D Systems | Cat. #: DY441 |
| Protein assay | Biorad | 5000006 |
| Mouse chow | | |
| Chow with dabigatran etexilate | Dyets | |
| Control chow for dabigatran etexilate chow | Dyets | |
| Standard chow | | |
| Mouse strains | | |
| WT | Jackson Labs | |
| OPN-KO | Jackson Labs | |
| OPN-KI | Caliper Discovery Alliances and Services | |
| NOG-WT | CIEA | |
| NOG-WT-OPN-KI | CIEA | |
| NOG-WT-OPN-KO | CIEA | |
| Oligonucleotides | | |
| NeoPCRF1: GGTTTCCAAATGTGTCAGTTTCATAGCC (SEQ ID NO: 1) | Caliper | |
| StanfordU2 3R: TCTGAAACATAGTTCCCTAAGACATCAG (SEQ ID NO: 2) | Caliper | |
| StanfordU2 5cko: ATCATCAATGCTTAGCCAAGCCAAG (SEQ ID NO: 3) | Caliper | |

-continued

| Key Resources Table | | |
| --- | --- | --- |
| Reagent or resource | Source | Identifier |
| Recombinant DNA | | |
| Plasmid: LoxNwCD Software | Caliper | |
| Adobe Photoshop CS5 Extended (version 12.0 3 32) | Adobe | adobe.com/ |
| Graphpad Prism v8.3 | Graphpad Software | graphpad.com/ |
| Microsoft Office Standard 2010 | Microsoft Corporation | products.office.com/ |
| FlowJo ™ v10.6.2 | BD (Becton, Dickinson & Company) | flowjo.com/ |

Generation of Mice Expressing Thrombin-Resistant Osteo-pontin (Spp1$^{R153A/R153A}$)

Figure 16:
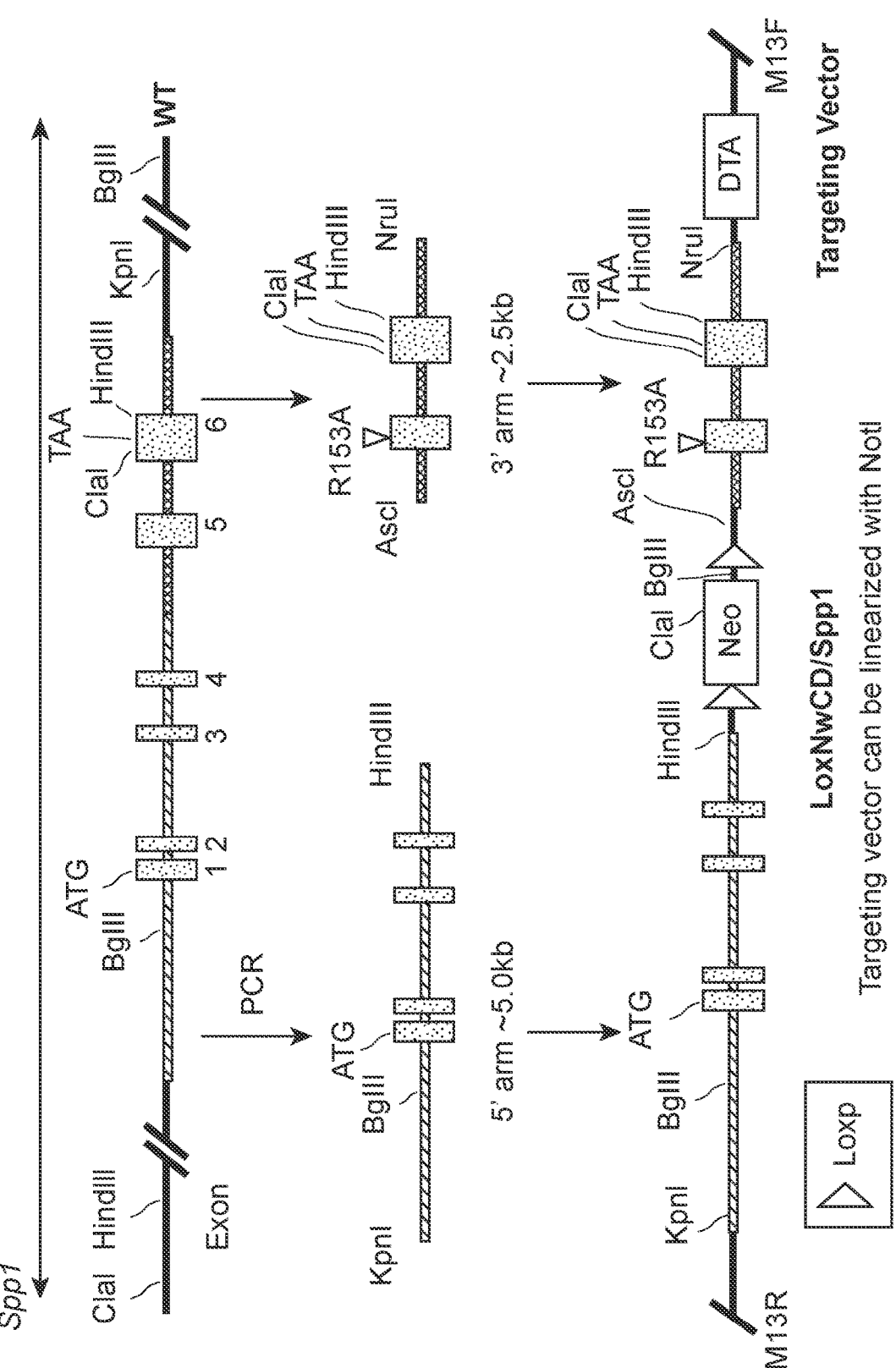
FIG. 16: The construction of the targeting vector is shown. The Spp1 gene sequence (nucleotides 104,834,137-104,900,066) from mouse chromosome 5 is shown in the WT line (top line). Two plasmids, one with the 5' homology arm (exons 1-4) and the 3' homology arm (exons 5 and 6) were constructed. Exon5 containing the codon for amino acid 153 which was mutated from Arg to Ala (R153A; red arrow). These two sequences were then inserted into the targeting vector LoxNwCD along with the Neo cassette flanked by LoxP sites (bottom line, targeting vector). ATG: initiation codon; DTA: diphtheria toxin.

To create a R153A knock-in point mutation in the gene encoding osteopontin (OPN; secreted phosphoprotein 1, Spp1) that prevents thrombin cleavage of OPN in mice, we used homologous recombination in mouse embryonic stem (ES) cells and subsequent blastocyst injection of the appropriate targeted ES cells (FIG. 16). The Spp1 gene sequence (nucleotides 104,834,137~104,900,066) located on mouse chromosome 5 was retrieved from the Ensembl database and used as reference. Mouse RP23-410M1 BAC DNA was used for generating the homology arms for the gene targeting vector, and Southern probes for screening the targeted events. The 5' homology arm (~5.0 kb) and the 3' homology arm (~2.5 kb) were both generated by PCR. The R153A point mutation, located in exon 5 of the 3' homology arm, was introduced by site-directed mutagenesis. These fragments were cloned into the LoxNwCD vector sequentially and were confirmed by restriction digestion and end-sequencing.

The final vector also contained loxP sequences flanking the Neo expression cassette (for positive selection of the ES cells), and a diphtheria toxin A (DTA) expression cassette (for negative selection of the potentially targeted ES cells). The final vector was confirmed by both restriction endonuclease digestion and by end sequencing analysis. NotI was used for linearizing the final vector prior to electroporation.

5' and 3' external probes were generated by PCR and tested by genomic Southern analysis for screening the ES cells. The probes were cloned in the pCR4.0 backbone and confirmed by sequencing.

NotI-linearized final vector DNA (30 μg) was electroporated into ~10$^7$ C57BL/6J ES cells and selected with 200 μg/ml G418. 192 ES cell clones were selected for PCR-based screening and five potential targeted clones were selected for expansion and further analysis. Upon completion of the embryonic ES clone expansion, additional Southern and PCR/sequencing confirmation analysis was performed and showed that two clones (E9 and F8) were correctly targeted and have a single neo insertion.

Figure 17A:
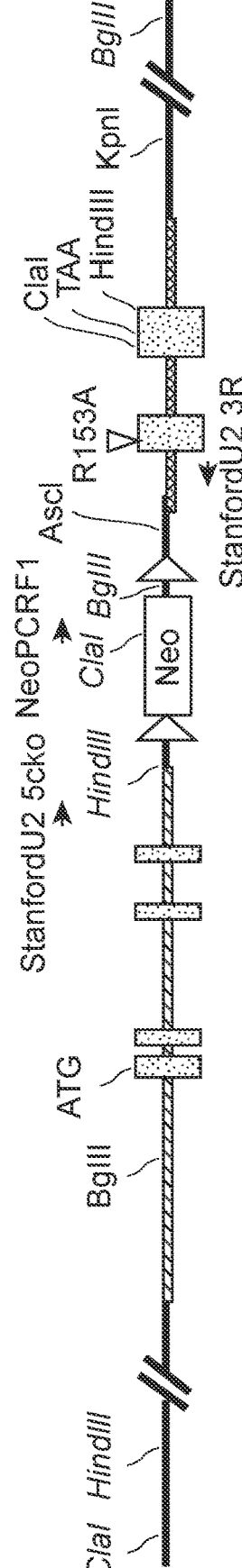
FIGS. 17A-17B.
Figure 17B:
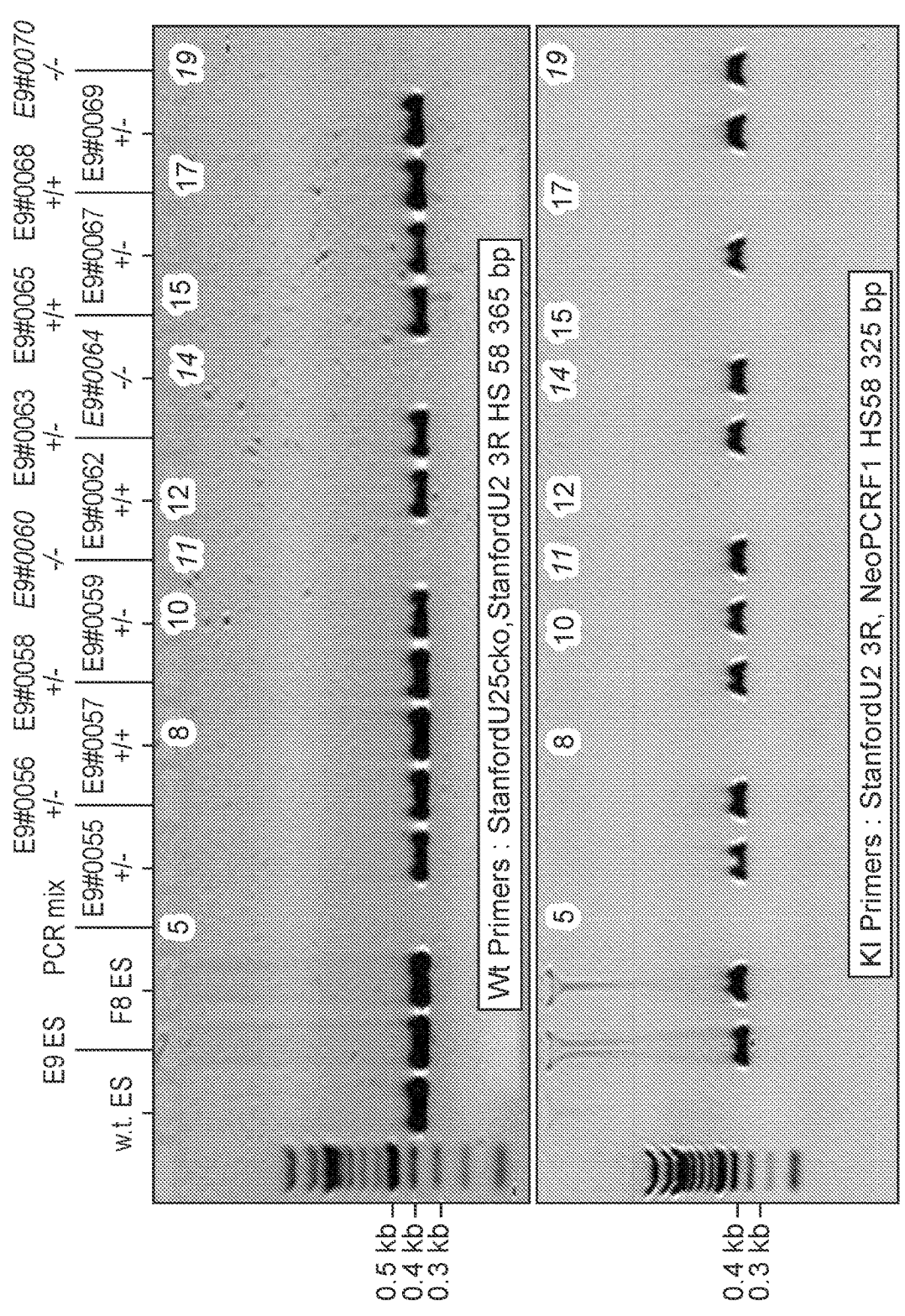

Blastocyst injection was performed with clones E9 and F8 and male chimeras were generated: 99% (n=1), 90% (n=1), 80% (n=2), 70% (n=2), 60% (n=1), 50% (n=1), 40% (n=1), 30% (n=1), and 20% (n=1). These male chimeras were bred with C57BL/6J WT females to generate heterozygotes that were identified by PCR analysis. Subsequent back-crosses with C57BL/6J mice generated homozygous mice carrying the mutant Spp1 gene, again identified by PCR analysis (FIGS. 17A and 17B) using primers described in Table 1. Targeting and ES cell work was performed by Caliper Discovery Alliances and Services (Hanover, MD).

From here on, homozygous C57BL/6J Spp1$^{R153A/R153A}$ mice are designated as "OPN-KI" mice while Spp1$^{-/-}$ mice obtained from Jackson Laboratories (Sacramento, CA) as "OPN-KO" mice. The mice were either housed at Stanford University School of Medicine or at Veterans Affairs Palo Alto Health Care System (VAPAHCS) and experiments were performed under protocols approved by the Stanford University Committee of Animal Research or the VAPAHCS Institutional Animal Care and Use Committee in accordance with NIH guidelines. Animals were randomized to the different groups and analysis was blinded. All experiments were repeated at least twice independently and all mice that entered the experiments were accounted for.

Immune-deficient mice carrying OPN-KI and OPN-KO genes: NOG-WT, NOG-OPN-KO and NOG-OPN-KI mice (Ito et al., 2002) were obtained from the Central Institute for Experimental Animals (CIEA; Kawasaki, Japan) and housed in a gnotobiotic facility at the VAPAHCS. These mice possess an intact OPN gene (NOG-WT), are deficient in OPN (NOG-OPN-KO) or carry the R153A mutation in the OPN gene rendering OPN thrombin-resistant (NOG-OPN-KI).

Plasma samples were prepared from mice with or without tumor implantation by collection of blood via cardiac puncture into 3.2% sodium citrate with 9:1 blood to citrate ratio. Tumor lysates were prepared by homogenizing the tumor samples from all the genotypes in RIPA buffer (Pierce, Carlsbad, CA) with complete protease inhibitor cocktail (Roche). Protein concentration was determined by Bio-Rad Protein Assay (Bio-Rad, Hercules, CA). Bone marrow cells were prepared as described previously (Toda et al., 2013).

Clinical chemistry: Clinical chemistry analysis was carried out on plasma from 12-week old male and female WT, OPN-KI and OPN-KO mice. Liver function was investigated by measuring the levels of alanine transaminase (ALT) and aspartate transaminase (AST), and kidney function by determining blood urea nitrogen (BUN) and creatinine levels. No differences were found between genotypes in these measurements (FIG. 9). Lactate dehydrogenase (LDH), bilirubin, cholesterol were determined in these samples and also showed no differences between genotypes.

Circulating blood cells: Complete blood counts (CBC) were carried out on male and female WT, OPN-KI and OPN-KO mice at different ages from 5 weeks to 26 weeks. No differences were found between genotypes in any of the cell types investigated including erythrocytes, neutrophils, lymphocytes, monocytes, basophils, eosinophils, platelets and reticulocytes. FIG. 10 shows CBC data taken from 12-week old mice. There was no difference between males and females of the different genotypes, and samples taken at different ages also showed no differences between genotypes.

Cell culture: B16 (mouse melanoma) and RAW (mouse macrophage) cell lines were obtained from ATCC (Manassas, VA) and were cultured in DMEM (Corning, NY) in the presence of 5% fetal bovine serum (FBS) with penicillin-streptomycin-glutamine (Gibco Life Technologies, Langley, OK). To determine Spp1 mRNA, confluent B16 cells were trypsinized, RNA isolated and RT-PCR performed, with a plasmid containing the Spp1 gene used as the positive control.

Proteins and reagents: The different recombinant fragments of OPN including mutated forms were produced as previously described (Shao et al., 2014; Yamaguchi et al., 2013). BSA was from Invitrogen (Carlsbad, CA).

B16 subcutaneous tumor inoculation: B16 cells were grown until confluent and $2\times10^6$ cells were inoculated subcutaneously into WT, OPN-KI and OPN-KO mice. Mice were monitored daily for tumor growth. Tumor size was measured and volume calculated using the equation (width× width×length)/2. Animals were euthanized using $CO_2$ and blood collected by cardiac puncture and tumors were isolated carefully. Blood was centrifuged at 2500 rpm for 20 min to prepare plasma and stored at –80° C. Tumors were weighed and measured. Part of the tumor was stored in formaldehyde for immunohistochemistry, part of it was frozen and stored at –80° C. for preparation of tumor lysates for OPN ELISAs.

Dabigatran Etexilate (DE) treatment: DE (Boehringer Ingelheim, Ridgefield, CT) was administered to WT and OPN-KI mice orally. DE was incorporated at a concentration of 28.61 g DE/kg into chow (Dyets Inc, Bethlehem, PA) following the protocol described previously (Sparkenbaugh et al., 2014). Briefly, mice were fed 4 days before inoculation of $2\times10^6$ B16 cells subcutaneously on either DE-containing chow or matched control chow. Animals were monitored daily and sacrificed after 2 weeks. Tumor weights and volumes were measured and calculated as described above. Blood was collected in 3.8% sodium citrate before plasma preparation and activated partial thromboplastin time (aPTT) determined.

Depletion of phagocytes by clodronate: Phagocytes were depleted from WT, OPN-KI and OPN-KO mice by injecting 150 μl clodronate (5 mg/ml) or control liposomes retro-orbitally (Clodrosome, Brentwood, TN) every second day (Winkler et al., 2010). After 2 doses of clodronate, $2\times10^6$ B16 cells were inoculated subcutaneously. Subsequently, mice were given clodronate or control liposomes on alternate days for 2 weeks until sacrifice and their tumors were processed as described above.

Histology and Immunohistochemistry:

B16 metastasis model: $0.5\times10^6$ B16 cells were injected via tail vein into mice. After sacrifice, the lung was isolated and the number of metastatic nodules on surface was counted on both sides, before analyzing the left lobe for melanin determination. The left lobe of lung from each mouse was incubated in 1N NaOH/10% DMSO for 2 hr at 80° C. before centrifugation at 12,000 rpm for 10 min at room temperature. The absorbance at 470 nm of the supernatant was measured and compared to a standard of synthetic melanin (Sigma, St. Louis, MO). Lung was weighed before the start of process and melanin content was expressed as μg/mg protein determined by protein assay of lung tissue.

OPN ELISAs: ELISAs for detection of total OPN, OPN-R and OPN-L have been described previously (Sharif et al., 2009).

Cell adhesion assay: Wells in 96-well plate was coated with either BSA or different OPN fragments at a concentration of 20 nM in coating buffer (Gibco Life Technologies, Langley, OK) and incubated at 4° C. overnight. The plate was then washed thrice with PBS before blocking with 3% BSA for 1 hr. The cells were washed thrice with 1×HBSS containing 0.2 mM $MnCl_2$. $2\times10^6$ B16 or RAW cells were added to the wells and incubated at 37° C. for 1 hr. Wells were washed and cells fixed with absolute ethanol for 20 min before staining with 0.1% crystal violet. Cells were washed repeatedly with PBS until no violet color was visible, lysed with 0.5% Triton X-100 and absorbance determined at 570 nm.

Cell growth assay: $5\times10^4$ B16 cells were plated in 12-well plate in DMEM without serum and allowed to settle for 1 hr. Then OPN fragments or BSA (10 nM) were added to the medium. After 24 hr at 37° C., cells were trypsinized, counted and the growth ratio was calculated by normalizing to the cell count for BSA.

Apoptosis assay: $1\times10^5$ B16 cells were cultured in DMEM without serum overnight before addition of 20 μM camptothecin (Abcam, Burlingame, CA) in the presence of BSA or OPN fragments (10 nM). Cells were then incubated for 4 hr before addition of 200 μl of binding buffer. The plate was centrifuged at 400 g for 5 min and supernatant discarded. Annexin V FITC stain (Cayman chemicals, Ann Arbor, MI) was added to the cells and incubated at RT for 10 min in the dark. Cells were centrifuged as described above and 100 μl of binding buffer was added to each cell and fluorescence intensity measured at 485/535 nm (excitation/emission). Apoptotic index was calculated by dividing the camptothecin-treated cells with untreated cells.

Cell migration assay: $10^5$ B16 cells were placed in the upper chamber of a 6.5 mm transwell with a pore size of 8.0 μm (Sigma, XX). Cells were allowed to settle before the lower chamber was filled with BSA or various OPN fragments (10 nM) in presence of 0.2 mM $MnCl_2$ (Sigma, St Louis, MO) and incubated at 37° C. for 24 hr. Cells that migrated to the lower chamber were centrifuged and resuspended into 90 ul of 1×HBSS (Gibco Life Technologies, Langley, OK) with 10 μl of CCK-8 staining solution (Dojindo Molecular Technologies Inc., Rockville, MD). Cells were incubated for 2 hr before measuring absorbance at 450 nm.

$PGE_2$ assay: $5\times10^5$ RAW cells were plated onto 6-well plate in serum free medium with either BSA or various OPN fragments (10 nM). Cells were cultured overnight before collecting the media and determining $PGE_2$ by ELISA (Enzo, Farmingdale, NY).

Flow cytometric analysis of leukocytes: Tumors were isolated, weighed and similar weights were used for processing. Tumors were dissociated with Tumor Dissociation Kit (Miltenyi Biotec) and gentleMACS Octo Dissociator with Heaters (Miltenyi Biotec) according to the manufacturer's instructions. After dissociation, the cell suspension was filtered with a 40 mm filter before cells were subjected to erythrocyte cell lysis using ACK lysis buffer (Lonza, Walkersville, MD). Lysis buffer was inactivated by adding 10 times vol/vol of DMEM medium containing serum. Cells were centrifuged (300 rcf, 10 min) and gently resuspended in FACS buffer (PBS+1% BSA) and counted. After blocking

35

Figure 18A:
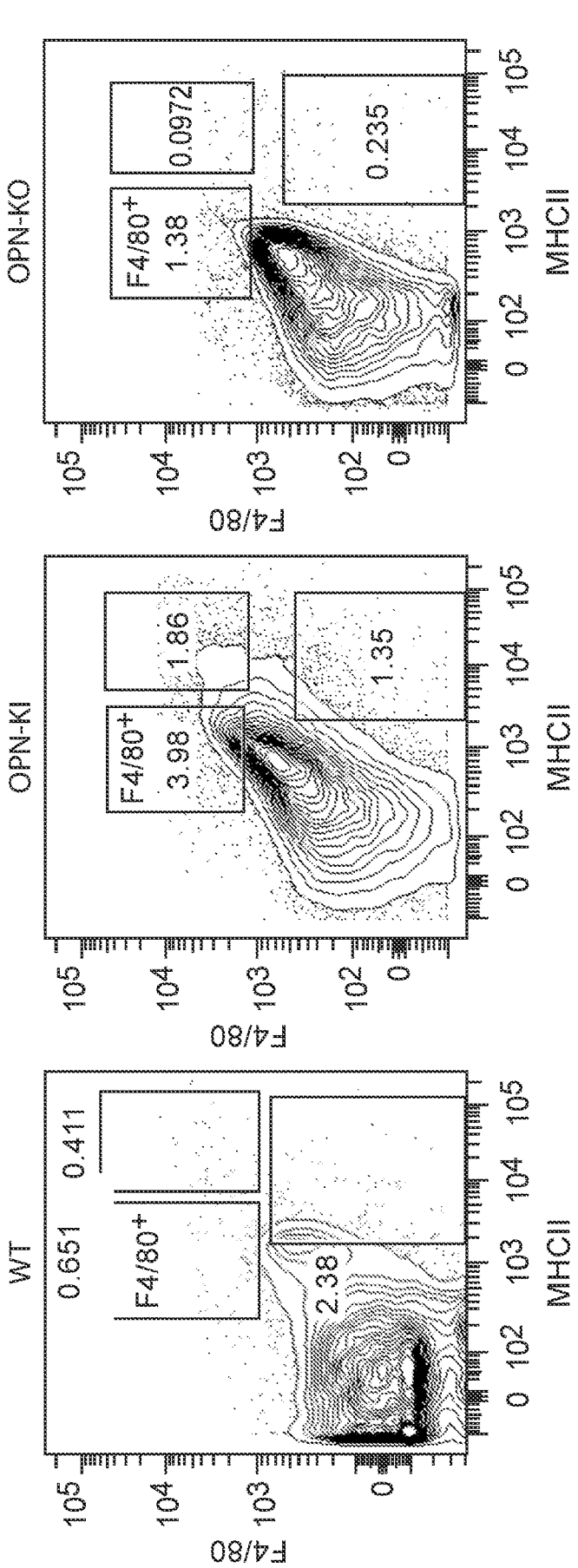
FIGS. 18A-18C: Gating strategy employed for analysis of F4/80+ cells (FIG. 18A), for tumor-infiltrating macrophages (FIG. 18B) and B and T cells (FIG. 18C).
Figure 18B:
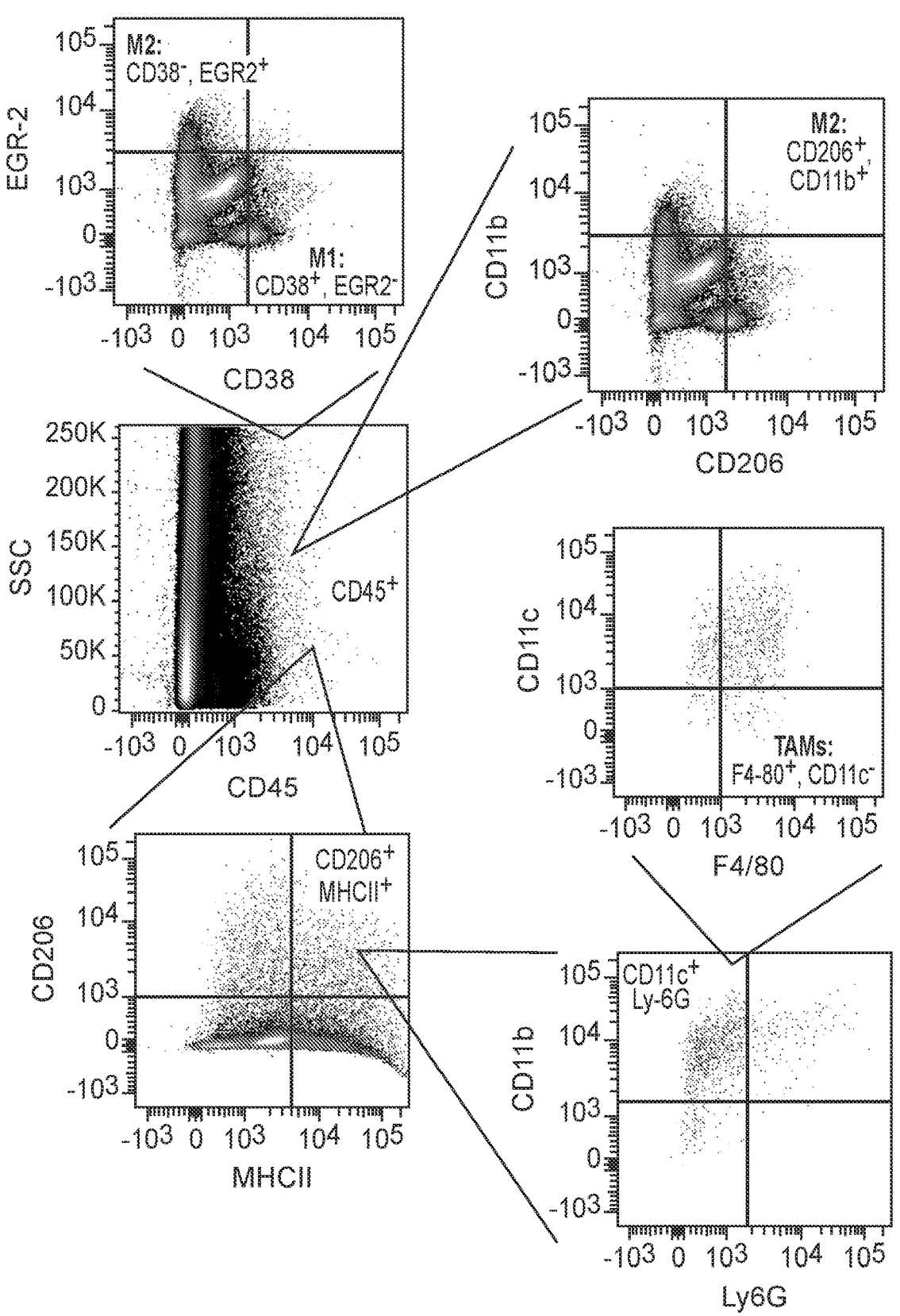
Figure 18C:
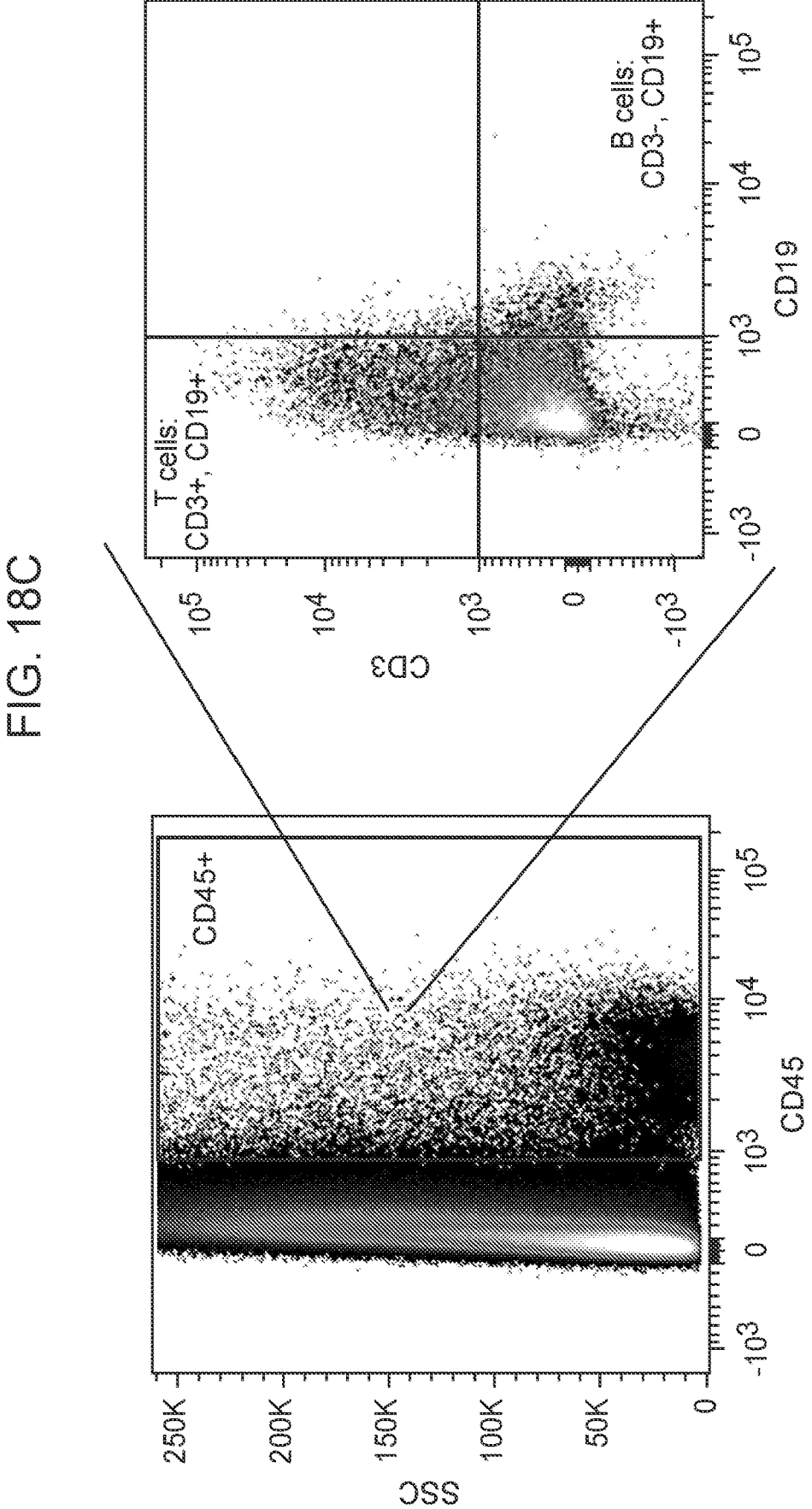

Fc with CD16/32 Fc blocking antibody for 20 min, $10^6$ cells were stained for 30 min at 4° C. in the dark with either a mixture of antibodies against CD45, CD206, CD11c, CD38, Gr-1, EGR-2, CD3, CD19, CD11b, F4/80, MHC II and Cytox green (Jablonski et al., 2015; Weichand et al., 2017), or a mixture of antibodies against CD45, CD3, CD19, and Cytox green. Cells were then washed again with FACS buffer. Compensation Beads (Invitrogen, XX) and samples stained with single antibody were used for controls. The cells were analyzed on a flow cytometer (BD LSR 1l) and data analysis was carried out with FlowJo (BD). The gating strategy is shown in FIG. 18.

REFERENCES

Akl, E. A., Barba, M., Rohilla, S., Terrenato, I., Sperati, F., Muti, P., and Schunemann, H. J. (2008a). Anticoagulation for the long term treatment of venous thromboembolism in patients with cancer. The Cochrane database of systematic reviews, CD006650.

Akl, E. A., Rohilla, S., Barba, M., Sperati, F., Terrenato, I., Muti, P., and Schunemann, H. J. (2008b). Anticoagulation for the initial treatment of venous thromboembolism in patients with cancer. The Cochrane database of systematic reviews, CD006649.

Akl, E. A., van Doormaal, F. F., Barba, M., Kamath, G., Kim, S. Y., Kuipers, S., Middeldorp, S., Yosuico, V., Dickinson, H. O., and Schunemann, H. J. (2008c). Parenteral anticoagulation may prolong the survival of patients with limited small cell lung cancer: a Cochrane systematic review. J Exp Clin Cancer Res 27, 4.

Atai, N. A., Bansal, M., Lo, C., Bosman, J., Tigchelaar, W., Bosch, K. S., Jonker, A., De Witt Hamer, P. C., Troost, D., McCulloch, C. A., et al. (2011). Osteopontin is up-regulated and associated with neutrophil and macrophage infiltration in glioblastoma. Immunology 132, 39-48.

Cardones, A. R., Murakami, T., and Hwang, S. T. (2003). CXCR4 enhances adhesion of B16 tumor cells to endothelial cells in vitro and in vivo via beta(1) integrin. Cancer research 63, 6751-6757.

Chiodoni, C., Colombo, M. P., and Sangaletti, S. (2010). Matricellular proteins: from homeostasis to inflammation, cancer, and metastasis. Cancer Metastasis Rev 29, 295-307.

Clemente, N., Raineri, D., Cappellano, G., Boggio, E., Favero, F., Soluri, M. F., Dianzani, C., Comi, C., Dianzani, U., and Chiocchetti, A. (2016). Osteopontin Bridging Innate and Adaptive Immunity in Autoimmune Diseases. Journal of immunology research 2016, 7675437.

Conway, C., Mitra, A., Jewell, R., Randerson-Moor, J., Lobo, S., Nsengimana, J., Edward, S., Sanders, D. S., Cook, M., Powell, B., et al. (2009). Gene expression profiling of paraffin-embedded primary melanoma using the DASL assay identifies increased osteopontin expression as predictive of reduced relapse-free survival. Clinical cancer research: an official journal of the American Association for Cancer Research 15, 6939-6946.

Coppola, D., Szabo, M., Boulware, D., Muraca, P., Alsarraj, M., Chambers, A. F., and Yeatman, T. J. (2004). Correlation of osteopontin protein expression and pathological stage across a wide variety of tumor histologies. Clinical cancer research: an official journal of the American Association for Cancer Research 10, 184-190.

Gordon, S. (2003). Alternative activation of macrophages. Nature reviews Immunology 3, 23-35.

Gordon, S., and Martinez, F. O. (2010). Alternative activation of macrophages: mechanism and functions. Immunity 32, 593-604.

Graf, C., Wilgenbus, P., Pagel, S., Pott, J., Marini, F., Reyda, S., Kitano, M., Macher-Goppinger, S., Weiler, H., and Ruf, W. (2019). Myeloid cell-synthesized coagulation factor X dampens antitumor immunity. Sci Immunol 4.

Grassinger, J., Haylock, D. N., Storan, M. J., Haines, G. O., Williams, B., Whitty, G. A., Vinson, A. R., Be, C. L., Li, S., Sorensen, E. S., et al. (2009). Thrombin-cleaved osteopontin regulates hemopoietic stem and progenitor cell functions through interactions with alpha9beta1 and alpha4beta1 integrins. Blood 114, 49-59.

Hakoum, M. B., Kahale, L. A., Tsolakian, I. G., Matar, C. F., Yosuico, V. E., Terrenato, I., Sperati, F., Barba, M., Schunemann, H., and Akl, E. A. (2018). Anticoagulation for the initial treatment of venous thromboembolism in people with cancer. The Cochrane database of systematic reviews 1, CD006649.

Hayashi, C., Rittling, S., Hayata, T., Amagasa, T., Denhardt, D., Ezura, Y., Nakashima, K., and Noda, M. (2007). Serum osteopontin, an enhancer of tumor metastasis to bone, promotes B16 melanoma cell migration. Journal of cellular biochemistry 101, 979-986.

Herum, K. M., Romaine, A., Wang, A., Melleby, A. O., Strand, M. E., Pacheco, J., Braathen, B., Duner, P., Tonnessen, T., Lunde, I. G., et al. (2020). Syndecan-4 Protects the Heart From the Profibrotic Effects of Thrombin-Cleaved Osteopontin. Journal of the American Heart Association 9, e013518.

Hisada, Y., and Mackman, N. (2019). Cancer cell-derived tissue factor-positive extracellular vesicles: biomarkers of thrombosis and survival. Current opinion in hematology 26, 349-356.

Ito, M., Hiramatsu, H., Kobayashi, K., Suzue, K., Kawahata, M., Hioki, K., Ueyama, Y., Koyanagi, Y., Sugamura, K., Tsuji, K., et al. (2002). NOD/SCID/gamma(c)(null) mouse: an excellent recipient mouse model for engraftment of human cells. Blood 100, 3175-3182.

Jablonski, K. A., Amici, S. A., Webb, L. M., Ruiz-Rosado Jde, D., Popovich, P. G., Partida-Sanchez, S., and Guerau-de-Arellano, M. (2015). Novel Markers to Delineate Murine M1 and M2 Macrophages. PLoS One 10, e0145342.

Kahale, L. A., Hakoum, M. B., Tsolakian, I. G., Matar, C. F., Terrenato, I., Sperati, F., Barba, M., Yosuico, V. E., Schunemann, H., and Akl, E. A. (2018). Anticoagulation for the long-term treatment of venous thromboembolism in people with cancer. The Cochrane database of systematic reviews 6, CD006650.

Kale, S., Raja, R., Thorat, D., Soundararajan, G., Patil, T. V., and Kundu, G. C. (2014). Osteopontin signaling upregulates cyclooxygenase-2 expression in tumor-associated macrophages leading to enhanced angiogenesis and melanoma growth via alpha9beta1 integrin. Oncogene 33, 2295-2306.

Kale, S., Raja, R., Thorat, D., Soundararajan, G., Patil, T. V., and Kundu, G. C. (2015). Osteopontin signaling upregulates cyclooxygenase-2 expression in tumor-associated macrophages leading to enhanced angiogenesis and melanoma growth via alpha9beta1 integrin. Oncogene 34, 5408-5410.

Katagiri, Y. U., Murakami, M., Mori, K., Iizuka, J., Hara, T., Tanaka, K., Jia, W. Y., Chambers, A. F., and Uede, T. (1996). Non-RGD domains of osteopontin promote cell adhesion without involving alpha v integrins. Journal of cellular biochemistry 62, 123-131.

Kawahara, K., Hohjoh, H., Inazumi, T., Tsuchiya, S., and Sugimoto, Y. (2015). Prostaglandin E2-induced inflammation: Relevance of prostaglandin E receptors. Biochim Biophys Acta 1851, 414-421.

Kirszberg, C., Lima, L. G., Da Silva de Oliveira, A., Pickering, W., Gray, E., Barrowcliffe, T. W., Rumjanek, V. M., and Monteiro, R. Q. (2009). Simultaneous tissue factor expression and phosphatidylserine exposure account for the highly procoagulant pattern of melanoma cell lines. Melanoma research 19, 301-308.

Komohara, Y., Fujiwara, Y., Ohnishi, K., and Takeya, M. (2016). Tumor-associated macrophages: Potential therapeutic targets for anti-cancer therapy. Advanced drug delivery reviews 99, 180-185.

Kothari, A. N., Arffa, M. L., Chang, V., Blackwell, R. H., Syn, W. K., Zhang, J., Mi, Z., and Kuo, P. C. (2016). Osteopontin-A Master Regulator of Epithelial-Mesenchymal Transition. J Clin Med 5.

Kumar, S., Sharma, P., Kumar, D., Chakraborty, G., Gorain, M., and Kundu, G. C. (2013). Functional characterization of stromal osteopontin in melanoma progression and metastasis. PLoS One 8, e69116.

Lamort, A. S., Giopanou, I., Psallidas, I., and Stathopoulos, G. T. (2019). Osteopontin as a Link between Inflammation and Cancer: The Thorax in the Spotlight. Cells 8.

Leung, L. L. K., and Morser, J. (2018). Carboxypeptidase B2 and carboxypeptidase N in the crosstalk between coagulation, thrombosis, inflammation, and innate immunity. J Thromb Haemost 16, 1474-1486.

Lima, L. G., and Monteiro, R. Q. (2013). Activation of blood coagulation in cancer: implications for tumour progression. Biosci Rep 33.

Lucotti, S., Cerutti, C., Soyer, M., Gil-Bernabe, A. M., Gomes, A. L., Allen, P. D., Smart, S., Markelc, B., Watson, K., Armstrong, P. C., et al. (2019). Aspirin blocks formation of metastatic intravascular niches by inhibiting platelet-derived COX-1/thromboxane A2. J Clin Invest 129, 1845-1862.

Lund, S. A., Giachelli, C. M., and Scatena, M. (2009). The role of osteopontin in inflammatory processes. J Cell Commun Signal 3, 311-322.

Mantovani, A., and Sica, A. (2010). Macrophages, innate immunity and cancer: balance, tolerance, and diversity. Curr Opin Immunol 22, 231-237.

Matar, C. F., Kahale, L. A., Hakoum, M. B., Tsolakian, I. G., Etxeandia-lkobaltzeta, I., Yosuico, V. E., Terrenato, I., Sperati, F., Barba, M., Schunemann, H., et al. (2018). Anticoagulation for perioperative thromboprophylaxis in people with cancer. The Cochrane database of systematic reviews 7, CD009447.

McAllister, S. S., Gifford, A. M., Greiner, A. L., Kelleher, S. P., Saelzler, M. P., Ince, T. A., Reinhardt, F., Harris, L. N., Hylander, B. L., Repasky, E. A., et al. (2008). Systemic endocrine instigation of indolent tumor growth requires osteopontin. Cell 133, 994-1005.

Mills, C. D. (2012). M1 and M2 Macrophages: Oracles of Health and Disease. Crit Rev Immunol 32, 463-488.

Myles, T., Nishimura, T., Yun, T. H., Nagashima, M., Morser, J., Patterson, A. J., Pearl, R. G., and Leung, L. L. (2003). Thrombin activatable fibrinolysis inhibitor, a potential regulator of vascular inflammation. J Biol Chem 278, 51059-51067.

Natoli, G., and Monticelli, S. (2014). Macrophage activation: glancing into diversity. Immunity 40, 175-177.

Nemoto, H., Rittling, S. R., Yoshitake, H., Furuya, K., Amagasa, T., Tsuji, K., Nifuji, A., Denhardt, D. T., and Noda, M. (2001). Osteopontin deficiency reduces experimental tumor cell metastasis to bone and soft tissues. J Bone Miner Res 16, 652-659.

Netea-Maier, R. T., Smit, J. W. A., and Netea, M. G. (2018). Metabolic changes in tumor cells and tumor-associated macrophages: A mutual relationship. Cancer letters 413, 102-109.

Niers, T. M., Bruggemann, L. W., GL, V. A. N. S., Liu, R. D., Versteeg, H. H., Buller, H. R., C J, V. A. N. N., Reitsma, P. H., Spek, C. A., and Richel, D. J. (2009). Long-term thrombin inhibition promotes cancer cell extravasation in a mouse model of experimental metastasis. J Thromb Haemost 7, 1595-1597.

O'Rorke, M. A., Murray, L. J., Hughes, C. M., Cantwell, M. M., and Cardwell, C. R. (2015). The effect of warfarin therapy on breast, colorectal, lung, and prostate cancer survival: a population-based cohort study using the Clinical Practice Research Datalink. Cancer causes & control: CCC 26, 355-366.

Ohyama, Y., Nemoto, H., Rittling, S., Tsuji, K., Amagasa, T., Denhardt, D. T., Nifuji, A., and Noda, M. (2004). Osteopontin-deficiency suppresses growth of B16 melanoma cells implanted in bone and osteoclastogenesis in co-cultures. Journal of bone and mineral research: the official journal of the American Society for Bone and Mineral Research 19, 1706-1711.

Qian, B. Z., and Pollard, J. W. (2010). Macrophage diversity enhances tumor progression and metastasis. Cell 141, 39-51.

Rittling, S. R., and Singh, R. (2015). Osteopontin in Immune-mediated Diseases. Journal of dental research 94, 1638-1645.

Ruf, W., Rothmeier, A. S., and Graf, C. (2016). Targeting clotting proteins in cancer therapy—progress and challenges. Thromb Res 140 Suppl 1, S1-7.

Sangaletti, S., Tripodo, C., Sandri, S., Torselli, I., Vitali, C., Ratti, C., Botti, L., Burocchi, A., Porcasi, R., Tomirotti, A., et al. (2014). Osteopontin shapes immunosuppression in the metastatic niche. Cancer research 74, 4706-4719.

Schuliga, M. (2015). The inflammatory actions of coagulant and fibrinolytic proteases in disease. Mediators of inflammation 2015, 437695.

Shao, Z., Morser, J., and Leung, L. L. (2014). Thrombin cleavage of osteopontin disrupts a pro-chemotactic sequence for dendritic cells, which is compensated by the release of its pro-chemotactic C-terminal fragment. J Biol Chem 289, 27146-27158.

Sharif, S. A., Du, X., Myles, T., Song, J. J., Price, E., Lee, D. M., Goodman, S. B., Nagashima, M., Morser, J., Robinson, W. H., et al. (2009). Thrombin-activatable carboxypeptidase B-cleavage of osteopontin regulates neutrophil survival and synoviocyte binding in rheumatoid arthritis. Arthritis and rheumatism 60, 2902-2912.

Shevde, L. A., and Samant, R. S. (2014). Role of osteopontin in the pathophysiology of cancer. Matrix biology: journal of the International Society for Matrix Biology 37, 131-141.

Sodek, J., Ganss, B., and McKee, M. D. (2000). Osteopontin. Crit Rev Oral Biol Med 11, 279-303.

Sparkenbaugh, E. M., Chantrathammachart, P., Mickelson, J., van Ryn, J., Hebbel, R. P., Monroe, D. M., Mackman, N., Key, N. S., and Pawlinski, R. (2014). Differential contribution of FXa and thrombin to vascular inflammation in a mouse model of sickle cell disease. Blood 123, 1747-1756.

Toda, M., Shao, Z., Yamaguchi, K. D., Takagi, T., D'Alessandro-Gabazza, C. N., Taguchi, O., Salamon, H., Leung, L. L., Gabazza, E. C., and Morser, J. (2013).

Differential gene expression in thrombomodulin (TM; CD141)(+) and TM(−) dendritic cell subsets. PLoS One 8, e72392.

Uede, T. (2011). Osteopontin, intrinsic tissue regulator of intractable inflammatory diseases. Pathol Int 61, 265-280.

Van Rooijen, N., and Sanders, A. (1994). Liposome mediated depletion of macrophages: mechanism of action, preparation of liposomes and applications. Journal of immunological methods 174, 83-93.

Wang, K. X., and Denhardt, D. T. (2008). Osteopontin: role in immune regulation and stress responses. Cytokine Growth Factor Rev 19, 333-345.

Wei, J., Marisetty, A., Schrand, B., Gabrusiewicz, K., Hashimoto, Y., Ott, M., Grami, Z., Kong, L. Y., Ling, X., Caruso, H., et al. (2019). Osteopontin mediates glioblastoma-associated macrophage infiltration and is a potential therapeutic target. J Clin Invest 129, 137-149.

Weichand, B., Popp, R., Dziumbla, S., Mora, J., Strack, E., Elwakeel, E., Frank, A. C., Scholich, K., Pierre, S., Syed, S. N., et al. (2017). S1PR1 on tumor-associated macrophages promotes lymphangiogenesis and metastasis via NLRP3/IL-1beta. J Exp Med 214, 2695-2713.

Weiss, J. M., Renkl, A. C., Maier, C. S., Kimmig, M., Liaw, L., Ahrens, T., Kon, S., Maeda, M., Hotta, H., Uede, T., et al. (2001). Osteopontin is involved in the initiation of cutaneous contact hypersensitivity by inducing Langerhans and dendritic cell migration to lymph nodes. J Exp Med 194, 1219-1229.

Winkler, I. G., Sims, N. A., Pettit, A. R., Barbier, V., Nowlan, B., Helwani, F., Poulton, I. J., van Rooijen, N., Alexander, K. A., Raggatt, L. J., et al. (2010). Bone marrow macrophages maintain hematopoietic stem cell (HSC) niches and their depletion mobilizes HSCs. Blood 116, 4815-4828.

Wojtukiewicz, M. Z., Hempel, D., Sierko, E., Tucker, S. C., and Honn, K. V. (2015). Protease-activated receptors (PARs)—biology and role in cancer invasion and metastasis. Cancer Metastasis Rev 34, 775-796.

Xue, J., Schmidt, S. V., Sander, J., Draffehn, A., Krebs, W., Quester, I., De Nardo, D., Gohel, T. D., Emde, M., Schmidleithner, L., et al. (2014). Transcriptome-based network analysis reveals a spectrum model of human macrophage activation. Immunity 40, 274-288.

Yamaguchi, Y., Shao, Z., Sharif, S., Du, X. Y., Myles, T., Merchant, M., Harsh, G., Glantz, M., Recht, L., Morser, J., et al. (2013). Thrombin-cleaved fragments of osteopontin are overexpressed in malignant glial tumors and provide a molecular niche with survival advantage. J Biol Chem 288, 3097-3111.

Yokosaki, Y., Matsuura, N., Sasaki, T., Murakami, I., Schneider, H., Higashiyama, S., Saitoh, Y., Yamakido, M., Taooka, Y., and Sheppard, D. (1999). The integrin alpha (9)beta(1) binds to a novel recognition sequence (SVVYGLR) in the thrombin-cleaved amino-terminal fragment of osteopontin. J Biol Chem 274, 36328-36334.

Zhao, H., Chen, Q., Alam, A., Cui, J., Suen, K. C., Soo, A. P., Eguchi, S., Gu, J., and Ma, D. (2018). The role of osteopontin in the progression of solid organ tumour. Cell death & disease 9, 356.

Example 2

Combination Therapy with a Thrombin Inhibitor and a B-Raf Inhibitor for Treating Melanoma In a mouse melanoma model (B16 cell implant or metastasis), there are smaller implanted tumors and fewer metastases in mice with a mutation in their osteopontin (OPN) gene that renders the OPN resistant to thrombin (Example 1). This means that the tumor is dependent on thrombin for growth. This was confirmed by treating WT mice with a thrombin inhibitor, dabigatran etexilate (DE), and showing that in the presence of DE B16 tumors grew slower on the WT mice resulting in a similar outcome to that found in OPN-KI and OPN-KO mice. Therefore, a combination of a coagulation inhibitor, preferably a direct thrombin inhibitor such as dabigatran, with a B-Raf inhibitor such as dabrafenib or vemurafenib can be used for treating melanoma. Dabrafenib is targeted to B-Raf genes with a mutation (V600E/ K).

Currently, some melanoma patients are treated with a combination of a B-Raf inhibitor, dabrafenib, and the MEK inhibitor, trametinib. Adding a thrombin inhibitor to that combination might also improve outcomes as well as adding it to the treatment of melanoma patients receiving trametinib alone. In addition, other direct oral anti-coagulants that inhibit factor Xa or factor XIa as well as heparin or coumadin may be used in place of the thrombin inhibitor.

---

What is claimed is:

1. A method of treating an osteopontin (OPN)-associated cancer having elevated levels of OPN cleavage fragments, the method comprising administering to a subject in need thereof a therapeutically effective amount of an anti-coagulant that inhibits thrombin cleavage of OPN in combination with a therapeutically effective amount of a B-Raf inhibitor or a mitogen-activated protein kinase (MEK) inhibitor, or therapeutically effective amounts of the B-Raf inhibitor and the MEK inhibitor.

2. The method of claim 1, wherein the anticoagulant is a direct thrombin inhibitor.

3. The method of claim 2, wherein the thrombin inhibitor is selected from the group consisting of dabigatran, argatroban, inogatran, melagatran, ximelagatran, hirudin, bivalirudin, lepirudin, and desirudin.

4. The method of claim 1, wherein the B-Raf inhibitor is selected from the group consisting of dabrafenib, vemurafenib, sorafenib, LGX818, GDC-0879, and PLX-4720.

5. The method of claim 1, wherein the MEK inhibitor is selected from the group consisting of trametinib, cobimetinib, binimetinib, selumetinib, and PD-325901.

6. The method of claim 1, wherein the anti-coagulant, the B-Raf inhibitor, or the MEK inhibitor is administered according to a daily dosing regimen or intermittently.

7. The method of claim 1, wherein multiple cycles of treatment are administered to the subject for at least 6 months.

8. The method of claim 1, wherein the anti-coagulant or the B-Raf inhibitor is administered orally, intravenously, or topically.

9. The method of claim 1, wherein the OPN-associated cancer is melanoma.

10. The method of claim 9, wherein the melanoma is a B-RAF-mutated melanoma.

11. The method of claim 10, wherein the B-RAF-mutated melanoma comprises a V600E mutation or a V600K mutation.

12. The method of claim 9, wherein the melanoma is metastatic.

13. The method of claim 1, wherein the subject is human.

14. The method of claim 1, wherein the anti-coagulant is an inhibitor of factor Xa.

15. The method of claim 14, wherein the inhibitor of factor Xa is selected from the group consisting of rivaroxaban (Xarelto), apixaban (Eliquis), betrixaban, darexaban (YM150), edoxaban (Lixiana), otamixaban, letaxaban (TAK-442), eribaxaban, antistasin, warfarin, heparin, and fondaparinux.

16. The method of claim 1, wherein the anti-coagulant is an inhibitor of factor XIa.

17. The method of claim 16, wherein the inhibitor of factor XIa is selected from the group consisting of BMS-262084 ((2S,3R)-1-[4-(tert-butylcarbamoyl) piperazine-1-carbonyl]-3-[3-(diaminomethylideneamino) propyl]-4-oxoazetidine-2-carboxylic acid), BMS-724296, BMS-654457 (2-[3-[(2S,4R)-6-carbamimidoyl-4-methyl-4-phenyl-2,3-dihydro-1H-quinolin-2-yl]-5-(3-methylbutanoylamino)phenyl]-5-carbamoylbenzoic acid), BMS-986177 ((9R,13S)-13-[4-[5-chloro-2-(4-chlorotriazol-1-yl)phenyl]-6-oxopyrimidin-1-yl]-3-(difluoromethyl)-9-methyl-3,4,7,15-tetrazatricyclo[12.3.1.02,6]octadeca-1(18),2(6),4,14,16-pentaen-8-one), EP-7041 ((2S,3R)-3-([2-Aminopyridin-4-yl]methyl)-1-([{1R}-1-cyclohexylethyl] carbamoyl)-4-oxoazetidine-2-carboxylic acid), a ketoarginine-based peptidomimetic, a clavatadine, an aryl boronic acid, and a cyclic arginine-containing ketothiazole peptidomimetic.

18. The method of claim 1, further comprising administering an additional anti-cancer therapeutic agent.

19. The method of claim 18, wherein the additional anti-cancer therapeutic agent is a chemotherapeutic agent, an immunotherapeutic agent, a biologic therapeutic agent, a hormonal therapeutic agent, a pro-apoptotic agent, an angiogenesis inhibitor, a photoactive agent, a radiosensitizing agent, or a radioisotope.

\* \* \* \* \*